United States Patent [19]

Broadhurst et al.

[11] Patent Number: 5,304,549
[45] Date of Patent: Apr. 19, 1994

[54] AMINO ACID DERIVATIVES

[75] Inventors: Michael J. Broadhurst, Royston; Paul A. Brown, Hitchin; William H. Johnson, Hitchin; Geoffrey Lawton, Hitchin, all of England

[73] Assignee: Hoffmann-La Roche Inc., Nutley, N.J.

[21] Appl. No.: 823,212

[22] Filed: Jan. 21, 1992

[30] Foreign Application Priority Data

Feb. 1, 1991 [GB] United Kingdom ................ 9102194
Oct. 31, 1991 [GB] United Kingdom ................ 9123162

[51] Int. Cl.$^5$ .......................... C07F 9/28; C07F 9/06; C07C 93/10; C07C 259/04; C07C 259/06; A61K 31/675; A61K 31/16; A61K 31/185

[52] U.S. Cl. ................................ 514/80; 548/112; 548/413; 548/414; 548/431; 548/518; 548/557; 548/558; 558/170; 558/174; 562/621; 562/622; 562/623; 562/433; 562/533; 564/153; 514/79; 514/89; 514/91; 514/119; 514/232.8; 514/237.2; 514/296; 514/321; 514/326; 514/422; 514/426; 514/428; 514/575; 514/616; 514/825; 544/126; 544/130; 544/141; 544/157; 544/168; 546/23; 546/24; 546/200; 546/208

[58] Field of Search .............. 544/126, 130, 141, 157, 544/168; 546/23, 24, 200, 208; 548/518, 112, 413, 414, 431, 557, 558; 558/170, 174; 564/153; 514/232.8, 237.2, 79, 89, 91, 119, 80, 296, 326, 428, 575, 616, 321, 422, 426, 825, 80; 562/621, 622, 623, 433, 553

[56] References Cited

U.S. PATENT DOCUMENTS 4,885,283  12/1989  Broadhurst et al. ................ 514/78
4,918,105  4/1990   Cartwright et al. ................ 514/575
4,996,358  2/1991   Handa et al. ...................... 562/621
5,006,651  4/1991   Broadhurst et al. ................ 540/463

FOREIGN PATENT DOCUMENTS 0214639  9/1986  European Pat. Off. .
0274453  1/1988  European Pat. Off. .

OTHER PUBLICATIONS

Dayer J.-M. et al., Proc. Natl. Acad. Sci. USA, 73, 945 (1976).
Johnson-Wint, B., Anal. Biochem., 104, 175 (1980).

*Primary Examiner*—Cecilia Tsang
*Attorney, Agent, or Firm*—George M. Gould; George W. Johnston; Robert A. Silverman

[57] ABSTRACT

Compounds of the formula

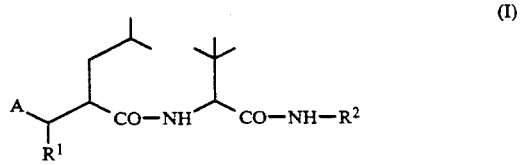

(I)

wherein A is the group

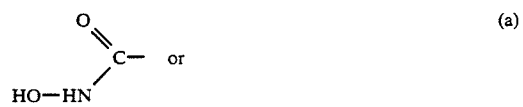

(a)

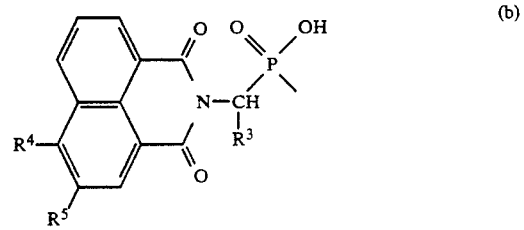

(b)

$R^1$ is hydrogen, amino, protected amino, acylamino or lower alkyl optionally substituted by aryl, hydroxy, protected hydroxy, amino, protected amino, acylamino, maleimido, succinimido, naphthalimido, 2,3-dihydro-1,3-dioxo-1H-benz[d,e]isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino; $R^2$ is hydrogen or lower alkyl optionally substi- (Abstract continued on next page.)

tuted by aryl, amino, protected amino, di(lower alkyl)-amino, guanidino, carboxyl, protected carboxyl, carbamoyl, mono(lower alkyl) carbamoyl, di(lower alkyl)-carbamoyl, di(lower alkoxy)phosphinyl, dihydroxyphosphinyl, pyrrolidino, piperidino or morpholino; $R^3$ is hydrogen or lower alkyl optionally substituted by hydroxy, protected hydroxy, amino or protected amino; $R^4$ is hydrogen, hydroxy, lower alkoxy or benzyloxy; and $R^5$ is hydrogen or halogen and their pharmaceutically acceptable salts, which are useful for the control or prevention of degenerative joint diseases or for the treatment of invasive tumors, atherosclerosis or multiple sclerosis are described.

45 Claims, No Drawings

AMINO ACID DERIVATIVES

BRIEF SUMMARY OF THE INVENTION

The present invention relates to compounds of the formula

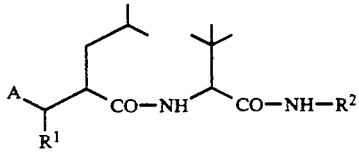  (I)

wherein
A is the group

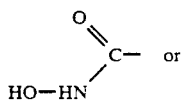  (a)

or

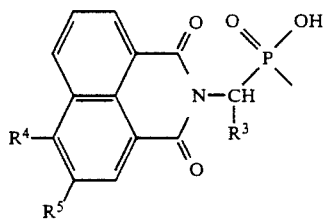  (b)

R¹ is hydrogen, amino, protected amino, acylamino, lower alkyl or lower alkyl substituted with aryl, hydroxy, protected hydroxy, amino, protected amino, acylamino, maleimido, succinimido, naphthalimido, 2,3-dihydro-1,3-dioxo-1H-benz[d,e]isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino;

R² is hydrogen, lower alkyl or lower alkyl substituted with aryl, amino, protected amino, di(lower alkyl)amino, guanidino, carboxyl, protected carboxyl, carbamoyl, mono(lower alkyl) carbamoyl, di(lower alkyl)carbamoyl, di(lower alkoxy)phosphinyl, dihydroxyphosphinyl, pyrrolidino, piperidino or morpholino;

R³ is hydrogen, lower alkyl, or lower alkyl substituted with hydroxy, protected hydroxy, amino or protected amino;

R⁴ is hydrogen, hydroxy, lower alkoxy or benzyloxy; and

R⁵ is hydrogen or halogen;

and pharmaceutically acceptable salts thereof.

DETAILED DESCRIPTION OF THE INVENTION

The present invention relates to amino acid derivatives of the formula

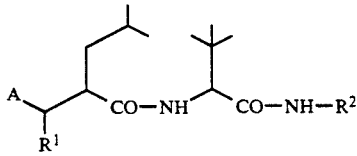  (I)

wherein
A is the group

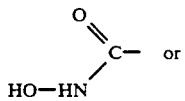  (a)

or

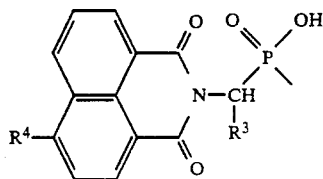  (b)

R¹ is hydrogen, amino, protected amino, acylamino, lower alkyl or lower alkyl substituted with aryl, hydroxy, protected hydroxy, amino, protected amino, acylamino, maleimido, succinimido, naphthalimido, 2,3-dihydro-1,3-dioxo-1H-benz[d,e]isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino;

R² is hydrogen, lower alkyl or lower alkyl substituted with aryl, amino, protected amino, di(lower alkyl)amino, guanidino, carboxyl, protected carboxyl, carbamoyl, mono(lower alkyl) carbamoyl, di(lower alkyl)carbamoyl, di(lower alkoxy)phosphinyl, dihydroxyphosphinyl, pyrrolidino, piperidino or morpholino;

R³ is hydrogen, lower alkyl, or lower alkyl substituted with hydroxy, protected hydroxy, amino or protected amino;

R⁴ is hydrogen, hydroxy, lower alkoxy or benzyloxy; and

R⁵ is hydrogen or halogen;

and pharmaceutically acceptable salts thereof.

The compounds of formula I possess valuable pharmacological properties. In particular, they are collagenase inhibitors and can be used in the control or prevention of degenerative joint diseases, such as, for example, rheumatoid arthritis and osteoarthritis, or in the treatment of invasive tumors, atherosclerosis or multiple sclerosis.

Objects of the present invention are the compounds of formula I and their pharmaceutically acceptable salts; a process for making these compounds and salts; medicaments containing the compounds of formula I and salts and the use of compounds of formula I and salts in the control or prevention of illnesses or in the improvement of health, especially in the control or prevention of degenerative joint diseases or in the treatment of invasive tumors or atherosclerosis.

As used in this Specification, the term "lower alkyl", alone or in combination, denotes a straight-chain or branched-chain alkyl group containing a maximum of six carbon atoms, such as, for example, methyl, ethyl, n-propyl, isopropyl, n-butyl, sec.butyl, isobutyl, tert.butyl, n-pentyl, n-hexyl and the like. Likewise, the term "lower alkoxy" denotes a straight-chain or branched-chain alkoxy group containing a maximum of six carbon atoms, such as, for example, methoxy, ethoxy, n-propoxy, isopropoxy, n-butoxy, tert.butoxy and the like. The term "aryl" denotes an optionally substituted phenyl or naphthyl group with the substituent(s) being selected, for example, from halogen, trifluoromethyl, lower alkyl, lower alkoxy, phenyl and the like. The acyl part of an acylamino group is derived from an alkanoic acid which contains a maximum of six carbon atoms, for example, acetyl, propionyl, butyryl, pivaloyl and the like; from an optionally substituted benzoic or naphthoic acid, for example, benzoyl, 4-chlorobenzoyl, 2-carboxybenzoyl, 1- or 2-naphthoyl and the like; or from an aryl-substituted alkanoic acid which contains a maximum of six carbon atoms, for example, phenylacetyl and the like. The lower alkanoyl part of a carboxy-lower alkanoylamino group is derived from an alkanoic acid which contains a maximum of six carbon atoms, for example, acetyl, propionyl, butyryl and the like. The term "halogen" denotes fluorine, chlorine, bromine or iodine.

The terms "protected amino", "protected hydroxy" and "protected carboxy" denote amino, hydroxy and carboxy groups, respectively, which are protected in a known manner, for example, as known in peptide chemistry. For example, an amino group can be protected by a benzyloxycarbonyl, tert.butoxycarbonyl, acetyl or like group or in the form of a phthalimido or like group. A hydroxy group can be protected, for example, in the form of a readily cleavable ether, such as, for example, the tert.butyl or benzyl ether or in the form of a readily cleavable ester, such as, for example, the acetate. A carboxy group can be protected, for example, in the form of a readily cleavable ester, such as, for example, the methyl, ethyl, benzyl or like ester.

The compounds of formula I form pharmaceutically acceptable salts with bases, such as, alkali metal hydroxides, for example, sodium hydroxide and potassium hydroxide, alkaline earth metal hydroxides, for example, calcium hydroxide and magnesium hydroxide, ammonium hydroxide and the like. The compounds of formula I which are basic form pharmaceutically acceptable salts with acids. As such salts there come into consideration not only salts with inorganic acids, such as, hydrohalic acids, for example, hydrochloric acid and hydrobromic acid, sulphuric acid, nitric acid, phosphoric acid and the like, but also salts with organic acids, such as, for example, acetic acid, tartaric acid, succinic acid, fumaric acid, maleic acid, malic acid, salicylic acid, citric acid, methanesulphonic acid, p-toluenesulphonic acid and the like.

The compounds of formula I contain at least two asymmetric carbon atoms and can accordingly exist as optically active enantiomers, as diastereoisomers or as racemates.

In the compounds of formula I provided by the present invention $R^1$ is preferably hydrogen, amino, acetylamino, benzyloxycarbonylamino, lower alkyl or lower alkyl substituted by amino, phenyl, phthalimido, succinimido, carboxy, alkoxycarbonyl, morpholino, hydroxy or acetoxy, especially hydrogen, amino, acetylamino, benzyloxycarbonylamino, methyl, 5-amino-pentyl, 4-phthalimidobutyl, 5-phthalimidopentyl, 5-hydroxypentyl, 5-acetoxypentyl, aminomethyl, phthalimidomethyl, succinimido-methyl, benzyl, 3-phenylpropyl, 3-carboxypropyl, 3-methoxy-carbonylpropyl, benzoylaminomethyl, morpholinomethyl, acetyl-aminomethyl, 2-phthalimidoethyl, 3-hydroxypropyl or 3-acetoxy-propyl. $R^2$ is preferably lower alkyl or lower alkyl substituted by amino, aryl, guanidino, carboxy, di(lower alkoxy)phosphinyl, dihdroxyphosphinyl or morpholino, especially methyl, 4-aminobutyl, 1-phenylethyl, 5-carboxypentyl, diethoxy- phosphinylmethyl, dihydroxyphosphinyl-methyl or 5-morpholino-pentyl. $R^3$ is preferably hydrogen, hydroxymethyl, 2-aminoethyl or 4-aminobutyl, especially hydrogen. Preferably, $R^4$ is hydrogen, hydroxy or benzyloxy, especially hydrogen or hydroxy. $R^5$ is preferably hydrogen or bromine.

The most preferred compounds of formula I provided by the present invention are:

$N^2$-[2(R)-[Hydroxycarbamoylmethyl]-4-methyl-valeryl]-$N^1$,3-dimethyl-L-valinamide, $N^2$-[2(R or S)-[1(S)-(hydroxycarbamoyl)ethyl]-4-methylvaleryl]-$N^1$,3-dimethyl-L-valinamide (isomer 2), $N^2$-[[2(R or S)-[[[(5-bromo-2,3-dihydro-6-hydroxy-1,3-dioxo-1H-benz[d,e]isoquinol-2-yl)methyl](hydroxy)-phosphinyl]methyl]-4-methylvaleryl]-$N^1$,3-dimethyl-L-valinamide, $N^2$-[2(R or S)-[[(R)-(amino)[(5-bromo-2,3-dihydro-6-hydroxy-1,3-dioxo-1H-benz[d,e]isoquinol-2-yl)methyl](hydroxy)phosphinyl]-methyl]-4-methyl-valeryl]-$N^1$,3-dimethyl-L-valinamide and $N^2$-[2(R or S)-[[(R)-(amino)[(2,3-dihydro-6-hydroxy-1,3-dioxo-1H-benz[d,e]isoquinol-2-yl)methyl](hydroxy)phosphinyl]-methyl]-4-methylvaleryl]-$N^1$,3-dimethyl-L-valinamide.

$N^2$-[2(R)-[1(R or S)-(hydroxycarbamoyl)-2-phthalimidoethyl]-4-methylvaleryl]-$N^1$,3-dimethyl-L-valinamide, $N^2$-[2(R)-[1(R or S)-(hydroxycarbamoyl)-4-(methoxycarbonyl)butyl]-4-methylvaleryl]-$N^1$,3-dimethyl-L-valinamide, $N^2$-[2(R)-[1(R or S)-(hydroxycarbamoyl)-4-phenylbutyl]-4-methylvaleryl]-$N^1$,3-dimethyl-L-valinamide and, $N^2$-[2(R)-[1(R or S)-(hydroxycarbamoyl)-2-succinimidoethyl]-4-methylvaleryl]-$N^1$,3-dimethyl-L-valinamide.

The compounds of formula I and their pharmaceutically acceptable salts can be prepared by (a) reacting an acid of the formula

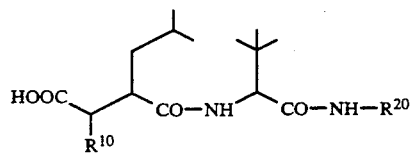

(II)

wherein $R^{10}$ is hydrogen, protected amino, acylamino, lower alkyl or lower alkyl substituted by aryl, protected hydroxy, protected amino, acylamino, maleimido, succinimido, naphthalimido, 2,3-dihydro-1,3-dioxo-1H-benz[d,e]isoquinol-2-yl, protected carboxyl, carbamoyl, mono(lower alkyl)carbamoyl, di(lower alkyl)carbamoyl, di(lower alkyl)amino, carboxy-lower alkanoylamino, pyrrolidino or morpholino and $R^{20}$ is hydrogen, lower alkyl or lower alkyl substituted by aryl, protected amino, di(lower alkyl)amino, protected carboxyl, carbamoyl, mono(lower alkyl)carbamoyl, di(lower alkyl)carbamoyl, di(lower alkoxy)-phosphinyl, pyrrolidino, piperidino or morpholino, with a compound of the formula

    (III)

wherein Z is hydrogen, tri(lower alkyl)silyl or diphenyl(lower alkyl)silyl, and, where required, cleaving off any diphenyl(lower alkyl(silyl group present in the reaction product, or (b) catalytically hydrogenating a compound of the formula

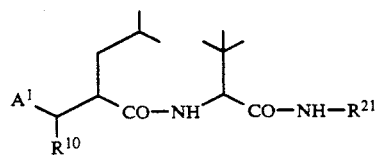    (IV)

wherein $A^1$ is benzyloxyformamido, $R^{10}$ has the significance given earlier and $R^{21}$ has any of the values of $R^{20}$ given earlier or represents nitroguanidino, or (c) reacting an amine of the formula

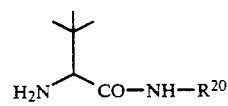    (V)

wherein $R^{20}$ has the significance given earlier, with an acid of the formula

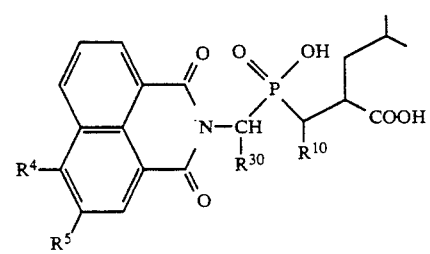    (VI)

wherein $R^4$, $R^5$ and $R^{10}$ have the significance given earlier and $R^{30}$ is hydrogen, lower alkyl or lower alkyl substituted by protected hydroxy or protected amino, (d) treating a compound of the formula

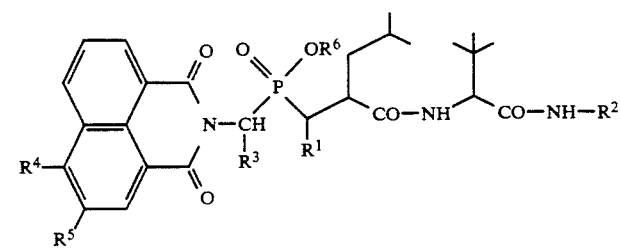    (VII)

wherein $R^1$, $R^2$, $R^3$, $R^4$ and $R^5$ have the significance given earlier and $R^6$ represents lower alkyl, with an acid or a halotri(lower alkyl)silane, or (e) reacting a compound of the general formula

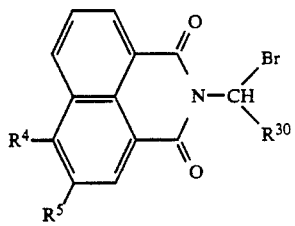    (VIII)

wherein $R^4$, $R^5$ and $R^{30}$ have the significance given earlier, with a compound of the formula

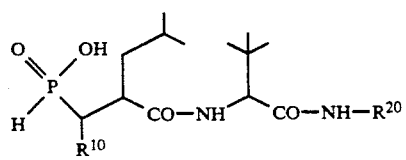    (IX)

wherein $R^{10}$ and $R^{20}$ have the significance given earlier, or (f) brominating a compound of formula I in which A is a group of formula (b) wherein $R^4$ is hydroxy and $R^5$ is hydrogen, or (g) cleaving off the protecting group(s) from a compound of formula I in which $R^1$ is protected amino or lower alkyl substituted by protected hydroxy or protected amino and/or $R^2$ is lower alkyl substituted by protected amino or protected carboxyl and/or $R^3$ is lower alkyl substituted by protected hydroxy or protected amino, or (h) treating a compound of formula I in which $R^2$ is di(lower alkoxy)phosphinyl-(lower alkyl) with an acid or with a halotri(lower alkyl)silane, or (i) acylating a compound of formula I in which $R^1$ is amino or amino-lower alkyl, or (j) ring-opening a compound of formula I in which $R^1$ is phthalimido-(lower alkyl) or succinimido-(lower alkyl), and (k) if desired, converting a compound of formula I obtained into a pharmaceutically acceptable salt.

The reaction of an acid of formula II with a compound of formula III in accordance with embodiment (a) of the process can be carried out in a known manner, for example, in an inert organic solvent, such as, dimethylformamide or the like, using hydroxy- benzotriazole in the presence of a condensation agent, such as, 1-(3-dimethylaminopropyl)-3-ethylcarbodiimide, at about 0° C. to about room temperature. Preferred compounds of formula III are those in which Z is hydrogen, tert.butyldimethylsilyl or tert.butyldiphenylsilyl. When a compound of formula III in which Z is tri(lower alkyl)silyl is used, this group is cleaved off during the reaction and a compound of formula I is obtained directly. On the other hand, when a compound of formula III in which Z is diaryl(lower alkyl)silyl is used, this group remains in the reaction product and must subsequently be cleaved off in a known manner, for example, by means of fluoride ions.

The catalytic hydrogenation of a compound of formula IV in accordance with embodiment (b) of the process can be carried out in a known manner; for example, in an inert organic solvent using hydrogen in the presence of a noble metal catalyst. Suitable inert organic solvents are, for example, lower alkanols such as methanol, ethanol, and the like. With respect to the catalyst, this can be, for example, a platinum, palladium or rhodium catalyst which can be supported on a suitable carrier material. Palladium-on-charcoal is the preferred catalyst. The temperature and pressure are not critical, although the catalytic hydrogenation is preferably carried out at room temperature and under atmospheric pressure.

The reaction of an amine of formula V with an acid of formula VI in accordance with embodiment (c) of the process can be carried out by heating the amine with the acid in an inert organic solvent, such as, an aromatic hydrocarbon, especially toluene or a xylene, at a temperature of about 30° C. to about 150° C., preferably at the reflux temperature of the reaction mixture. If desired, the heating can be carried out in the presence of a tertiary organic base. Alternatively, the reaction can be carried out in a known manner by firstly reacting an acid of formula VI with a reagent such as oxalyl chloride followed by condensation with an amine of formula V in the presence of a tertiary organic base. This embodiment can be carried out, for example, in an inert organic solvent, such as a halogenated aliphatic hydrocarbon, for example, dichloromethane or the like, an aromatic hydrocarbon, such as toluene or the like or a mixture of such solvents, at a temperature between about −25° C. and about room temperature, preferably at about room temperature.

The treatment of a compound of formula VII with an acid or with a halotri(lower alkyl)silane, preferably a halotrimethylsilane such as bromotrimethylsilane, in accordance with embodiment (d) of the process can be carried out in a known manner. Thus, for example, a compound of formula VII can be treated with a hydrogen halide, preferably hydrogen bromide, in a lower alkanoic acid, preferably acetic acid, conveniently at about room temperature, or with trifluoroacetic acid in an inert organic solvent, for example, a halogenated hydrocarbon, such as dichloromethane or the like, conveniently at about room temperature. A compound of formula VII can be treated with a halotri(lower alkyl)silane in an inert organic solvent, for example, a halogenated aliphatic hydrocarbon, such as dichloromethane or the like, conveniently at about room temperature.

The reaction of a compound of formula VIII with a compound of formula IX in accordance with embodiment (e) of the process can be carried out in a known manner. For example, the reaction can be carried out in an inert organic solvent, such as a halogenated aliphatic hydrocarbon, for example, chloroform or the like, in the presence of a silylating agent, such as bis(trimethylsilyl)acetamide, with the mixture being acidified, for example, with a mineral acid such as hydrochloric acid, after the reaction has been effected. This reaction is suitably carried out at an elevated temperature, for example, about 50°–60° C.

The bromination in accordance with embodiment (f) of the process can be carried out in a known manner. Suitably, the bromination is carried out using bromine in an inert organic solvent, such as, an alkanoic acid, for example, acetic acid and the like, with the bromine conveniently being introduced as a solution in a halogenated hydrocarbon, for example, dichloromethane and the like. The bromination is expediently carried out at about room temperature.

The cleavage of the protecting group(s) in accordance with embodiment (g) of the process can be carried out using methods which are known in peptide chemistry. For example, the cleavage of a protected amino group to an amino group can be carried out by acidolysis using a mineral acid, for example, hydrochloric acid, or trifluoroacetic acid when the protecting group is tert.-butoxycarbonyl, by catalytic hydrogenolysis when the protecting group is benzyloxycarbonyl or by hydrazinolysis when the protecting group is phthaloyl. The cleavage of a protected hydroxy group to a hydroxy group can be carried out, for example, by acidolysis when the protecting group is tert.butyl, by catalytic hydrogenolysis when the protecting group is benzyl or by basification when protection is in the form of an ester, for example, acetate. The cleavage of a protected carboxy group can be carried out, for example, by basification with, for example, an aqueous alkali metal hydroxide, such as aqueous sodium hydroxide or potassium hydroxide.

The treatment in accordance with embodiment (h) of the process can be carried out in a known manner. Thus, for example, the treatment can be carried out using a hydrogen halide, preferably hydrogen bromide, in a lower alkanoic acid, preferably acetic acid, conveniently at about room temperature, or using trifluoroacetic acid in an inert organic solvent, for example, a halogenated hydrocarbon, such as dichloromethane or the like, conveniently at about room temperature. The treatment can be carried out, for example, using a halotri(lower alkyl)silane in an inert organic solvent, for example, a halogenated hydrocarbon, such as dichloromethane or the like, conveniently at about room temperature.

The acylation in accordance with embodiment (i) of the process can be carried out in a known manner, for example, using an acid halide, for example, an acetyl halide, or, preferably, an acid anhydride, for example, acetic anhydride and the like, in an inert organic solvent and in the presence of a base. The base is preferably an organic base, especially pyridine, which can conveniently be used in excess and can thus simultaneously serve as the solvent. The acylation is suitably carried out at about room temperature.

The ring-opening of a compound of formula I in which $R^1$ is phthalimido-(lower alkyl) or succinimido-(lower alkyl) in accordance with embodiment (j) of the process leads to a corresponding compound of formula I in which $R^1$ is (2-carboxybenzoyl) amino-(lower alkyl) or 3-carboxypropionamido-(lower alkyl), respectively. The ring-opening can be carried out in a known manner, for example by treatment with lithium hydroxide in a known manner, for example, in a lower alkanol and suitably at about room temperature.

In accordance with embodiment (k) of the process, acidic compounds of formula I can be converted into pharmaceutically acceptable salts by treatment with bases and basic compounds of formula I can be converted into pharmaceutically acceptable salts by treatment with acids. Such treatments can be carried out in a conventional manner.

The acids of formula II which are used as starting materials in embodiment (a) of the process are novel and form a further object of the present invention.

The acids of formula II can be prepared according to the procedure illustrated in Reaction Scheme I hereinafter in which $R^{10}$ and $R^{20}$ have the significance given earlier and $R^7$ is a protecting group such as tert.butyl, benzyl or the like:

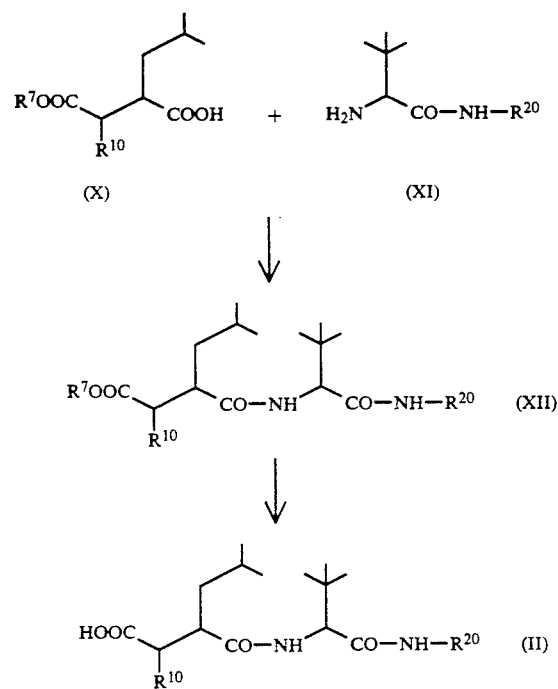

In the first stage of Reaction Scheme I, an acid of formula X is condensed with an amine of formula XI. This condensation can be carried out in a manner which is known in peptide chemistry. Thus, for example, the condensation can be carried out according to the well-known acid halide, acid anhydride, activated amide, mixed anhydride or activated ester method. In a preferred procedure, the condensation is carried out according to the activated ester method, particularly using hydroxybenzotriazole in the presence of a condensation agent such as N,N'-dicyclohexylcarbodiimide.

In the next stage of Reaction Scheme I, a compound of formula XII is converted into an acid of formula II by cleavage of the protecting group $R^7$. This cleavage is carried out in a known manner; for example, by treatment with acid, such as hydrogen bromide, in glacial acetic acid or trifluoroacetic acid when $R^7$ is tert.butyl or by hydrogenolysis when $R^7$ is benzyl.

The compounds of formula III which are used as starting materials in embodiment (a) of the process are known compounds.

The compounds of formula IV which are used as starting materials in embodiment (b) of the process are novel and form a further object of the present invention.

The compounds of formula IV can be prepared by reacting an acid of formula II or a corresponding acid in which $R^{20}$ is nitroguanidino with O-benzylhydroxylamine. This reaction can be carried out in a conventional manner, for example, in an inert organic solvent, such as a chlorinated aliphatic hydrocarbon, for example, dichloromethane or the like, in the presence of a condensation agent, such as di(1-benzotriazolyl) carbonate and at about room temperature.

The amines of formula V which are used as starting materials in embodiment (c) of the process are known compounds or analogues of known compounds which can be prepared in a manner analogous to the known compounds.

The acids of formula VI which are used as starting materials in embodiment (c) of the process are novel and also form an object of the present invention.

The acids of formula VI can be prepared according to the procedure illustrated in Reaction Scheme II hereinafter in which $R^4$ and $R^5$ and $R^{10}$ have the significance given earlier, $R^8$ is lower alkyl or aryl-(lower alkyl) and $R^{30}$ is hydrogen, lower alkyl or lower alkyl substituted by protected hydroxy or protected amino:

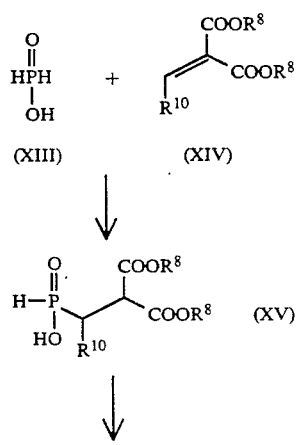

Reaction Scheme II -continued

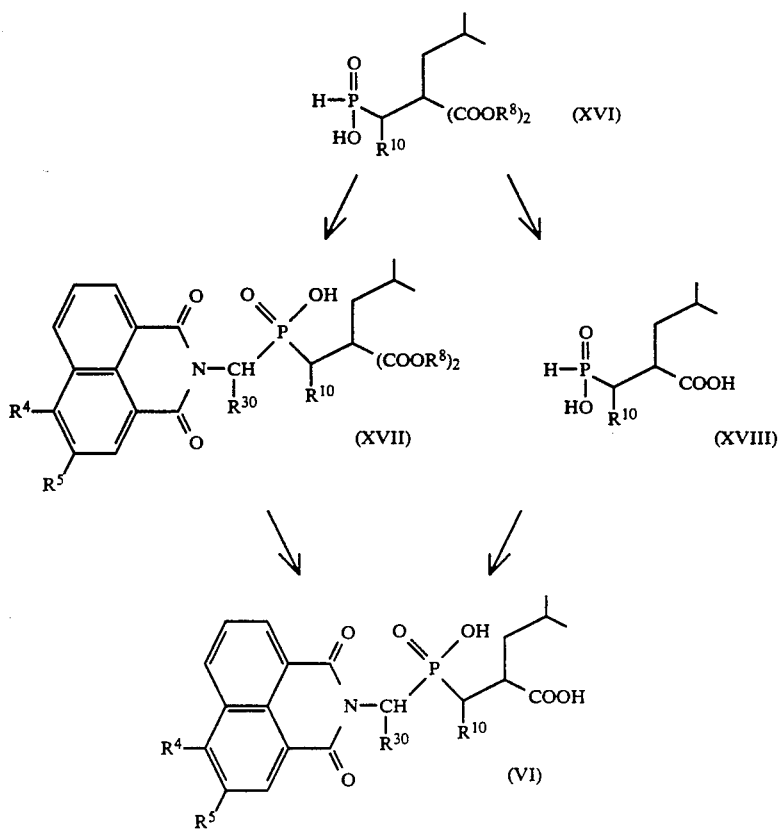

In the first stage of Reaction Scheme II, hypophosphorous acid of formula XIII is reacted with a compound of formula XIV to give a compound of formula XV. This reaction is carried out in a known manner, for example, in an inert organic solvent, such as a halogenated aliphatic hydrocarbon, for example, dichloromethane or the like, in the presence of a silylating agent, such as bis(trimethyl-silyl)acetamide and an amine, such as 1,1,3,3-tetra-methylguanidine, at about 0° C. to about room temperature, with the reaction mixture being acidified with, for example, hydrochloric acid after the reaction has finished.

A compound of formula XV is then converted into a compound of formula XVI by reaction with isobutyl bromide or iodide. This reaction is carried out in a conventional manner, for example, in an inert organic solvent, such as dimethyl sulphoxide and the like, and in the presence of a base, for example, an alkali metal hydride, such as sodium hydride, at about 5° C. to about room temperature.

A compound of formula XVI can be converted into either a compound of formula XVII or a compound of formula XVIII. Further, a compound of formula XVI is a suitable stage at which to carry out a resolution into optical isomers.

The conversion of a compound of formula XVI into a compound of formula XVII can be carried out in a manner analogous to that described earlier in connection with the reaction of a compound of formula VIII with a compound of formula IX according to embodiment (d) of the process of the invention.

A compound of formula XVII is then converted into an acid of formula VI by hydrolysis and decarboxylation according to known procedures. The actual methods used will depend on the nature of the substituents present in the molecule and will be familiar to a person skilled in the art. Further, the hydrolysis and decarboxylation can be carried out stepwise in certain circumstances.

The conversion of a compound of formula XVI into a compound of formula XVIII can be carried out in a manner analogous to the conversion of a compound of formula XVII into an acid of formula VI. The conversion of a compound of formula XVIII into an acid of formula VI can be carried out in a manner analogous to the conversion of a compound of formula XVI into a compound of formula XVII.

An acid of formula VI obtained can be functionally modified if desired. For example, an acid of formula VI in which $R^4$ is benzyloxy and $R^5$ is hydrogen can be catalytically hydrogenated to give an acid of formula VI in which $R^4$ is hydroxy and $R^5$ is hydrogen and the latter can be brominated to give an acid of formula VI in which $R^4$ is hydroxy and $R^5$ is bromine. The bromination are carried out in a manner analogous to that described earlier in connection with embodiment (e) of the process provided by the invention.

The compounds of formula VII which are used as starting materials in embodiment (c) of the process are novel and form a further object of the present invention.

The compounds of formula VII can be prepared according to the procedure illustrated in Reaction Scheme III hereinafter in which $R^1$, $R^2$, $R^6$, $R^{10}$, $R^{20}$ and $R^{30}$ have the significance given earlier:

Reaction Scheme III

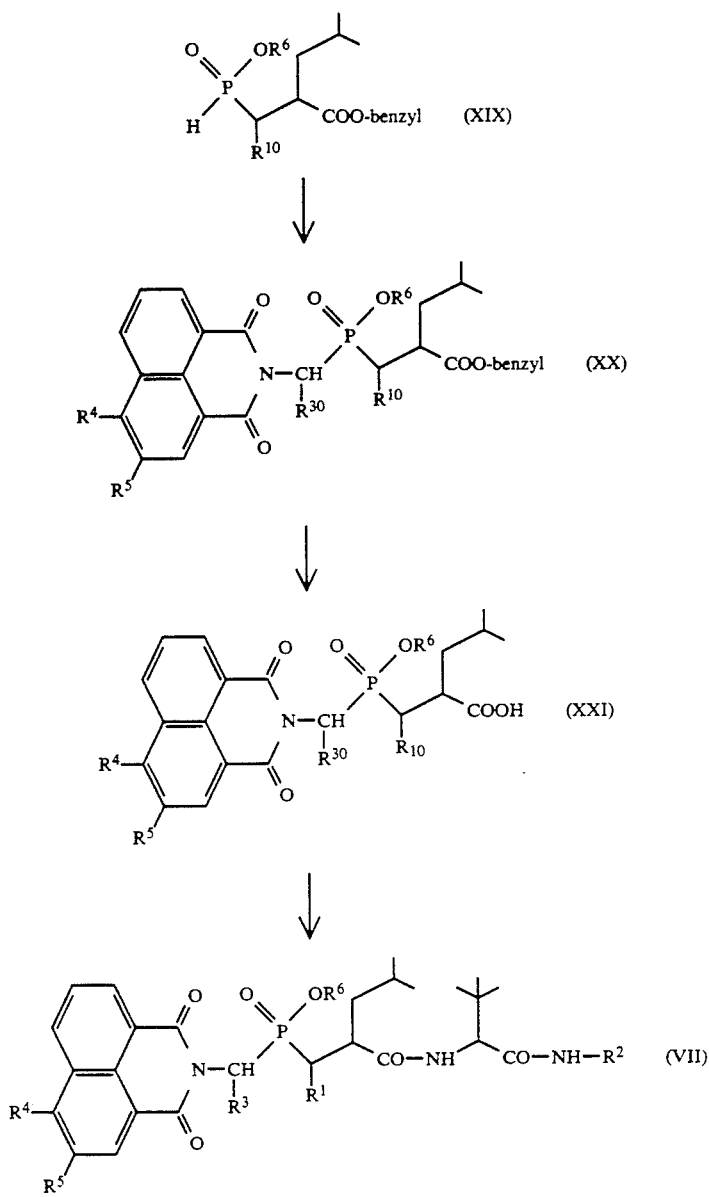

In the first stage of Reaction Scheme III, a compound of formula XIX is reacted with a compound of formula VIII hereinbefore to give a compound of formula XX. This reaction is carried out in a manner analogous to that described earlier in connection with the reaction of a compound of formula VIII with a compound of formula IX.

A compound of formula XX is then debenzylated by catalytic hydrogenation in a conventional manner to give a compound of formula XXI.

Subsequently, a compound of formula XXI is coupled with an amine of formula V hereinbefore in accordance with methods known in peptide chemistry and, if desired, any protected amino, protected hydroxy or protected carboxy group present in the product is converted into an amino, hydroxy or carboxy group according to known methods.

An alternative procedure for the preparation of compounds of formula XXI in which $R^3$ is lower alkyl substituted by protected hydroxy or protected amino is illustrated in Reaction Scheme IV hereinafter in which $R^4$, $R^5$, $R^6$ and $R^{10}$ have the significance given earlier and $R^{31}$ is lower alkyl substituted by protected hydroxy or protected amino in which the protecting group is other than a hydrogenolytically-removable protecting group:

Reaction Scheme IV

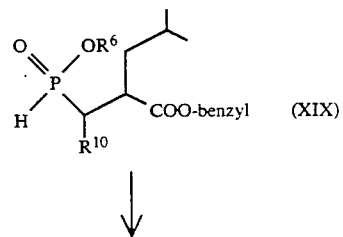

-continued
Reaction Scheme IV

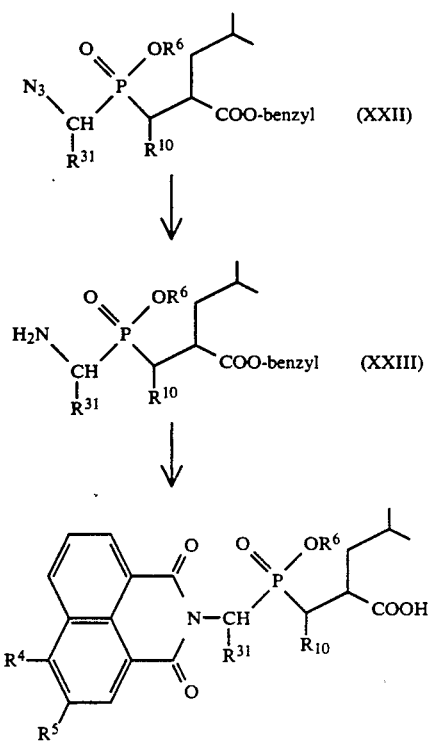

In Reaction Scheme IV, a compound of formula XIX is converted into a compound of formula XXII by reaction with an aldehyde of the formula $R^{31}$—CHO, in which $R^{31}$ has the significance given earlier, activating the hydroxy group in the product obtained and reacting the activated product with an alkali metal azide. These steps are carried out in a known manner. For example, the reaction of a compound of formula XIX with the aldehyde can be carried out in an inert organic solvent, such as an aromatic hydrocarbon, for example, toluene or the like, in the presence of a base such as 1,1,3,3-tetramethyl-guanidine at about room temperature. The activation of the hydroxy group can be carried out by conversion into a corresponding alkanesulphonyloxy, for example, methanesulphonyloxy, compound using an alkanesulphonyl halide, for example, methanesulphonyl chloride, in the presence of an acid-binding agent, for example, pyridine or the like, and in an inert organic solvent, for example, a halogenated aliphatic hydrocarbon, such as dichloromethane or the like, at about 0° C. to room temperature. The reaction with an alkali metal azide, preferably sodium azide, is conveniently carried out in an inert organic solvent, such as dimethylformamide or the like and at an elevated temperature, for example, about 60°–80° C.

Subsequently, a compound of formula XXII is converted into a compound of formula XXIII in a known manner, for example, by treatment in an inert organic solvent, such as a lower alkanol, for example, methanol or the like, with an alkanedithiol, for example, 1,3-propanedithiol, in the presence of a tri(lower alkyl)amine, for example, triethylamine or the like, at about room temperature.

A compound of formula XXIII is then reacted with a compound of the general formula

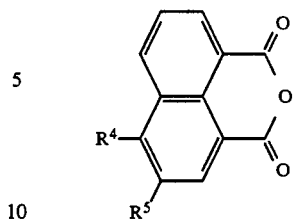

wherein $R^4$ and $R^5$ have the significance given earlier, and the reaction product obtained is debenzylated.

The reaction of a compound of formula XXIII with a compound of formula XXIV can be carried out in a known manner, for example, in an inert organic solvent, such as a halogenated aliphatic hydrocarbon, for example, dichloromethane or the like, and in the presence of a tertiary amine, such as N-ethyl-morpholine or the like, at about room temperature. The subsequent debenzylation is carried out in a conventional manner.

A compound of formula XXI or XXIa obtained can be functionally modified if desired. For example, a compound of formula XXI or XXIa in which $R^4$ is benzyloxy and $R^5$ is hydrogen can be catalytically hydrogenated to give a compound of formula XXI or XXIa in which $R^4$ is hydroxy and $R^5$ is hydrogen and the latter can be brominated in a manner analogous to that described earlier in connection with embodiment (e) of the process provided by the invention to give a compound of formula XXI or XXIa in which $R^4$ is hydroxy and $R^5$ is bromine.

Further, a protecting group present in $R^{31}$ can be inter-changed at any stage of the procedure illustrated by Reaction Scheme IV.

The compounds of formula VIII which are used as starting materials in embodiment (d) of the process are known compounds or analogues of known compounds which can be prepared in a similar manner to the known compounds.

The compounds of formula IX which are also used as starting materials in embodiment (d) of the process are novel and also form an object of the invention.

The compounds of formula IX can be prepared, for example, by reacting a compound of formula XVIII hereinbefore with an amine of formula V hereinbefore. This reaction can be carried out in a manner analogous to that described earlier in connection with the reaction of an amine of formula V with an acid of formula VI in accordance with embodiment (c) of the process provided by the invention.

The compounds of formulae X, XI, XIII, XIV and XIX which are used as starting materials in the foregoing Reaction Schemes and the compounds of formula XXIV hereinbefore are known compounds or analogues of known compounds which can be prepared in a similar manner to the known compounds or as described in the Examples hereinafter or in analogy thereto.

As mentioned earlier, the compounds of formula I and their pharmaceutically acceptable salts are collagenase inhibitors. The in vitro collagenase inhibiting activity of the present compounds and salts can be demonstrated using collagenase obtained from a culture of human synovial fibroblasts according to the method of Dayer J-M et al., Proc. Natl. Acad. Sci. USA (1976), 73, 945, following activation of the procollagenase in the conditioned medium by treatment with trypsin. Collagenase activity was measured using $^{14}C$-acetylated collagen type I from rat tail tendons as the substrate and employing the microtitre plate assay method of Johnson-Wint, B, Anal. Biochem. (1980), 104, 175. The $IC_{50}$ is that concentration of a compound or salt of the present invention in the enzyme digestion which reduces substrate cleavage and solubilization to 50% of that achieved by the enzyme alone.

The results obtained in the foregoing test with representative compounds and salts of this invention are compiled in Table I hereinafter:

TABLE I

| Compound of formula I | $IC_{50}$ (nM) |
|---|---|
| A | 4 |
| B | 4 |
| C | 9 |
| D | 2 |
| E | 0.5 |
| F | 0.9 |
| G | 1.9 |
| H | 0.5 |

Compound A: $N^2$-[2(R)-[hydroxycarbamoylmethyl]-4-methylvaleryl]-$N^1$,3-dimethyl-L-valinamide;
Compound B: $N^2$-[2(R or S)-[[[(5-bromo-2,3-dihydro-6-hydroxy)-1,3-dioxo-1H-benz[d,e]isoquinol-2-yl)methyl](hydroxy)-phosphinyl]methyl]-4-methylvaleryl]-$N^1$,3-dimethyl-L-valinamide;
Compound C: $N^2$-[2(R or S)-[[(R)-(amino)[(5-bromo-2,3-dihydro-6-hydroxy-1,3-dioxo-1H-benz[d,e]isoquinol-2-yl)methyl](hydroxy)-phosphinyl]methyl]-4-methylvaleryl]-$N^1$,3-dimethyl-L-valinamide hydrobromide.
Compound D: $N^2$-[2(R or S)-(hydroxycarbamoyl)ethyl]-4-methylvaleryl]-$N^1$,3-dimethylvalinamide.
Compound E: $N^2$-[2(R)-[1(R or S)-(hydroxycarbamoyl)-2-phthalimidoethyl]-4-methylvaleryl]-$N^1$,3-dimethyl-L-valinamide.
Compound F: $N^2$-[2(R)-[1(R or S)-(hydroxycarbamoyl)-4-(methoxy-carbonyl)-butyl]-4-methylvaleryl]-$N^1$,3-dimethyl-L-valinamide.
Compound G: $N^2$-[2(R)-[1(R or S)-(hydroxycarbamoyl)-4-phenylbutyl]-4-methylvaleryl]-$N^1$,3-dimethyl-L-valinamide.
Compound H: $N^2$-[2(R)-[1(R or S)-(hydroxycarbamoyl)-2-succinimidoethyl]-4-methylvaleryl]-$N^1$,3-dimethyl-L-valinamide.

The compounds of formula I and their pharmaceutically acceptable salts can be used as medicaments, for example in the form of pharmaceutical preparations. The pharmaceutical preparations can be administered orally, for example, in the form of tablets, coated tablets, dragees, hard and soft gelatin capsules, solutions, emulsions or suspensions. However, they can also be administered rectally, for example, in the form of suppositories, or parenterally, for example, in the form of injectable solutions.

For the manufacture of pharmaceutical preparations the compounds of formula I and their pharmaceutically acceptable salts can be formulated with therapeutically inert, inorganic or organic carriers. Lactose, maize starch or derivatives thereof, talc, stearic acid or its salts can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, generally required in the case of soft gelatin capsules. Suitable carriers for the manufacture of solutions and syrups are, for example, water, polyols, saccharose, invert sugar, glucose and the like. Suitable carriers for the manufacture of injectable solutions are, for example, water, alcohols, polyols, glycerin, vegetable oils and the like. Natural and hardened oils, waxes, fats, semi-liquid polyols and the like are suitable carriers for the manufactured of suppositories.

The pharmaceutical preparations can also contain pre- servatives, stabilizers, wetting agents, emulsifiers, sweeteners, colorants, flavorants, salts for adjustment of the osmotic pressure, buffers, coating agents or antioxidants.

Medicaments containing a compound of formula I or a pharmaceutically acceptable salt thereof and a therapeutically acceptable carrier as well as a process for the manufacture of such medicaments are also objects of the present invention. This process comprises bringing a compound of formula I or a pharmaceutically acceptable salt thereof into a galenical administration form together with a therapeutically inert carrier material and, if desired, one or more other therapeutically active substances.

The compounds of formula I and their pharmaceutically acceptable salts can be used in the control or prevention of illnesses, especially in the control or prevention of degenerative joint diseases or in the treatment of invasive tumors, atherosclerosis or multiple sclerosis. The dosage can vary within wide limits and will, of course, be adjusted to the individual requirements in each particular case. In general, in the case of administration to adults, a daily dosage of from about 5 mg to about 30 mg, preferably from about 10 mg to about 15 mg, should be appropriate, although the upper limit may be exceeded when this is found to be indicated. The daily dosage can be administered as a single dosage or in divided dosages.

The following Examples illustrate the present invention in more detail. In these Examples all temperatures are given in degrees Celsius.

EXAMPLE 1

A solution of 1.93 g of $N^2$-[2(R)-[benzyloxycarbamoylmethyl]-4-methylvaleryl]-$N^1$,3-dimethyl-L-valinamide in 150 ml of ethanol was hydrogenated in the presence of 590 mg of 5% palladium-on-charcoal for 1.5 hours. The catalyst was removed by filtration and the solution was evaporated to give 1.52 g of $N^2$-[(2(R)-[hydroxycarbamoylmethyl]-4-methylvaleryl]-$N^1$,3-dimethyl-L-valinamide as a white solid: nmr (MeOD): 4.22 (s,1H); 3.0-2.9 (m,1H); 2.73 (s,3H); 2.3 (dd,1H,J=14,8); 2.16 (d,d1H, J=14,6); 1.62-1.42 (m,2H); 1.24-1.13 (m,1H); 0.99 (s,9H); 0.94 (d,3H); 0.88 (d,3H); MS: 316 (M+H)+.

The starting material was prepared as follows:

(i) 3.3 g of 4-tert.butyl 2(R)-isobutyl succinate and 2.1 g of (S)-tert.butylglycine methylamide were dissolved in 50 ml of dimethylformamide and the solution was cooled to 0° C. 2.66 g of hydroxybenzotriazole and 3.25 g of N,N'-dicyclohexylcarbodiimide were added. The mixture was allowed to warm to room temperature and was stirred overnight. Dicyclohexylurea was removed by filtration and the mixture was evaporated to a pale orange colored oil which was dissolved in dichloromethane. The organic phase was washed with 5% citric acid solution, 5% sodium bicarbonate solution and saturated sodium chloride solution and then dried over anhydrous magnesium sulphate. The solvent was removed by evaporation to give an orange colored foam. Purification by flash chromatography on silica gel using 3% methanol/dichloromethane for the elution gave 4.49 g of $N^2$-[2(R)-[tertbutoxycarbonylmethyl]-4-methylvaleryl]-$N^1$,3-dimethyl-L-valinamide as a white foam; nmr (CDCl$_3$) 6.55-6.48 (m,2H); 4.32 (d,1H,J=10); 2.8 (d,3H,J=5); 2.76-2.65 (m,1H); 2.58 (d,d,1H,J=15,10); 2.34 (d,d,1H,J=15.5); 1.6-1.45 (m,2H); 1.43 (s,9H); 1.3-1.27 (m,1H); 1.0 (s,9H); 0.9 (d,3H,J=5) 0.86 (d,3H,J=5).

(ii) $N^2$-[2(R)-[tertbutoxycarbonylmethyl-4-methyl]-valeryl]-$N^1$,3-dimethyl-L-valinamide were dissolved in 7 ml of glacial acetic acid and treated with 10.5 ml of a solution of 4M hydrogen bromide in glacial acetic acid. After stirring at room temperature for 1.5 hours, the mixture was evaporated and the resulting gum was re-evaporated three times from 100 ml of toluene each time. The residue was dissolved in diethyl ether and extracted twice with 5% sodium bicarbonate solution. The aqueous extracts were acidified to pH 2 with hydrochloric acid and extracted twice with dichloromethane. The combined organic extracts were dried over anhydrous magnesium sulfate and evaporated to give 3.26 g of a crude white foam containing $N^2$-[2(R)-[carboxymethyl]-4-methylvaleryl]-$N^1$,3-dimethyl-L-valinamide.

(iii) 2.4 g of the foregoing white foam were dissolved in 60 ml of dry dichloromethane and the solution was cooled to 0°. 0.65 ml of pyridine and 3.38 g of di(1-benzotriazolyl) carbonate were then added in succession. The mixture was stirred at 0° for 1 hour and then 1.18 g of O-benzylhydroxylamine were added. The solution was allowed to warm to room temperature and was stirred overnight. The mixture was extracted three times with 5% sodium bicarbonate solution, 2M hydrochloric acid and saturated sodium chloride solution. The organic phase was dried over anhydrous magnesium sulfate and evaporated to give a white foam. Purification by flash chromatography on silica gel using 2% methanol/dichloromethane for the elution gave 2.26 g of $N^2$-[2(R)-[benzyloxycarbamoylmethyl]-4-methylvaleryl]-$N^1$,3-dimethylvalinamide as a white foam; nmr (CDCl$_3$): 9.3 (s,1H); 7.35 (s,5H); 6.78 (d,1H,J=8); 6.28 (br.s,1H); 4.86 (s,2H); 4.24 (d,1H,J=8); 3.0–2.8 (m,1H); 2.76 (d,3H,J=5); 2.42–2.14 (m,2H); 1.56–1.42 (m,2H); 1.27–1.15 (m,1H); 0.99 (s,9H); 0.88 (d,3H,J=6); 0.85 (d,3H,J=6); MS: 406 (M+H)+.

EXAMPLE 2

In a manner analogous to that described in the first paragraph of Example 1, from 300 mg of $N^2$-[2(R or S)-[1(S)-(benzyloxycarbamoyl)ethyl]-4-methylvaleryl]-$N^1$,3-dimethyl-L-valinamide, isomer 1, there were obtained 230 mg of $N^2$-[2(R or S)-[1(S)-hydroxycarbamoyl)ethyl]-4-methylvaleryl-$N^1$,3-dimethylvalinamide, isomer 1, as an off-white solid and from 300 mg of $N^2$-[2(R or S)-[1(S)-(benzyloxycarbamoyl)ethyl]-4-methylvaleryl]-$N^1$,3-dimethyl-L-valinamide, isomer 2, there were obtained 215 mg of $N^2$-[2(R or S)-[1(S)-(hydroxycarbamoyl-ethyl]-4-methylvaleryl]-$N^1$,3-dimethyl-L-valinamide, isomer 2, as an off-white solid.

The nuclear magnetic resonance and mass spectrum data for these isomers are as follows:

Isomer 1:
Nmr (CD$_3$OD): 4.1 (s,1H); 2.75–2.64 (m,4H); 2.36–2.27 (m,1H); 1.65–1.42 (m,2H); 1.32–1.12 (m,4H); 1.02 (s,9H); 0.95 (d,3H,J=5); 0.9 (d,3H,J=5); MS: 330 (M+H)+.

Isomer 2
Nmr (CD$_3$OD); 4.27 (s,1H); 2.72–2.62 (m,4H); 2.32–2.2 (m,1H); 1.58–1.45 (m,1H); 1.43–1.28 (m,1H); 1.13–1.05 (m,4H); 1.02 (s,9H); 0.89 (d,3HJ=5); 0.83 (d,3H,J=5); MS: 330 (M=H)+.

The starting materials were prepared as follows:

(i) 18.78 g of trifluoromethanesulphonic anhydride were added dropwise to a stirred solution of benzyl (S)-lactate and 3.51 g of pyridine in 190 ml of dichloromethane at 0°. The mixture was stirred at 0° for a further 2.5 hours, then washed with water and with saturated sodium chloride solution, dried over anhydrous magnesium sulfate and reduced in volume to 100 ml. This solution was added dropwise to a stirred solution of 9.6 g of di-tert.butyl malonate and 1.33 g of 80% sodium hydride in 110 ml of dimethylformamide at 0°. The mixture was stirred at room temperature for 72 hours. The solvent was removed by evaporation and the residue was dissolved in ethyl acetate. The solution was washed with 5% sodium bicarbonate solution, water and saturated sodium chloride solution, dried over anhydrous magnesium sulfate and evaporated to an oil. Purification by flash chromatography on silica gel using 5% ethyl acetate/n- hexane for the elution gave 9.75 g of 1-benzyl-3-tert.butoxy-carbonyl-4-tert.butyl-2(S)-methylsuccinate as a yellow oil, nmr (CDCl$_3$): 7.38–7.34 (m,5H); 5.15 (dd,2H,J=20,15); 3.55 (d,1H,J=15); 3.17–3.07 (m,1H); 1.45 (s,9H); 1.43 (s,9H); 1.23 (d,3H,J=7); MS: 379 (M+H)+.

(ii) 1.16 g of 80% sodium hydride were added to a stirred solution of 9.72 g of 1-benzyl-3-tert.butoxycarbonyl-4-tert.butyl-2(S)-methylsuccinate in 75 ml of dimethylformamide. After the effervescence had ceased 7.09 g of isobutyl iodide were added and the solution was stirred at 80° for 5 hours. The solvent was removed by evaporation and the residue was dissolved in ethyl acetate. The mixture was washed with 5% sodium bicarbonate solution, water and saturated sodium chloride solution, dried over anhydrous magnesium sulfate and evaporated to an oil. Purification by flash chromatography on silica gel gave 4.9 g of 1-benzyl-4-tert.butyl-3-tert.butoxy-carbonyl-3-isobutyl-2(S)-methylsuccinate as an oil; nmr (CDCl$_3$): 7.38–7.30 (m,5H); 5.14 (d,d,2H,J=20.12); 3.16 (q,1H,J=7); 1.92–1.7 (m,3H); 1.45 (s,18H), 1.34 (d,3H,J=7); 0.9 (d,3H,J=6); 0.86 (d,3H,J=6); MS: 435 (M+H)+.

(iii) 6.67 g of 1-benzyl-4-tert.butyl-3-tert.butoxycarbonyl-3- isobutyl-2(S)-methylsuccinate were stirred with 40 ml of trifluoroacetic acid for 2 hours, the mixture was evaporated and the residue was dissolved in toluene and heated under reflux for 3 hours. The solvent was removed by evaporation to give 4.2 g of 1-benzyl-3(RS)-isobutyl-2(S)-methylsuccinate as a yellow oil; Rf 0.83.

(iv) In a manner analogous to that described in Examples 1(i)–(ii), from 5.3 g of 1-benzyl-3-(RS)-isobutyl-2(S)-methylsuccinate there were obtained 2.4 g of $N^2$-[2(RS)-[1(S)-(benzyloxy-carbamoyl)ethyl]-4-methyl-valeryl]-$N^1$,3-dimethyl-L-valinamide as a mixture of diastereoisomers.

The isomers were separated by preparative HPLC on a Dynamax 60A column using 10% isopropanol in n-hexane as the mobile phase and a flow rate of 15 ml/minute. There were obtained 908 mg of isomer 1 (retention time 14 minutes) and 300 mg of isomer 2 (retention time 17 minutes).

The nuclear magnetic resonance and mass spectrum data for these isomers are as follows:

Isomer 1:
Nmr (CDCl$_3$): 9.63 (br.s,1H); 7.43–7.30 (m,5H); 6.45–6.30 (m,2H); 4.35 (br.s,2H); 4.12 (d,1H,J=8); 2.66 (d,3H,J=5); 2.58–2.48 (m,1H); 2.43–2.30 (m,1H); 1.65–1.48 (m,2H); 1.3–1.2 (m,1H); 1.16 (d,3H,J=7); 1.02 (s,9H; 0.96–0.88 (m,6H); MS: 420 (M+H)+.

Isomer 2:
Nmr (CDCl$_3$): 9.43 (s,1H); 7.43–7.32 (m,5H); 6.85 (d,1H,J=9); 6.5 (br q,1H,J=4); 4.93 (s,2H); 4.3 (d,1H,J=9); 2.74 (d,3H,J=4); 2.72–2.63 (m,1H);

2.43–2.33 (m,1H); 1.57–1.32 (m,2H); 1.18–1.05 (m,4H); 1.01 (s,9H); 0.85 (d,3H,J=7); 0.8(d,3H,J=7); MS: 420 (M+H)+.

EXAMPLE 3

A mixture of 132 mg of $N^2$-[2(R or S)-[[(RS)-(ethoxy)-[(5-bromo-2,3-dihydro-6-hydroxy-1,3-dioxo-1H-benz[d,e]isoquinol-2-yl)methyl]phosphinyl]methyl]-4-methylvaleryl]-$N^1$,3-dimethyl-L-valinamide and 2 ml of trifluoroacetic acid in 2 ml of dry dichloromethane was stirred at room temperature overnight. The solvent was removed by evaporation and the residue was evaporated twice from a 1:1 mixture of methanol and dichloromethane and then twice from dichloromethane. The residual solid was triturated in dry diethyl ether and dried in vacuo to give 90 mg of $N^2$-[2(R or S)-[[[(5-bromo-2,3-dihydro-6-hydroxy-1,3-dioxo-1H-benz[-d,e]isoquinol-2-yl)methyl](hydroxy)phosphinyl]methyl]-4-methylvaleryl]-$N^1$,3-dimethyl-L-valinamide as a yellow solid; nmr (d$_6$DMSO): 8.68 (d,1H,J=8); 8.52 (d,1H,J=8); 8.49 (s,1H); 7.92–7.83 (m,2H); 7.63 (d,1H,J=10); 4.42 (d,2H,J=8); 4.15 (d,1H,J=10); 3.95–3.05 (br); 2.95–2.8 (m,1H); 2.55 (d,3H,J=4); 2.12–1.98 (m,1H); 1.86–1.73 (m,1H); 1.55–1.32 (m,3H); 0.96–0.75 (m,15H); MS: 624, 626.

The starting material was prepared as follows:

(i) 1.37 g of 2 (R or S)-[[(RS)-(ethoxy)(phthalimidomethyl)phosphinyl]methyl]-4-methylvaleric acid in 20 ml of dichloro- methane were cooled to 0°. 0.29 ml of pyridine and 1.52 g of di(1-benzotriazolyl)-carbonate were then added in succession. The mixture was stirred at 0° for 1 hour and then 0.52 g of (S)-tert-.butylglycine N-methylamide was added. The mixture was allowed to warm to room temperature and was stirred overnight. The solution was diluted with dichloromethane, washed three times with 5% sodium bicarbonate solution, once with 2M hydrochloric acid and once with saturated sodium chloride solution and then dried over anhydrous magnesium sulfate. The solvent was removed by evaporation and the residue was purified by flash chromatography on silica gel using 3% methanol/dichloromethane for the elution to give 952 mg of $N^2$-[2(R or S)-[[(RS)-(ethoxy)phthalimidomethyl)(phosphinyl)]methyl]-4-methylvaleryl]-$N^1$,3-dimethyl-L-valinamide as a white foam; nmr (CDCl$_3$) 7.94–7.72 (m,4H); 6.85–6.55 (m,1H); 6.18–6.0 (m,1H); 4.3–4.05 (m,5H); 2.94–2.76 (m,4H); 2.36–2.13 (m,1H); 2.05–1.85 (m,2H); 1.7–1.58 (m,1H); 1.56–1.46 (m,1H); 1.45–1.26 (m,3H); 1.06–0.85 (m,15H); MS: 508 (M+H)+.

(ii) A solution of 820 mg of $N^2$-[2(R or S)-[[(RS)-(ethoxy)phthalimidomethyl)(phosphinyl)]methyl]-4-methylvaleryl]-$N^1$,3-dimethyl-L-valinamide and 0.23 ml of hydrazine hydrate in 10 ml of ethanol was stirred at room temperature overnight. The solvent was removed by evaporation and the residue was evaporated three times from toluene. The residue was dissolved in a mixture of 10 ml of dichloromethane and 0.4 ml of glacial acetic acid and the solution was stirred at room temperature for 2 hours. The mixture was evaporated and the residue was partitioned between diethyl ether and 5% citric acid solution. The aqueous phase was washed with diethyl ether, neutralized with concentrated ammonia solution and the aqueous phase was extracted twice with dichloromethane The organic extracts were dried over anhydrous magnesium sulfate, evaporated and redissolved in 10 ml of dichloromethane. 0.13 ml of N-ethyl-morpholine and 300 mg of 4-benzyloxy-1,8-naphthoic anhydride were added in succession and the mixture was stirred at room temperature for 2 days. The solution was washed with 2M hydrochloric acid, 5% sodium bicarbonate solution and saturated sodium chloride solution and then dried over anhydrous magnesium sulfate. The solvent was removed by evaporation and the residue was purified by flash chromatography on silica gel using 3% methanol/dichloromethane for the elution to give 433 mg of $N^2$-[2(R or S)-[[(RS)-(ethoxy)[6-benzyloxy-2,3-dihydro-1,3-dioxo-1H-benz[d,e]isoquinol-2-yl)methyl]phosphinyl]methyl]-4-methyl-valeryl]-$N^1$,3-dimethyl-L-valinamide as a yellow solid; nmr (CDCl$_3$): 8.68–8.58 (m,3H); 7.76–7.7 (m,1H); 7.56–7.4 (m,4H); 7.16 (d,d,1H,J=8.4), 7.08 (d,0.6H,J=10); 6.9 (d,0.4H,J=10); 6.23–5.96 (m,1H); 5.4 (s,2H); 4.78–4.7 (m,1H); 4.56–4.48 (m,1H); 4.34–4.15 (m,3H); 3.08–2.85 (m,1H); 2.8 (d,1H,J=5) 2.72 (d,2H, J=5); 2.45–2.28 (m,1H); 2.2–1.95 (m,1H); 1.8–1.66 (m,2H); 1.63–1.4 (m,2H); 1.34 (q,2H,J=6); 1.0 (s,6H); 0.95 (s,3H); 0.92–0.85 (m,6H); MS: 664 (M+H)+.

(iii) A solution of 400 mg of $N^2$-[2(R or S)-[[(RS)-(ethoxy)[6-benzyloxy-2,3-dihydro-1,3-dioxo-1H-benz[-d,e]isoquinol-2-yl)methyl]phosphinyl]methyl]-4-methyl-valeryl]-$N^1$,3-dimethyl-L-valinamide in 40 ml of ethanol was hydrogenated in the presence of 100 mg of a 10% palladium-on-charcoal catalyst. The catalyst was removed by filtration, the filtrate was evaporated and the residue was evaporated twice from toluene to give 334 mg of $N^2$-[2(R or S)-[[(RS)-(ethoxy)[(2,3-dihydro-6-hydroxy-1,3-dioxo-1H-benz[d,e]isoquinol-2-yl)methyl]phosphinyl]methyl]-4-methylvaleryl]-$N^1$,3-dimethyl-L-valinamide as a white solid; nmr (CDCl$_3$): 11.1 (brs,1H); 8.38–8.32 (m,1H); 7.83–7.72 (m,2H); 7.23–6.95 (m,3H); 6.64–6.56 (m,1H); 6.06–5.9 (m,1H); 4.88–4.73 (m,1H); 4.45–4.26 (m,2H); 4.25–4.13 (m,2H); 3.05–2.9 (m,1H); 2.8–2.75 (m,3H); 2.72–2.52 (m,1H); 2.4–2.08 (m,1H). 1.8–1.4 (m,6H); 1.02–0.88 (m,15H); MS: 574 (M+H)+.

(iv) A solution of 300 mg of $N^2$-[2(R or S)-[[(RS)-(ethoxy)[(2,3-dihydro-6-hydroxy-1,3-dioxo-1H-benz[-d,e]isoquinol-2-yl)-methyl]phosphinyl]methyl]-4-methylvaleryl]-$N^1$,3-dimethyl-L-valinamide in 10 ml of dry dichloromethane was cooled to 0° and a solution of 83 mg of bromine in 2 ml of dichloromethane was added. After 10 minutes the solution was washed twice with 5% sodium thiosulphate solution, dried over anhydrous magnesium sulfate and evaporated to give 350 mg of $N^2$-[2(R or S)-[[(RS)-(ethoxy)[(5-bromo-2,3-dihydro-6-hydroxy-1,3-dioxo-1H-benz[d,e]isoquinol-2-yl)methyl]phosphinyl]methyl]-4-methylvaleryl]-$N^1$,3-dimethyl-L-valinamide as a yellow solid; nmr (CDCl$_3$): 10.5–10.2 (br s,1H); 8.5–8.42 (m,1H); 8.3 (d,1H,J=9); 7.53–7.46 (m,1H); 6.95 (d,0.6H,J=8); 6.68 (d,0.4H,J=8); 6.02–5.85 (m,1H); 4.92–4.77 (m,1H); 4.46–4.22 (m,4H); 3.08–2.95 (m,1H); 2.83 (d,3H,J=5); 2.7–2.51 (m,1H); 2.43–2.12 (m,1H); 1.84–1.45 (m,8H,(6H+H$_2$O)); 1.06–0.92 (m,15H); MS: 651, 653.

EXAMPLE 4

In a manner analogous to that described in the first paragraph of Example 3, from 600 mg of $N^2$-[2(R or S)-[[(RS)-(ethoxy)[(2,3-dihydro-6-hydroxy-1,3-dioxo-1H-benz[d,e]-isoquinol-2-yl) methyl]phosphinyl]methyl]-4-methylvaleryl]-$N^1$,3-dimethyl-L-valinamide, prepared as described in Example 3(iii), there were obtained 411 mg of $N^2$-[2(R or S)-[[[(2,3-dihydro-6-hydroxy-1,3-dioxo-1H-benz[d,e]isoquinol-2-yl)methyl]-(hydroxy)-phosphinyl]methyl-4-methylvaleryl]-$N^1$,3- dimethyl-L-valinamide as a yellow foam; nmr (d$_6$DMSO): 11.98 (brs,1H); 8.56 (d,1H,J=8); 8.52 (d,1H,J=8); 8.4 (d, 1H,J=8); 7.9 (q,1H,J=5); 7.8 (t,1H,J=6); 7.63 (d,1H,J=10); 7.18 (d,1H,J=8); 4.44 (d,2H,J=9); 4.15 (d,1H,J=10); 4.10-3.10 (brs); 2.95-2.82 (m,1H); 2.56 (d,3H,J=5); 2.12-2.0 (m,1H); 1.85-1.72 (m,1H); 1.55-1.32 (m,3H); 0.86-0.78 (m,15H); MS: 546 (M+H)$^+$.

EXAMPLE 5

A solution of 550 mg of N$^1$-(N-benzyloxycarbonyl-4-aminobutyl-N$^2$-[2(R or S)-[[(RS)-(ethoxy)-[(2,3-dihydro-1,3-dioxo-1H-benz[d,e]isoquinol-2-yl)methyl]phosphinyl]methyl]-4-methylvaleryl]-3-methyl-L-valinamide in 2 ml of 4M hydrobromic acid in acetic acid was stirred at room temperature for 1 hour. The solvent was removed by evaporation and the residual oil was evaporated from toluene. Methanol and then diethyl ether were added, the precipitate formed was filtered off, washed with diethyl ether and dried in vacuo to give 462 mg of N$^1$-(4-aminobutyl)-N$^2$-[2(R or S)-[[[(2,3-dihydro-1,3-dioxo-1H-benz[d,e]isoquinol-2-yl)methyl](hydroxy)phosphinyl]methyl]-4-methylvaleryl]-3-methyl-L-valinamide hydrobromide as a pale orange colored solid; nmr (d$_6$DMSO): 8.53 (t,4H,J=7); 8.04 (t,1H,J=5); 7.94 (t,2H,J=7); 7.72 (brs,2H); 7.65 (d,1H,J=9): 5.26(brs); 4.48 (d,2H,J=9); 4.15 (d,1H,J=9) 3.15-2.72 (m,5H); 2.16-2.0 (m,1H); 1.9-1.75 (m,1H); 1.58-1.35 (m, 7H); 0.92-0.78 (m,15H). MS: 586 (M+H)$^+$.

The starting material was prepared as follows:

(i) A solution of 5 g of N-(tert.butoxycarbonyl)-tert.butyl glycine and 1.75 ml of pyridine in 100 ml of dry dichloromethane was cooled to 0° and 9.14 g of di-(1-benzotriazolyl)carbonate were added while stirring. After 1 hour a solution of 5.42 g of N$^1$-benzyloxy carbonyl-1,4-diaminobutane and 1.75 ml of pyridine in 10 ml of dichloromethane was added and the mixture was stirred at room temperature overnight. The mixture was washed twice with 5% sodium bicarbonate solution, once with 2M hydrochloric acid and once with water and then dried over anhydrous magnesium sulfate. The solvent was removed by evaporation to give 8.4 g of N$^1$-(4-(benzyloxycarbonylamino)butyl)-N$^2$-(tert.butoxycarbonyl)-3-methylvalinamide as a white foam; nmr (CDCl$_3$): 7.35 (s,5H); 6.38 (br.s,1H); 5.4-5.08 (m,4H); 3.97-3.83 (m,1H); 3.30-3.1 (m, 4H); 1.5 (br.s,4H); 1.42 (s,9H); 0.96 (s,9H); MS: 436 (M+H)$^+$.

(ii) A solution of 1.6 g of N$^1$-(4-(benzyloxycarbonylamino)-butyl)-N$^2$-(tert.butoxycarbonyl)-3-methylvalinamide in 50 ml of 4M hydrochloric acid/ethyl acetate was stirred at room temperature for 2 hours. The solvent was removed by evaporation to give 1.42 g of a white foam which was then reacted with 1.58 g of 2(R or S)-[[(RS)-(ethoxy)[(2,3-dihydro-1,3-dioxo-1H-benz[d,e]isoquinol-2-yl)methyl]phosphinyl]methyl]-4-methylvaleric acid in a manner analogous to that described in Example 3(i) to give 1.54 g of N$^1$-(N-benzyloxy carbonyl-4-aminobutyl)-N$^2$-[2(R or S)-[[(RS)-(ethoxy)[(2,3-dihydro-1,3-dioxo-1H-benz[d,e]isoquinol-2-yl)methyl]phosphinyl]methyl]-4-methylvaleryl]-3-methyl-L-valinamide as a white foam; nmr (CDCl$_3$: 8.64 (d,2H,J=6); 8.27-8.22 (m,2H); 7.82-7.74 (m,2H); 7.38-7.27 (m,5H); 6.77 (d,0.33H,J=9); 6.84 (d,0.66H,J=9); 6.25 (br.s,0.33H); 6.07 (br.s.,0.66H); 5.13-4.95 (m,3H); 4.78-4.67 (m,1H); 4.55-4.43 (m,1H); 4.3-4.06 (m,3H); 3.29-3.07 (m,4H); 3.05-2.8 (m,1H);2.43-2.26 (m,1H); 2.17-1.94 (m,1H); 1.78-1.62 (m,3H); 1.6-1.25 (m,8H); 1.0-0.83 (m,15H); MS: 749 (M+H)$^+$.

EXAMPLE 6

A solution of 300 mg of N$^1$-(4-nitroguanidinobutyl)-N$^2$-[2-(R or S)-[[(RS)-(ethoxy)[(2,3-dihydro-1,3-dioxo-1H-benz[d,e]isoquinol-2-yl)methyl]phosphinyl]methyl]-4-methylvaleryl]-3-methyl-L-valinamide in 20 ml of 80% acetic acid was hydrogenated in the presence of 30 mg of a 10% palladium-on-charcoal catalyst. The catalyst was removed by filtration, the filtrate was evaporated to dryness, the residue was dissolved in 5 ml of dichloromethane and 5 ml of trifluoroacetic acid and the solution was stirred at room temperature overnight. The solvent was removed by evaporation and residue was evaporated twice from 2 ml of methanol and 2 ml of dichloromethane and twice from 2 ml of dichloromethane. The residual solid was triturated with diethyl ether, filtered off and dried in vacuo to give 180 mg of N$^1$-(4-guanidinobutyl)-N$^2$-[2-(R or S)-[[[(2,3-dihydro-1,3-dioxo-1H-benz[d,e]isoquinol-2-yl)methyl]phosphinyl]methyl]-4-methylvaleryl]-3-methyl-L-valinamide trifluoroacetate; nmr d$_6$DMSO): 8.53 (t,4H,J=8) 8.03 (t,1H,J=7); 7.92 (t,2H,J=8); 7.75 (br.s,1H); 7.1 (br.s,3H); 4.42 (d,2H,J=10); 4.07 (d,1H,J=7); 3.14-2.72 (m,5H); 2.12-1.98 (m,1H); 1.85-1.72 (m,1H); 1.6-1.25 (m,8H); 0.95-0.7 (m,15H); MS: 629 (M+H)$^+$.

The starting material was prepared as follows:

(i) A solution of 1 g of N$^1$-(N-benzyloxycarbonyl-4-aminobutyl)methyl valinamide in 10 ml of ethanol was hydrogenated for 1 hour in the presence of 100 mg of a 5% palladium-on-charcoal catalyst. The catalyst was removed by filtration, 342 mg of 3,5-dimethyl-N-nitro-1H-pyrazole-1-carboximidamide were added to the filtrate and the mixture was heated under reflux for 12 hours. The solvent was removed by evaporation and the residue was dissolved in dichloromethane. The solution was washed with 2M hydrochloric acid and 5% sodium bicarbonate solution, dried over anhydrous magnesium sulfate and evaporated to give a white foam. This was purified by flash chromatography on silica gel using 5% methanol/dichloromethane for the elution to give 538 mg of N$^2$-(tertbutoxycarbonyl)-N$^1$-[4-(nitroguanidino)butyl]-3-methylvalinamide as a white foam; nmr (CDCl$_3$): 8.55 (br.s,1H); 7.68 (br.s,2H); 6.66 (br.s,1H); 5.26 (br.s,1H); 3.95 (br.s,1H); 3.55-3.2 (m,4H); 1.66-1.54 (m,4H); 1.43 (s,9H); 1.0 (s,9H); MS: 389 (M+H)$^+$.

(ii) 500 mg of N$^2$-(tertbutoxycarbonyl)-N$^1$-[4-(nitroguanidino)butyl]-3-methylvalinamide were reacted with 554 mg of 2(R or S)-[[(RS)-(ethoxy)[(2,3-dihydro-1,3-dioxo-1H-benz[d,e]isoquinolyl-2-yl)methyl]phosphinyl]methyl]-4-methylvaleric acid in a manner analogous to that described in Example 3(i) to give 322 mg of N$^1$-(4-nitroguanidinobutyl)-N$^2$-[2-(R or S)-[[(RS)-(ethoxy)[(2,3-dihydro-1,3-dioxo-1H-benz[d,e]isoquinol-2-yl)methyl]phosphinyl]methyl]-4-methylvaleryl]-3-methyl-L-valinamide as a white foam; nmr (CDCl$_3$): 8.62 (d,2H,J=7); 8.32-8.25 (m,2H); 7.83-7.75 (m,2H); 7.55 (br,1H); 7.15-6.88 (m,2H); 4.84-4.72 (m,1H); 4.52-4.4 (m,1H); 4.3-4.15 (m,3H); 3.48 (q,2H,J=7); 3.3-2.8 (m,3H); 2.5-2.22 (m,2H); 1.6-1.18 (m,14H); 1.02-0.8 (m,15H); MS: 702 (M+H)$^+$.

EXAMPLE 7

A solution of 500 mg of [N$^2$-[2(R or S)-[[(RS)(ethoxy)[5-tert.butoxycarbonylamino-1-(RS)-(2,3-dihydro-1H-benz[d,e]-isoquinolin-2-yl)pentyl]phosphinyl]methyl]-4-methylvaleryl]-$N^1$,3-dimethyl-L-valinamide in 1 ml of glacial acetic acid and 4 ml of 45% hydrogen bromide in glacial acetic acid was stirred at room temperature for 4 hours. The solvent was removed by evaporation and the residue was evaporated twice from toluene to give a pale yellow powder as a mixture of diastereoisomers. The diastereoisomers were separated by reverse phase preparative HPLC on a Sphensorb S5 column using 50% methanol/0.05M ammonium formate at a flow rate of 8 ml/min. as the mobile phase to give:

(i) 78 mg of $N^2$-[2(R or S)-[[[5-amino-1(R or S)-(2,3-dihydro-1H-benz[d,e]isoquinolin-2-yl)pentyl](hydroxy)phosphinyl]methyl]-4-methylvaleryl]-$N^1$,3-dimethyl-L-valinamide, isomer 1; retention time 22 min.; nmr (CD$_3$OD): 8.56 (d,1H, J=6); 8.50 (d,1H,J=6); 8.32 (t,2H,J=7); 7.81 (t,1H,J=7); 7.73 (t,1H,J=7); 5.36–5.25 (m,1H); 4.16 (s,1H); 3.02–2.82 (m,3H); 2.7 (s,3H); 2.48–2.33 (m,1H); 2.2–1.98 (m,3H); 1.78–1.64 (m,3H); 1.60–1.35 (m,4H); 0.97 (s,9H); 0.9 (d,3H,J=6); 0.85 (d,3H,J=6) MS: 601 (M+H)+; and (ii) 70 mg of $N^2$-[2(R or S)-[[[5-amino-1(R or S)-(2,3-dihydro-1H-benz[d,e]isoquinolin-2-yl)pentyl](hydroxy)phosphinyl]methyl]-4-methylvaleryl]-$N^1$,3-dimethyl-L-valinamide, isomer 2: retention time=34 min.; nmr (CD$_3$OD): 8.58 (d,2H,J=7); 8.36–8.29 (m,2H); 7.85–7.75 (m,2H); 5.4–5.26 (m,1H); 4.18 (s,1H); 2.96–2.84 (m,3H); 2.68 (s,3H); 2.47–2.32 (m,2H); 2.19–2.04 (m,1H); 1.92–1.65 (m,4H); 1.63–1.37 (m,4H); 1.01 (s,9H); 0.87 (t,6H,J=6); MS: 601 (M+H)+.

The starting material was prepared as follows:

(i) A solution of 11.7 g of benzyl 2(R or S)-[(ethoxyphosphinyl)methyl]-4-methylvalerate and 13.0 g of 5-pthalimido-pentan-1-al in 100 ml of toluene was treated with 4.7 ml of 1,1,3,3-tetramethylguanidine and the mixture was stirred at room temperature for 12 hours. The solvent was removed by evaporation and the residue was purified by flash chromatography on silica gel using ethyl acetate/n-hexane (2:1) for the elution to give 8.8 g of a white foam. This foam was dissolved in 150 ml of ethanol, 2.36 ml of hydrazine hydrate were added and the mixture was stirred at room temperature overnight. The solvent was removed by evaporation and the residue was dissolved in dichloromethane. 5 ml of glacial acetic acid were added and the mixture was stirred at room temperature for 1 hour. The mixture was then filtered, evaporated to dryness and the residue was partitioned between diethyl ether and 2M hydrochloric acid. The aqueous phase was made basic with concentrated ammonia solution and extracted three times with dichloromethane. The combined extracts were dried over anhydrous magnesium sulfate, evaporated and redissolved in 100 ml of dioxan and 100 ml of water. 2.49 g of sodium bicarbonate and then 3.87 g of di-tert.butyl dicarbonate were added and the mixture was stirred at room temperature overnight. The solvent was removed by evaporation and the residue was partitioned between water and ethyl acetate. The organic phase was washed with 5% citric acid solution, dried over anhydrous magnesium sulfate, evaporated and redissolved in 100 ml of dry dichloromethane. The solution was cooled to 0° C. and treated with 10.93 ml of pyridine and then dropwise with 1.58 ml of methanesulphonyl chloride. The mixture obtained was stirred at 0° C. for 2 hours and then at room temperature overnight. The solvent was removed by evaporation and the residue was purified by flash chromatography on silica gel using ethyl acetate/n-hexane (3:1) for the elution to give 5.5 g of benzyl(2-(R or S)-[[(RS)-(ethoxy)[1(RS)-methanesulphonyloxy-5-(tert.butylcarbonylamino)pentyl]phosphinyl]methyl]-4-methylvalerate as a white foam.

The foregoing benzyl ester was dissolved in 100 ml of dimethylformamide and 1.21 g of sodium azide were added to the solution. The mixture was heated at 70° C. for 48 hours, the solvent was removed by evaporation and the residue was dissolved in 50 ml of dichloromethane. The organic layer was washed with 50 ml of sodium bicarbonate solution and with 50 ml of saturated sodium chloride solution, dried over anhydrous magnesium sulfate and evaporated to give a yellow oil. Purification by flash chromatography on silica gel using ethyl acetate/n-hexane (3:1) for the elution gave 3.65 g of benzyl 2(R or S)-[[(RS)-(ethoxy)[1-(RS)-azido-5-tert.butoxycarbonylaminopentyl]phosphinyl]methyl]-4-methylvalerate as a off-white foam; nmr (CDCl$_3$): 7.37 (s,5H); 5.2–5.1 (m,2H); 4.56 (brs,1H); 4.17–4.03 (m,2.5H); 3.43–3.33 (m,0.5H); 3.25–3.05 (m,2H); 3.02–2.87 (m,1H); 2.39–2.15 (m,1H); 1.98–1.75 (m,2H); 1.7–1.23 (m,20H); 0.92 (d,3H,J=6); 0.87 (d,3H,J=6); MS: 539 (M+H)+.

(ii) 2.04 ml of 1,3-propanedithiol were added dropwise to a stirred solution of 3.65 g of benzyl 2(R or S)-[[(RS)-(ethoxy)[1-(RS)-azido-5-tert.butoxycarbonylaminopentyl]phosphinyl]methyl]-4-methylvalerate and 2.83 ml of triethylamine in 80 ml of methanol. The mixture was stirred at room temperature overnight, the solvent was removed by evaporation and the residue was purified by flash chromatography on silica gel using 4% methanol/dichloromethane for the elution to give 3.25 g of benzyl 2(R or S)-[[(RS)-(ethoxy)[1-(RS)-amino-5-tert.butoxy carbonylaminopentyl]phosphinyl]methyl]-4-methylvalerate as an off-white foam; nmr (CDCl$_3$): 7.36 (s,5H); 5.2–5.08 (m,2H); 4.6 (brs,1H); 4.2–3.98 (m,2H); 3.17–3.08 (m,2H); 3.0–2.76 (m,2H); 2.4–2.13 (m,1H): 2.0–1.25 (m,25H); 0.98–0.86 (m,6H); MS: 513 (M+H)+.

(iii) A solution of 3.25 g of benzyl 2-(R or S)-[[(RS)-(ethoxy)[1-(RS)-amino-5-tert.butoxycarbonylaminopentyl]phosphinyl]methyl]-4-methylvalerate and 1.52 g of 1,8-naphthalic anhydride in 50 ml of dimethylformamide was treated with 0.96 ml of 1,1,3,3-tetramethylguanidine. The mixture was heated at 50° C. for 48 hours, the solvent was removed by evaporation and the residue was dissolved in dichloromethane. The solution was washed with 2M hydrochloric acid, 5% sodium bicarbonate solution and saturated sodium chloride solution, dried over anhydrous magnesium sulfate and evaporated to give a yellow gum. Purification by flash chromatography on silica gel using 2% methanol/dichloromethane for the elution gave 1.78 g of benzyl 2-(R or S)-[[(ethoxy)[5-tert.butoxycarbonylamino-1-(RS)-(2,3-dihydro-1H-benz[d,e]isoquinolin-2-yl)pentyl]phosphinyl]methyl]-4-methylvalerate as a yellow foam.

The foregoing benzyl ester was dissolved in 20 ml of isopropanol and the solution was hydrogenated in the presence of 300 mg of 10% palladium-on-charcoal. The catalyst was removed by filtration, and the filtrate was evaporated and the residue was dissolved in dry dichloromethane and cooled to 0° C. The solution was treated with 0.2 ml of pyridine and then with 1.09 g of di-(1-benzotriazolyl)carbonate. The mixture was stirred at 0° C. for 1 hour and then a solution of 0.4 g of $N^1$,3-dimethyl-L-valinamide in 1 ml of dichloromethane was added. The mixture was stirred at 0° C. for 2 hours and then at room temperature overnight. The mixture was diluted with dichloromethane, washed three times with 5% sodium bicarbonate solution, dried over anhydrous magnesium sulfate and evaporated to give a yellow foam. Purification by flash chromatography on silica gel using 3% methanol/dichloromethane for the elution gave 1.12 g of [N$^2$-[2(R or S)-(ethoxy)[5-tert.-butoxycarbonylamino-1-(RS)-(2,3-dihydro-1H-benz[d,e]isoquinolin-2-yl)pentyl]phosphinyl]methyl]-4-methylvaleryl]-N$^1$,3-dimethyl-L-valinamide as a pale yellow foam; nmr (CDCl$_3$): 8.66–8.46 (m,2H); 8.3–8.22 (m,2H); 7.83–7.72 (m,2H); 7.12–6.73 (m,1H); 6.28–6.17 (m,1H) 5.68–5.4 (m,1H); 4.6–4.48 (m,1H); 4.3–4.06 (m,3H); 3.1–2.96 (m,2H); 2.93–2.73 (m,4H); 2.6–2.04 (m,3H); 1.78–1.3 (m,18H); 1.28–0.82 (m,15H); MS: 729 (M+H)$^+$.

EXAMPLE 8

In a manner analogous to that described in the first paragraph of Example 3, from 120 mg of N$^2$-[2(R or S)-[[(RS)-(ethoxy)[1(RS)-(2,3-dihydro-1H -benz[d,e]isoquinolin-2yl)-2-hydroxyethyl] phosphinyl]methyl]-4-methylvaleryl]-N$^1$,3-dimethyl-L-valinamide there were obtained 105 mg of N$^2$-[2(R or S)-[[[1(RS)-(2,3-dihydro-1H-benz[d,e]isoquinolin-2-yl)-2-hydroxyethyl](hydroxy)phosphinyl]methyl]-4-methylvaleryl]-N$^1$,3-dimethyl-L-valinamide as a 2:1 mixture of diastereoisomers as a white foam; nmr (CD$_3$OD): 8.78–8.66 (m,2H); 8.43–8.35 (m,2H); 7.90–7.8 (m,2H); 5.93–5.8 (m,0.5H); 5.72–5.6 (m,0.5H); 5.15–5.06 (m,1H); 4.32–4.13 (m,2H); 3.13–2.9 (m,1H); 2.72 (s,3H); 2.64–1.95 (m,3H); 1.72–1.37 (m,3H); 1.05–0.84 (s,15H); MS: 558 (M−H)$^-$.

The starting material was prepared as follows:

In a manner analogous to that described in Example 7(i)–(iii), from 1-diphenyltert.butylsilyloxy)ethan-1-al there was obtained N$^2$-[2(R or S)-[[(RS)-(ethoxy)[1(RS)-(2,3-dihydro-1H-benz[d,e]isoquinolin-2-yl)-2-hydroxyethyl]phosphinyl]methyl]-4-methylvaleryl]-N$^1$,3-dimethyl-L-valinamide as a white foam; nmr (CDCl$_3$): 8.66–8.58 (m,2H); 8.3–8.23 (m,2H); 7.83–7.75 (m,2H); 6.99–6.8 (m,1H); 6.11–5.9 (m,1H); 5.8–5.57 (m,1H); 4.58–4.35 (m,1H); 4.32–4.05 (m,4H); 3.52 (brs,0.5H); 3.16 (brs,0.5H); 2.96–2.72 (m,4H); 2.7–2.3 (m,2H); 2.25–1.92 (m,1H); 1.55–1.23 (m,5H); 1.05–0.82 (m,15H); MS: 588 (M+H)$^+$.

EXAMPLE 9

In a manner analogous to that described in the first paragraph of Example 7, from 250 mg of N$^2$-[2(R or S)-[[(RS)-(ethoxy)[3-tert.butoxycarbonylamino-1(RS)-(2,3-dihydro-1,3-dioxo-1H-benz[d,e]isoquinol-2-yl)propyl]phosphinyl]methyl]-4-methylvaleryl]-N$^1$,3-dimethyl-L-valinamide there were obtained 205 mg of N$^2$-[2(R or S)-[[[3-amino-1(RS)-(2,3-dihydro-1,3-dioxo-1H-benz[d,e]isoquinol-2-yl)propyl](hydroxy)phosphinyl]methyl]-4-methylvaleryl]-N$^1$,3-dimethyl-L-valinamide as a 1:1 mixture of diastereoisomers as a white foam; nmr (CD$_3$OD): 8.55 (t,2H,J=7); 8.34 (d,2H,J=7); 7.82–7.74 (M,2H); 5.42–5.26 (m,1H); 4.34 (d,1H,J=5); 3.02–2.85 (m,3H); 2.63–2.44 (m,5H); 2.42–2.14 (m,2H); 2.01–1.98 (m,1H); 1.65–1.3 (m,3H); 0.95–0.76 (m,15H); MS: 573 (M+H)$^+$.

In a manner analogous to that described in Example 7(i)–iii, from 3-(tert.butoxycarbonylamino)-propan-1-al there was obtained N$^2$-[2(R or S)-[[(RS)-(ethoxy)[3-tert.butoxycarbonyl-amino-1(RS)-(2,3)-dihydro-1,3-dioxo-1H-benz[d,e]isoquinol-2-yl)propyl]phosphinyl]methyl]-4-methylvaleryl]-N$^1$,3-dimethyl-L-valinamide as a 1:1 mixture of diastereoisomers as a white foam; nmr (CDCl$_3$): 8.63–8.56 (m,2H); 8.3–8.22 (m,2H); 7.85–7.74 (m,2H); 7.07 (d,0.5H,J=9); 6.92 (d,0.5H,J=9); 6.71 (br. q,0.5H,J=4); 6.17 (br.q,0.5H,J=4); 5.57–5.4 (m,1H); 5.2 (br.t,1H,J=5); 4.3–4.07 (m,3H); 3.49 (br.s,1H); 3.02–2.46 (m,5H); 2.4–2.22 (m,1H); 2.18–2.06 (m,1H); 1.89–1.56 (m,4H); 1.46–1.32 (m,12H); 1.06–0.86 (m,15H); MS: 701 (M+H)$^+$.

EXAMPLE 10

A mixture of 0.276 g of [2(R or S)-[(R)-(benzyloxyformamido)[[(2,3-dihydro-1,3-dioxo-1H-benz[d,e]isoquinol-2-yl)methyl](hydroxy)phosphinyl]methyl]-4-methylvaleric acid and 0.144 g of L-2-(tert.butyl)glycine methylamide in 25 ml of toluene was heated under reflux (bath temperature 140° C.) in a nitrogen atmosphere for 7 hours. The solvent was removed by evaporation and the residue was dissolved in 15 ml of dichloromethane containing 0.3 g of trifluoroacetic acid and re-evaporated. After two further evaporations from 10 ml of ethanol the residue was dissolved in 4 ml of ethanol and the product was precipitated by the gradual addition of 10 ml of water. There was obtained 0.26 g of N$^2$-[2(R or S)-[(R)-(benzyloxyformamido)[[(2,3-dihydro-1,3-dioxo-1H-benz[d,e]isoquinol-2-yl)methyl](hydroxy)phosphinyl]methyl]-4-methylvaleryl]-N$^1$,3-dimethyl-L-valinamide in the form of a white solid: MS: 679 (M+H)$^+$.

The starting material was prepared as follows:

(i) A mixture of 19.8 g of crystalline hypophosphorous acid and 36 g of trimethyl orthoformate was stirred at room temperature under a nitrogen atmosphere for 1.5 hours. 27.6 g of diethyl acetamidomethylenemalonate were added to the solution and the mixture was cooled to 0° C. Then, a solution of 11.5 g of 1,1,3,3-tetramethylguanidine in 20 ml of dichloromethane was added while maintaining the temperature at 0°–10° C. After completion of the addition, the mixture was stirred at room temperature for 3 hours, then diluted with dichloromethane and poured on to a mixture of 250 ml of 2M hydrochloric acid and ice. The organic phase was separated and the aqueous phase was extracted three times with dichloromethane. The organic solutions were combined and evaporated to give 40 g of a pale yellow oil which was dissolved in a mixture of 70 ml of dichloromethane and 60 ml of trifluoroacetic acid. The solution was left to stand at room temperature for 24 hours and was then evaporated. Toluene was added to the residue and the solution obtained was evaporated. The residue was dissolved in ether and left to crystallize for 24 hours. The solid was filtered off and dried in vacuo to give 29.34 g of diethyl 2-[(acetamido)(hydroxyphosphinyl)methyl]malonate in the form of a white solid of m.p. 113°–114° C.

(ii) 12.0 g of diethyl 2-[(acetamido)(hydroxyphosphinyl)methyl]malonate were dissolved in 100 ml of dry dimethyl sulphoxide and the solution was cooled to 10° C. while stirring under a nitrogen atmosphere. 3.2 g of 60% sodium hydride in mineral oil were added, the mixture was stirred at room temperature for 2 hours and then 8 g of isobutyl iodide were added. The mixture was stirred at room temperature in the dark for 20 hours and 20 ml of glacial acetic acid were added. The volatiles were removed by evaporation in a high vacuum and the resulting semi-solid residue was dissolved in 100 ml of water containing 15 ml of 50% hypophosphorous acid. The solution was extracted eight times with ethyl acetate and the combined extracts were dried over sodium sulfate and evaporated. The residue was dissolved in dichloromethane and the solution was washed in sequence with water and saturated sodium chloride solution. The dichloromethane solution was dried over sodium sulfate and evaporated, and the residue was crystallized from diethyl ether/n-hexane to give 6.28 g of diethyl 2-[(acetamido)-(hydroxyphosphinyl)methyl]-2-isobutylmalonate in the form of a white solid; MS: 352 $(M+H)^+$.

The combined water and sodium chloride washings from the foregoing paragraph were extracted with dichloromethane to give, after evaporation of the solvent and crystallization of the residue from diethyl ether/n-hexane, a further 1.68 g of product.

(iii) 1.5 g of S-(−)-α-methylbenzylamine and 0.2 g of water were added to a stirred suspension of 3.51 g of diethyl 2-[(acetamido)(hydroxyphosphinyl)methyl]-2-isobutylmalonate in 50 ml of diethyl ether. The mixture was stirred and left to crystallize for 4 hours. The white solid was collected and recrystallized from 50 ml of ethyl acetate containing 0.2 g of water. There were obtained 1.7 g of diethyl 2-[(R)-acetamido)(hydroxyphosphinyl)methyl]-2-isobutylmalonate 1(S)-phenylethylamine salt in the form of white crystals of melting point 108°–110° C.; $[\alpha]_{589}^{20} = -13.3°$ (c=0.5% in methanol).

A suspension of 15 g of the foregoing salt in 150 ml of ethyl acetate was shaken with 200 ml of a 4% aqueous sodium hydrogen carbonate solution until all of the solid had dissolved. The aqueous phase was separated and the ethyl acetate phase was extracted twice with 4% aqueous sodium hydrogen carbonate solution. The combined aqueous extracts were acidified with concentrated hydrochloric acid to a pH below 1 and extracted eight times with dichloromethane. The combined extracts were dried over anhydrous sodium sulfate and evaporated to give a colorless gum which was crystallized from diethyl ether/n-hexane. After 2 hours the solid was collected and dried to give 10.1 g of diethyl 2-[(R)-(acetamido)(hydroxyphosphinyl)methyl]-2-isobutylmalonate in the form of white crystals of melting point 105°–106° C.; $[\alpha]_{589}^{20} = -8.1°$ (c=0.5% in methanol).

(iv) A mixture of 0.58 g of N-bromomethyl-1,8-naphthalimide and 0.7 g of diethyl 2-[(R)-(acetamido)(hydroxyphosphinyl)methyl]-2-isobutylmalonate in 20 ml of dry chloroform was treated with 10 ml of 1,1,1,3,3,3-hexamethyldisilazine and 10 ml of bis(trimethylsilyl)acetamide. The mixture was stirred at 50° C. for 20 hours under a nitrogen atmosphere, cooled and poured into a mixture of 2M hydrochloric acid and ice. After shaking the chloroform phase was separated and the aqueous phase was extracted twice with chloroform. The extracts were combined, dried over magnesium sulfate and evaporated to give a residue which was purified by chromatography on silica gel using dichloromethane/methanol/acetic acid/water (240:24:3:2) for the elution. After crystallization of the product from ethyl acetate there was obtained 0.64 g of diethyl 2-[(R)-(acetamido)[[(2,3-dihydro-1,3-dioxo-1H-benz[d,e]isoquinol-2-yl)methyl](hydroxy)phosphinyl]-methyl]-2-isobutylmalonate in the form of an off-white powder of melting point 202°–203° C.

(v) 2.8 g of diethyl 2-[(R)-(acetamido)[[(2,3-dihydro-1,3-dioxo-1H-benz[d,e]isoquinol-2-yl)methyl](hydroxy)phosphinyl]methyl]-2-isobutylmalonate were dissolved in 25 ml of dimethyl sulphoxide containing 0.09 g of water and 0.88 g of lithium chloride. The mixture was heated at 180° C. while stirring under a nitrogen atmosphere for 3.5 hours. After cooling, the mixture was poured into 150 ml of 2M hydrochloric acid and extracted four times with dichloromethane. The combined extracts were washed twice with water, dried over magnesium sulfate and evaporated to give an orange colored foam which was chromatographed on silica gel using dichloromethane/methanol/acetic acid/water (120:15:3:2) for the elution. There were obtained 2.03 g of ethyl 2(R or S)-[(R)-(acetamido)[[(2,3-dihydro-1,3-dioxo-1H-benz[d,e]isoquinol-2-yl)methyl](hydroxy)phosphinyl]methyl]-4-methylvalerate which was dissolved in a mixture of 27 ml of acetic acid, 24.5 ml of concentrated hydrochloric acid and 16 ml of water. The solution was heated under reflux for 8 hours, cooled and evaporated. The residue was evaporated several times in the presence of 10% methanol in toluene and the residue obtained was triturated with acetonitrile. There were obtained 1.6 g of 2(R or S)-[(R)-(amino)[[(2,3-dihydro-1,3-dioxo-1H-benz[d,e]isoquinol-2-yl)methyl](hydroxy)phosphinyl]methyl]-4-methylvaleric acid which was suspended in a mixture of 120 ml of water and 20 ml of tetrahydrofuran. 3.4 g of potassium carbonate and 2.34 ml of benzyl chloroformate were added and the mixture was stirred at room temperature under a nitrogen atmosphere for 20 hours. 100 ml of 10% methanol in dichloromethane were added and the pH of the aqueous layer was adjusted to less than 1 by the addition of concentrated hydrochloric acid. The organic phase was separated and the aqueous phase was extracted three times with dichloromethane. The combined organic solutions were washed with water, dried over magnesium sulfate and evaporated to give a brown residue which was crystallized from ethyl acetate/diethyl ether. There were obtained 1.2 g of 2(R or S)-[(R)-(benzyloxyformamido)[[(2,3-dihydro-1,3-dioxo-1H-benz[d,e]isoquinol-2-yl) methyl](hydroxy)phosphinyl]methyl]-4-methylvaleric acid in the form of an off-white solid; MS: 553 $(M+H)^+$.

EXAMPLE 11

A suspension of 0.6 g of $N^2$-[2(R or S)-[(R)-(benzyloxyformamido)[[(2,3-dihydro-1,3-dioxo-1H-benz[d,e]isoquinol-2-yl)methyl](hydroxy)phosphinyl]methyl]-4-methylvaleryl]-$N^1$,3-dimethyl-L-valinamide and 0.2 g of 10% palladium-on-carbon in 150 ml of methanol was shaken under a hydrogen atmosphere for 20 hours. The catalyst was removed by filtration and the filtrate was evaporated to give a white foam which was triturated with diethyl ether, filtered off and washed with n-hexane. After drying in vacuo there was obtained 0.47 g of $N^2$-[2(R or S)-[(R)-(amino)[[2,3-dihydro-1,3-dioxo-1H-benz[d,e]isoquinol-2-yl)methyl](hydroxy)phosphinyl]methyl]-4-methylvaleryl]-$N^1$,3-dimethyl-L-valinamide in the form of a white powder; MS: 545 $(M+H)^+$.

EXAMPLE 12

95 mg of $N^2$-[2(R or S)-[(R)-(amino)[[2,3-dihydro-1,3-dioxo-1H-benz[d,e]isoquinol-2-yl)methyl](hydroxy)phosphinyl]methyl]-4-methylvaleryl]-$N^1$,3-dimethyl-L-valinamide were dissolved in 2 ml of dry pyridine and 100 mg of acetic anhydride were added. The solution was stirred at room temperature for 3 hours under a nitrogen atmosphere and was then poured into a stirred mixture of 50% hydrochloric acid and diethyl ether.

The precipitate obtained was filtered off and dried in vacuo to give 95 mg of $N^2$-[2(R or S)-[(R)-acetamido)[[(2,3-dihydro-1,3-dioxo-1H-benz[-d,e]isoquinol-2-yl)methyl](hydroxy)phosphinyl]methyl]-4-methylvaleryl]-$N^1$,3-dimethyl-L-valinamide in the form of a white powder; MS: 587 (M+H)+.

EXAMPLE 13

A mixture of 0.568 g of 2-(R or S)-[(R)-(benzyloxyformamido)[[(2,3-dihydro-6-hydroxy-1,3-dioxo-1H-benz[d,e]isoquinol-2-yl)methyl](hydroxy)phosphinyl]methyl]-4-methylvaleric acid and 0.29 g of L-2-(tert.butyl)glycine methylamide in 45 ml of toluene and 10 ml of 3-methyl-3-pentanol was heated under reflux (bath temperature 140° C.) under a nitrogen atmosphere for 21 hours. The solvents were removed by evaporation, the residue was dissolved in methanol and the solution was filtered. The filtrate was concentrated to 5 ml and 10 ml of 5M hydrochloric acid were added dropwise while stirring. After 30 minutes, the precipitated solid was collected by filtration, washed with water, diethyl ether and n-hexane and dried in vacuo at 60° C. There was obtained 0.506 g of $N^2$-[2(R or S)-[[(R)-(benzyl-carbonyloxyamino)[(2,3-dihydro-6-hydroxy-1,3-dioxo-1H-benz[d,e]isoquinol-2-yl)methyl]-(hydroxy)phosphinyl]methyl]-4-methylvaleryl]-$N^1$,3-dimethyl-L-valinamide in the form of a yellow solid; MS: 695(M+H)+.

The starting material was prepared as follows:

(i) In a manner analogous to that described in Example 10(iv) from 1.76 g of diethyl 2-[(R)-(acetamido)(hydroxyphosphinyl)-methyl]-2-isobutylmalonate and 2.0 g of 4-benzyloxy-N-bromomethyl-1,8-naphthalimide there were obtained 1.51 g of 2[(R)-(acetamido)[[(6-benzyloxy-2,3-dihydro-1,3-dioxo-1H-benz[d,e]isoquinol-2-yl)methyl[(hydroxy)phosphinyl]methyl]-2-isobutylmalonate in the form of a yellow solid; MS: 667 (M+H)+.

(ii) A mixture of 5.29 g of diethyl 2[(R)-(acetamido)[[(6-benzyloxy-2,3-dihydro-1,3-dioxo-1H-benz[d,e]isoquinol-2-yl)methyl[(hydroxy)phosphinyl]-methyl]-2-isobutylmalonate and 1.0 g of 10% palladium-on-carbon in 100 ml of ethanol was shaken in a hydrogen atmosphere until the uptake of hydrogen has ceased. The catalyst was removed by filtration and filtrate was evaporated to give 4.48 g of diethyl 2-[(R)-(acetamido)[[2,3-dihydro-6-hydroxy-1,3-dioxo-1H-benz[d,e]isoquinol-2-yl)methyl](hydroxy)phosphinyl]-methyl]-2-isobutylmalonate in the form of a yellow foam; MS: 577 (M+H)+.

In a manner analogous to that described in Example 10(v), but using 1-methyl-2-pyrrolidinone in place of dimethylsulphoxide as the solvent in the first stage, from 7.89 g of diethyl 2-[(R)-(acetamido)[[2,3-dihydro-6-hydroxy-1,3-dioxo-1H-benz[d,e]-isoquinol-2-yl)methyl](hydroxy)phosphinyl]methyl]-2-isobutyl-malonate there were obtained 2.8 g of 2-(R or S)-[(R)-(benzyloxyformamido)[[(2,3-dihydro-6-hydroxy-1,3-dioxo-1H-benz[d,e]-isoquinol-2-yl)methyl](hydroxy)phosphinyl]-methyl]-4-methyl-valeric acid in the form of a yellow solid; MS: 569 (M+H)+.

EXAMPLE 14

A mixture of 0.284 g of $N^2$-[2(R or S)-[(R)-(benzyloxyformamido)(hydroxyphosphinyl)methyl]-4-methylvaleryl]-$N^1$,3-dimethyl-L-valinamide and 0.48 g of 4-benzyloxy-N-bromomethyl-1,8-naphthalimide in 16 ml of dry chloroform was heated at 60° for 0.5 hour while stirring under an argon atmosphere. 0.7 ml of bis(trimethylsilyl)acetamide was added and heating was continued for an additional 4.9 hours. The solution was cooled and poured into 50 ml of dilute hydrochloric acid. The mixture was extracted three times with dichloromethane and the combined extracts were evaporated to give a residue which was purified by chromatography on silica gel using dichloromethane/methanol/acetic acid/water (240:24:3:2) for the elution. There was obtained 0.4 g of $N^2$-[2(R or S)-[[[(6-benzyloxy)-2,3-dihydro-1,3-dioxo-1H-benz[d,e]isoquinol-2-yl)methyl]hydroxy)phosphinyl]-(R)-(benzyloxyformamido)methyl]-4-methylvaleryl]-$N^1$,3-dimethyl-L-valinamide in the form of a yellow powder; MS: 785 (M+H)+.

The starting material was prepared as follows:

(i) 7.02 g of diethyl 2-[(R)-(acetamido)(hydroxyphosphinyl)-methyl]-2-isobutylmalonate were suspended in 20 ml of water and 1.76 g of lithium hydroxide monohydrate were added. The mixture was stirred at room temperature for 3 days and was then acidified by the addition of 6 ml of concentrated hydrochloric acid. The solution was then saturated with sodium chloride and extracted ten times with dichloromethane. The combined extracts were dried over anhydrous magnesium sulfate and evaporated to give 6.0 g of ethyl hydrogen 2-[(R)-(acetamido)(hydroxyphosphinyl)methyl]-2(RS)-isobutylmalonate in the form of a white foam as a 3:1 mixture of diastereoisomers; MS: 324 (M+H)+.

(ii) A mixture of 13.47 g of ethyl hydrogen 2-[(R)-(acetamido)(hydroxyphosphinyl)methyl]-2(RS)-isobutylmalonate and 8.42 g of triethylamine in 420 ml of dry toluene was heated under reflux for 2 hours. After cooling, the solvent was removed by evaporation and the residue was dissolved in a mixture of 96 ml of water and 144 ml of concentrated hydrochloric acid and the solution was heated under reflux for 4 hours under a nitrogen atmosphere. The solution was evaporated to dryness and the 2-[(R)-(amino)(hydroxyphosphinyl)methyl]-4-methylvaleric acid obtained was dissolved in 225 ml of aqueous saturated sodium hydrogen carbonate solution and 45 ml of tetrahydrofuran. 30 g of solid sodium hydrogen carbonate and 45 ml of benzyl chloroformate were added and the mixture was stirred at room temperature for 48 hours in a nitrogen atmosphere. The solution was extracted twice with diethyl ether and the aqueous solution was acidified by the careful addition of hydrochloric acid and then extracted five times with dichloromethane containing 10% methanol. The extracts were dried over magnesium sulfate and evaporated to give a colorless gum which was crystallized from ethyl acetate. There were obtained 7.0 g of 2(R or S)-[(R)-benzyl-oxyformamido)(hydroxyphosphinyl)methyl]-4-methylvaleric acid as a single diasteroisomer in the form of a white solid; MS: 344 (M+H)+.

A further 0.52 g of the above diasteroisomer was obtained from the mother liquor of the above crystallization by fractional crystallizations from ethyl acetate.

A mixture of 1.37 g 2(R or S)-[(R)-(benzyloxyformamido)(hydroxyphosphinylmethyl))]-4-methylvaleric acid, 0.67 g of L-2-(tert.butyl)glycine N-methylamide and 0.24 g of N-ethyl-morpholine in 40 ml of dry toluene was heated at reflux (bath temperature 140° C.) under nitrogen for 12 hours. The solution was cooled and the solvent was removed by evaporation. The residue was dissolved in 30 ml of ethyl acetate and the solution was shaken with 30 ml of 50% hydrochloric acid. The aqueous layer was separated and extracted eight times with dichloromethane. The organic solutions were combined and evaporated, and the residue was triturated with 25 ml of hot ethyl acetate. After cooling, the insoluble material was filtered off and dried in a vacuum. There were obtained 1.74 g of $N^2$-[2(R or S)-[(R)-(benzyloxyformamido)(hydroxyphosphinyl)-methyl]-4-methyl-valeryl]-$N^1$,3-dimethyl-L-valinamide in the form of a white solid; MS: 493 (M+Na)+.

EXAMPLE 15

In a manner analogous to that described in Example 11, from 0.5 g of $N^2$-[2(R or S)-[[(R)-(benzylcarbonyloxyamino)[(2,3-dihydro-6-hydroxy-1,3-dioxo-1H-benz[d,e]isoquinol-2-yl)-methyl](hydroxyphosphinyl]-methyl]-4-methylvaleryl]-$N^1$,3-dimethyl-L-valinamide, obtained as described in the first paragraph of Example 13, there was obtained 0.29 g of $N^2$-[2-(R or S)-[[(R)-(amino)[(2,3-dihydro-6-hydroxy-1,3-dioxo-1H-benz[d,e]isoquinol-2yl)methyl](hydroxy)phosphinyl]methyl]-4-methylvaleryl]-$N^1$,3-dimethyl-L-valinamide; MS: 561 (M+H)+.

EXAMPLE 16

In a manner analogous to that described in the first paragraph of Example 11, from 0.28 g of $N^2$-[2(R or S)-[[[(6-benzyloxy)-2,3-dihydro-1,3-dioxo-1H-benz[d,e]isoquinol-2-yl)methyl](hydroxy)phosphinyl]-(R)-(benzyloxyformamido)-methyl]-4-methylvaleryl]-$N^1$,3-dimethyl-L-valinamide, obtained as described in Example 14, there was obtained 0.19 g of $N^2$-[2(R or S)-[[(R)-(amino)[(2,3-dihydro-6-hydroxy-1,3-dioxo-1H-benz[d,e]isoquinol-2-yl)methyl](hydroxy)phosphinyl]methyl]-4-methylvaleryl]-$N^1$,3-dimethyl-L-valinamide in the form of a yellow powder; MS: 561 (M+H)+.

EXAMPLE 17

0.45 g of $N^2$-[2(R or S)-[[(R)-(amino)[(2,3-dihydro-6-hydroxy-1,3-dioxo-1H-benz[d,e]isoquinol-2-yl)methyl]-(hydroxy)phosphinyl]methyl]4-methylvaleryl]-$N^1$,3-dimethyl-L-valinamide was dissolved in 10 ml of glacial acetic acid and 7.6 ml of a solution of bromine, prepared by dissolving 2 g of bromine in 100 ml of dichloromethane, was added dropwise over 10 minutes. The mixture was stirred at room temperature for 4 hours and the solvents were removed by evaporation. The residue was dissolved in methanol and evaporated. This procedure was repeated twice and the solid residue was then triturated with ethyl acetate, filtered off and dried in vacuo. There were obtained 595 mg of $N^2$-[2-(R or S)-[[(R)-(amino)-[(5-bromo-2,3-dihydro-6-hydroxy-1,3-dioxo-1H-benz[d,e]isoquinol-2-yl)methyl](hydroxy)-phosphinyl]methyl]-4-methylvaleryl]-$N^1$,3-dimethyl-L-valinamide hydrobromide in the form of a yellow powder; MS: 639/641 (M+H)+.

EXAMPLE 18

0.062 g of 3-[[(2,3-dihydro-1,3-dioxo-1H-benz[d,e]isoquinol-2-yl)methyl](hydroxy)phosphinyl]-2-isobutyl-8-phthalimidooctanoic acid (diasteroisomer 1) was suspended in a mixture of 2 ml of dichloromethane and 4 ml of toluene. 0.5 ml of oxalyl chloride and 1 drop of dimethylformamide were added and the mixture was stirred at room temperature for 5 hours. The solvents were removed by evaporation and the residue was dissolved in dry dichloromethane. A solution of 0.1 g of N-ethylmorpholine and 0.04 g of L-2-(tert.butyl)glycine methylamide in 1 ml of dichloromethane was added and the mixture was stirred at room temperature for 1 hour. The mixture was then poured into 10 ml of 1M hydrochloric acid, shaken and the dichloromethane phase was separated. The aqueous phase was extracted twice with dichloromethane and the combined dichloromethane solutions were evaporated. There was obtained 0.058 g of a 1:1 mixture of diasteroisomers 1A and 1B of $N^2$-[3(RS)-[[(2,3-dihydro-1,3-dioxo-1H-benz[d,e]isoquinol-2-yl)methyl](hydroxy)phosphinyl]-2-isobutyl-8-phthalimidooctanoyl]-$N^1$,3-dimethyl-L-valinamide in the form of a white foam; MS: 745 (M+H)+.

The starting material was prepared as follows:

(i) A solution of 2.95 ml of titanium tetrachloride in 8 ml of carbon tetrachloride was added dropwise while stirring under a nitrogen atmosphere to 50 ml of dry tetrahydrofuran at 0°. The resulting yellow suspension was treated with a solution of 2.45 g of 6-phthalimidohexan-1-al and 3.55 g of dibenzyl malonate in 40 ml of tetrahydrofuran and the mixture was stirred at 0° for 2 hours. A solution of 4.5 g of dry pyridine in 12 ml of dry tetrahydrofuran was added dropwise to give a blood-red suspension. The mixture was left to come to room temperature and was stirred for 18 hours while maintaining the nitrogen atmosphere. 200 ml of 2M sulfuric acid were added and the mixture was extracted four times with dichloromethane. The combined extracts were washed with sodium chloride solution, dried over anhydrous magnesium sulfate and evaporated. The residue was purified by chromatography on silica gel using ethyl acetate/n-hexane (1:2) for the elution to give 3.6 g of dibenzyl 2-(6-phthalimidohexylidene)malonate as a colorless oil.

(ii) 3.6 g of dibenzyl 2-(6-phthalimidohexylidene)malonate were added to a solution of 0.88 g of crystalline hypophosphorus acid in 10 ml of dry dichloromethane, the solution was cooled to 0° and then 2.8 g of triethylamine and 2.8 g of trimethylsilyl chloride were added. After stirring at room temperature for 3 hours, the mixture was poured into 60 ml of 1M hydrochloric acid and the resulting solution was extracted four times with dichloromethane. The combined extracts were dried and evaporated to give 3.9 g of a colorless gum containing crude dibenzyl 2-[1(RS)-(hydroxyphosphinyl)-6-phthalimidohexyl]malonate which was dissolved in 40 ml of dry dimethyl sulphoxide and reacted with isobutyl iodide in a manner analogous to that described in Example 10(ii). After purification of the crude product by chromatography on silica gel using dichloromethane/methanol/acetic acid/water (240:24:3:2) for the elution, there was obtained 2.0 g of dibenzyl 2-[1(RS)-(hydroxyphosphinyl)-6phthalimidohexyl]-2-isobutylmalonate as a colorless gum.

(ii) 5.85 g of dibenzyl 2-[1(RS)-(hydroxyphosphinyl)-6-phthalimidohexyl]-2-isobutylmalonate and 2.7 g of N-bromomethyl-1,8-naphthalimide were reacted with one another in an analogous manner to that described in Example 10(iv) to give 3.74 g of dibenzyl 2-[1(RS)-[[2,3-dihydro-1,3-dioxo-1H-benz[d,e]isoquinol-2-yl)methyl]-(hydroxy)phosphinyl]-6-phthalimidohexyl]-2-isobutylmalonate in the form of an off-white foam; MS: 843 (M+H)+.

(iv) 1.0 g of dibenzyl 2-[1(RS)-[[(2,3-dihydro-1,3-dioxo-1H-benz[d,e]isoquinol-2-yl)methyl](hydroxy)-phosphinyl]-6-phthalimidohexyl]-2-isobutylmalonate was dissolved in 40 ml of dry chloroform and 4 ml of trimethylsilyl bromide were added. The mixture was heated at 60° for 1.5 hours under a nitrogen atmosphere, cooled and poured into 50 ml of water. The mixture was shaken and the chloroform layer was separated. The aqueous layer was extracted twice with dichloromethane and the combined organic phases were evaporated. The residue was purified by chromatography on silica gel using chloroform/methanol/acetic acid/water (240:24:3:2) for the elution. After crystallization of the product from ethyl acetate, there was obtained 0.57 g of a single diastereoisomer of benzyl hydrogen 2-[1-(RS)-[[(2,3-dihydro-1,3-dioxo-1-benz[-d,e]isoquinol-2-yl)methyl](hydroxy)phosphinyl]-6-phthalimidohexyl]-2-isobutylmalonate in the form of off-white crystals; MS: 753 (M+H)+.

(v) 0.2 g of benzyl hydrogen 2-[1(RS)-[[(2,3-dihydro-1,3-dioxo-1-benz[d,e]isoquinol-2-yl)methyl](hydroxy)-phosphinyl]-6-phthalimidohexyl]-2-isobutylmalonate was suspended in 2 ml of dry chloroform and 3 ml of trimethylsilyl bromide were added. The mixture was then treated with 2 drops of water and 2 drops of 48% hydrogen bromide in acetic acid. The solution was left to stand at room temperature for 3 days and was then poured into 50 ml of water. The product was extracted three times with dichloromethane and the combined extracts were dried over anhydrous magnesium sulfate and evaporated. The residue was dissolved in a mixture of 16 ml of xylene and 4 ml of n-hexane containing 4 drops of water and was then heated at 145° for 4 hours. The solvents were removed by evaporation and the residue was purified by chromatography on silica gel using chloroform/methanol/acetic acid/water (240:24:3:2) for the elution. After crystallization from ethyl acetate, there was obtained 0.09 g of 3-[[(2,3-dihydro-1,3-dioxo-1H-benz[d,e]iso-quinol-2-yl)methyl](hydroxy)phosphinyl]-2-isobutyl-8-phthal-imidooctanoic acid (96% diastereoisomer 1) in the form of a white powder; MS: 641 (M+Na)+.

EXAMPLE 19

In a manner analogous to that described in the first paragraph of Example 18, from 0.15 g of 3-[[(2,3-dihydro-1,3-dioxo-1H-benz[d,e]isoquinol-2-yl)methyl](hydroxy)phosphinyl]-2-isobutyl-8-phthalimidooctanoic acid (diastereoisomer 2) and 0.12 g of L-2-(tert.butyl)glycine methylamide there was obtained 0.197 g of a 1:1 mixture of diastereoisomers 2A and 2B of N²-[3(RS)-[[(2,3-dihydro-1,3-dioxo-1H-benz[d,e]isoquinol-2-yl)methyl](hydroxy)phosphinyl]-2-isobutyl-8-phthalimidooctanoyl]-N¹,3-dimethyl-L-valinamide in the form of a pale yellow foam; MS: 745 (M+H)+.

The starting material was prepared as follows:

(i) 0.5 g of benzyl hydrogen 2-[1(RS)-[[(2,3-dihydro-1,3-dioxo-1H-benz[d,e]isoquinol-2-yl)-methyl](hydroxy)phosphinyl]-6-phthalimidohexyl]-2-isobutylmalonate [prepared as described in Example 18(iv)] was suspended in a mixture of 40 ml of xylene, 10 ml of dioxan and 0.25 ml of water and the suspension was heated at 145° for 4.5 hours under a nitrogen atmosphere. The solvents were removed by evaporation and the residue was purified by chromatography on silica gel using chloroform/methanol/acetic acid/water (240:24:3:2) for the elution. After crystallization from ethyl acetate, there was obtained 0.44 g of a single diastereoisomer of benzyl 3-[[(2,3-dihydro-1,3-dioxo-1H-benz[-d,e]isoquinol-2-yl)methyl](hydroxy)phosphinyl]-2-isobutyl-8-phthalimidooctanoate in the form of an off-white solid of melting point 144°–145°.

(ii) 0.3 g of benzyl 3-[[(2,3-dihydro-1,3-dioxo-1H-benz[d,e]-isoquinol-2-yl)methyl](hydroxy)phosphinyl]-2-isobutyl-8-phthalimidooctanoate was suspended in a mixture of 100 ml of methanol and 20 ml of dichloromethane containing 0.1 g of 10% palladium-on-carbon. The mixture was shaken in a hydrogen atmosphere for 20 hours, the catalyst was filtered off and the filtrate was evaporated. The residual gum was crystallized from ethyl acetate to give 0.2 g of 3-[[(2,3-dihydro-1,3-dioxo-1H-benz[d,e]isoquinol-2-yl)methyl](hydroxy)phosphinyl]-2-isobutyl-8-phthalimidooctanoic acid (95% diastereoisomer 2) in the form of a white solid; MS: 641 (M+H)+.

EXAMPLE 20

A mixture of 0.1 g of diastereoisomer 1 and 0.1 g of diastereoisomer 2 of 3-[[(2,3-dihydro-1,3-dioxo-1H-benz[d,e]isoquinol-2-yl)methyl](hydroxy)phosphinyl]-2-isobutyl-7-phthalimidoheptanoic acid and 0.049 g of L-2-(tert.butyl)-glycine methylamide in 10 ml of xylene was heated at 140° for 2 hours. The solvent was removed by evaporation and the residue was purified by chromatography on silica gel using chloroform/methanol/acetic acid/water (240:24:3:2) for the elution. There was obtained 0.216 g of a mixture of diastereoisomers 1A, 1B, 2A and 2B of N²-[3RS)-[[(2,3-dihydro-1,3-dioxo-1H-benz[d,e]isoquinol-2-yl)methyl](hydroxy)-phosphinyl]-2-isobutyl-7-phthalimidoheptanoyl]-N¹,3-dimethyl-L-valinamide in the form of a pale yellow foam.

In a manner analogous to that described in the preceding paragraph, from 0.278 g of diastereoisomer 2 of 3-[[(2,3-dihydro-1,3-dioxo-1H-benz[d,e]isoquinol-2-yl)methyl](hydroxy)phosphinyl]-2-isobutyl-7-phthalimidoheptanoic acid and 0.068 g of L-2-(tert-.butyl)glycine methylamide there was obtained 0.242 g of a mixture of diastereoisomers 2A and 2B of N²-[3(RS)-[[(2,3-dihydro-1,3-dioxo-1H-benz[d,e]isoquinol-2-yl)methyl](hydroxy)phosphinyl]-2-isobutyl-7-phthalimidoheptanoyl]-N¹,3-dimethyl-L-valinamide in the form of yellow foam.

The starting materials were prepared as follows:

In a manner analogous to that described in Example 18(i)–(v), from dibenzyl malonate and 5-phthalimidopentan-al there was obtained diastereoisomers 1 and 2 of 3-[[(2,3-dihydro-1,3-dioxo-1H-benz[d,e]isoquinol-2-yl)methyl](hydroxy)phosphinyl]-2-isobutyl-7-phthalimidoheptanoic acid in the form of white solids.

EXAMPLE 21

0.17 g of a 1:1 mixture of diastereoisomers 2A and 2B of N²-[3(RS)-[[(2,3-dihydro-1,3-dioxo-1H-benz[-d,e]isoquinol-2-yl)methyl](hydroxy)phosphinyl]-2-isobutyl-8-phthalimidooctanoyl]-N¹,3-dimethyl-L-valinamide, prepared as described in the first paragraph of Example 19, was dissolved in 2 ml of ethanol containing 0.08 g of hydrazine hydrate. The mixture was stirred at room temperature for 24 hours and then filtered. The filtrate was evaporated and the resulting foam was partitioned between distilled water and ethyl acetate. The aqueous phase was washed repeatedly with 15 ml portions of ethyl acetate and then evaporated to give 0.12 g of a mixture of diastereoisomers 2A and 2B of N²-[8-amino-3-[[(2,3-dihydro-1,3-dioxo-1H-benz[-d,e]isoquinol-2-yl)methyl](hydroxy)phosphinyl]-2-isobutyloctanoyl]-N¹,3-dimethyl-L-valinamide in the form of a yellow foam; MS: 615 (M+H)+.

EXAMPLE 22

In a manner analogous to that described in Example 21, from 0.245 g of a 1:1 mixture of diastereoisomers 1A and 1B of N²-[3(RS)-[[3-[[(2,3-dihydro-1,3-dioxo-1H-benz[d,e]isoquinol-2-yl)methyl](hydroxy)phosphinyl]-

2-isobutyl-8-phthalimidooctanoyl]-$N^1$,3-dimethyl-L-valinamide there was obtained 0.18 g of a mixture of isomers 1A and 1B of $N^2$-[8-amino-3-[[(2,3-dihydro-1,3-dioxo-1H-benz[d,e]isoquinol-2-yl)methyl](hydroxy)phosphinyl]-2-isobutyloctanoyl]-$N^1$,3-dimethyl-L-valinamide in the form of a yellow foam; MS: 615 (M+H)+.

EXAMPLE 23

In a manner analogous to that described in the first paragraph of Example 10, from 0.414 g of 2(R or S)-[(R)-benzyloxyzyformamido)[[(2,3-dihydro-1,3-dioxo-1H-benz[d,e]isoquinol-2-yl)methyl](hydroxy)phosphinyl]methyl]-4-methylvaleric acid [prepared as described in Example 10(i)–(v)] and 0.552 g of L-2-(tert.butyl)glycine α(S)-methylbenzylamide there was obtained 0.484 g of $N^2$-[2(R or S)-[(R)-(benzyloxyformamido)[[(2,3-dihydro-1,3-dioxo-1H-benz[d,e]isoquinol-2-yl)methyl](hydroxy)phosphinyl]methyl]-4-methylvaleryl]-3-methyl-$N^1$-(α(S)-methylbenzyl)-L-valinamide in the form of an off-white solid; MS: 769 (M+H)+.

The L-2-(tert.butyl)glycine α(S)-methylbenzylamide used as the starting material was prepared as follows:

(i) A solution of 1.76 g of N-benzyloxycarbonyl-L-2-(tert.butyl)glycine in 30 ml of dry dichloromethane was cooled to −5° and 2.8 g of di(1-benzotriazolyl)-carbonate and 0.54 ml of pyridine were added. The mixture was stirred at −5° for 2.5 hours and the 1.6 g of (S)-α-methylbenzylamine were added dropwise while maintaining the temperature −5° to 0°. After stirring at room temperature overnight, the solution was washed twice with saturated sodium hydrogen carbonate sodium, twice with 1M hydrochloric acid and finally with saturated sodium hydrogen carbonate solution. After removal of the solvent by evaporation, the resulting solid was triturated with n-hexane to give 2.05 g of $N^2$-(benzyloxycarbonyl)-3-methyl-$N^1$-(α(S)-methylbenzyl)-L-valinamide in the form of a white solid of melting point 137°–139°.

(ii) 0.5 g of $N^2$-(benzyloxycarbonyl)-3-methyl-$N^1$-(α(S)-methylbenzyl)-L-valinamide was treated in a manner analogous to that described in Example 11 to give 0.31 g of L-2-(tert.butyl)-glycine α-(S)-methylbenzylamide in the form of a colorless gum.

EXAMPLE 24

In a manner analogous to that described in Example 33, from 0.1 g of $N^2$-[2(R or S)-[(R)-benzyloxyformamido)[[(2,3-dihydro-1,3-dioxo-1H-benz[d,e]isoquinol-2-yl)methyl](hydroxy)phosphinyl]methyl]-4-methylvaleryl]-3-methyl-$N^1$-(α(S)-methylbenzyl)-L-valinamide there was obtained 0.045 g of $N^2$-[(2R or S)-[(R)-(amino)[[(2,3-dihydro-1,3-dioxo-1H-benz[d,e]isoquinol-2-yl)methyl](hydroxy)phosphinyl]-methyl]-4-methylvaleryl]-3-methyl-$N^1$-(α(S)-methylbenzyl-L-valinamide hydrobromide in the form of an off-white solid; MS: 635 (M+H)+.

EXAMPLE 25

In a manner analogous to that described in the first paragraph of Example 18, from 0.6 g of diasteroisomer 2 of racemic 2-[1-[[(2,3-dihydro-1,3-dioxo-1H-benz[d,e]isoquinol-2-yl)methyl](hydroxy)phosphinyl]ethyl-4-methylvaleric acid and 0.45 g of L-2-(tert.butyl) glycine methylamide there was obtained 0.9 g of a crude mixture of diasteroisomers 2(i) and 2(ii) of $N^2$-[2-[1-[[(2,3-dihydro-1,3-dioxo-1H-benz[d,e]isoquinol-2-yl)methyl](hydroxy)phosphinyl]ethyl-4-methylvaleryl]-$N^1$,3-dimethyl-L-valinamide in the form of an off-white foam.

The mixture of diasteroisomers was chromatographed on silica gel using chloroform/methanol/acetic acid/water (120:15:3:2) for the elution. The first product eluted was 0.12 g of isomer 2(i) in the form of an off-white foam; MS: 544 (M+H)+.

The starting material was prepared as follows:

(i) In a manner analogous to that described in Example 18(ii)–(iii), from diethyl ethylidenemalonate and crystalline hypophosphorus acid there was obtained diethyl 2-[1(RS-[[(2,3-dihydro-1,3-dioxo-1H-benz[d,e]isoquinol-2-yl)methyl](hydroxy)phosphinyl]ethyl-isobutylmalonate in the form of a white solid of melting point 172°–174°.

(ii) 1 g of diethyl 2-[1(RS)-[[(2,3-dihydro-1,3-dioxo-1H-benz[d,e]isoquinol-2-yl)methyl](hydroxy)phosphinyl]ethyl-isobutylmalonate was dissolved in a mixture of 5 ml of concentrated sulfuric acid, 5 ml of water and 10 ml of acetic acid and the solution was heated at 110° for 20 hours. After cooling, the solution was extracted five times with 10% methanol in dichloromethane. The combined extracts were washed with saturated sodium chloride solution and evaporated. The residue was triturated with 20 ml of ethyl acetate and the solid was filtered off. There was obtained 0.54 g of a mixture of diasteroisomers 1 and 2 of 2-[1-[[(2,3-dihydro-1,3-dioxo-1H-benz[d,e]isoquinol-2-yl)methyl](hydroxy)phosphinyl]ethyl-4-methylvaleric acid in the form of a white solid. This mixture was separated by chromatography on silica gel using chloroform/methanol/acetic acid/water (120:15:3:2) for the elution. There were obtained 75 mg of diasteroisomer 1 racemic 2-[1-[[(2,3-dihydro-1,3-dioxo-1H-benz[d,e]isoquinol-2-yl)methyl]-(hydroxy)phosphinyl]ethyl-4-methylvaleric acid in the form of a white solid of melting point 192°–194° and 225 mg of diasteroisomer 2 racemic 2-[1-[[(2,3-dihydro-1,3-dioxo-1H-benz[d,e]isoquinol-2-yl)methyl](hydroxy)phosphinyl]ethyl-4-methylvaleric acid in the form of a white solid of melting point 202°–204°.

EXAMPLE 26

0.13 g of a mixture of the four diasteroisomers of $N^2$-[7-acetoxy-3(RS)-[[(RS)-[[(2,3-dihydro-1,3-dioxo-1H-benz[d,e]isoquinol-2-yl)methyl](hydroxy)phosphinyl]-2(RS)-isobutylheptanoyl]-$N^1$,3-dimethyl-L-valinamide was added to 20 ml of the methanol was containing 0.06 g of 60% sodium hydride in mineral oil. The mixture was stirred at room temperature for 2.5 hours and the methanol was then removed by evaporation. The residue was dissolved in 30 ml of dichloromethane and the solution was washed twice with 1M hydrochloric acid and twice with saturated sodium chloride solution, dried over anhydrous magnesium sulfate and evaporated. The residue was triturated with diethyl ether and the solid was filtered off to give 0.071 g of an off-white solid which was purified by chromatography on silica gel using chloroform/methanol/acetic acid/water (120:15:3:2) for the elution. There was obtained 0.026 g of a mixture of four diasteroisomers of $N^2$-[3(RS)-[[(2,3-dihydro-1,3-dioxo-1H-benz[d,e]isoquinol-2-yl)methyl](hydroxy)phosphinyl]-7-hydroxy-2(RS)-isobutylheptanoyl]-$N^1$,3-dimethyl-L-valinamide in the form of a white solid; MS: 602 (M+H)+.

EXAMPLE 27

In a manner analogous to that described in the first paragraph of Example 10, from 0.283 g of a mixture of the two diasteroisomers of 7-acetoxy-3-[[(2,3-dihydro-1,3-dioxo-1H-benz[d,e]isoquinol-2-yl)methyl](hydroxy)phosphinyl]-2-isobutylheptanoic acid and 0.16 g of of L-2-(tert.butyl)glycine methylamide there was obtained, after purification by chromatography on silica gel using chloroform/methanol/acetic acid/water (240:24:3:2) for the elution, 0.133 g of a mixture of four diasteroisomers of $N^2$-[7-acetoxy-3-(RS)-[[(2,3-dihydro-1,3-dioxo-1H-benz[d,e]isoquinol-2-yl)methyl](hydroxy)phosphinyl]-2(RS)-isobutylheptanoyl]-$N^1$,3-dimethyl-L-valinamide in the form of an off-white solid; MS: 644 (M+H)+.

The starting material was prepared as follows:

(i) In a manner analogous to that described in Example 18(i)–(iii), from 5-benzoyloxy-pentanal and dibenzyl malonate there was obtained dibenzyl 2-[5-benzyloxy-1-[[(2,3-dihydro-1,3-dioxo-1H-benz[d,e]isoquinol-2-yl)methyl](hydroxy)phosphinyl]pentyl]-2-isobutylmalonate in the form of a gum; MS: 790 (M+H)+.

(ii) In a manner analogous to that described in Example 25(ii), from 0.625 g of dibenzyl 2-[5-benzyloxy-1-[[(2,3-dihydro-1,3-dioxo-1H-benz[d,e]isoquinol-2-yl)methyl](hydroxy)phosphinyl]pentyl]-2-isobutylmalonate there was obtained 0.33 g of a 1:1 mixture of 2 diasteroisomers of 7-acetoxy-3-[[(2,3-dihydro-1,3-dioxo-1H-benz[d,e]isoquinol-2-yl)methyl](hydroxy)phosphinyl]-2-isobutylheptanoic acid in the form of a gum; MS: 540 (M+Na)+.

EXAMPLE 28

A solution of 0.3 g of $N^2$-[2(R or S)-[[(RS)-(ethoxy)[(2,3-dihydro-1,3-dioxo-1H-benz[d,e]isoquinol-2-yl)methyl](hydroxy)phosphinyl]methyl]-4-methylvaleryl]-$N^1$,3-dimethyl-L-valinamide in a mixture of 10 ml of trifluoroacetic acid and 10 ml of dichloromethane was stirred at room temperature overnight. The solvents were removed by evaporation and the residue was triturated with a mixture of isopropanol and diethyl ether. The solid obtained was filtered off and dried to give 0.195 g of $N^2$-[2(R or S)-[[[(2,3-dihydro-1,3-dioxo-1H-benz[d,e]isoquinol-2-yl)methyl](hydroxy)phosphinyl]methyl-4-methylvaleryl]-$N^1$,3-dimethyl-L-valinamide in the form of a white solid; MS: 530 (M+H)+.

The starting material was prepared as follows:

(i) A mixture of 0.3 g of benzyl 2(R or S)-[(ethoxyphosphinyl)methyl]-4-methylvalerate and 0.13 g of diisopropylethylamine in 10 ml of dichloromethane was cooled in an ice-bath while stirring under a nitrogen atmosphere. 2 ml of 1,1,1,3,3,3-hexamethyldisilazane and 1 ml of bis(trimethylsilyl)acetamide were cooled followed by 0.3 g of N-bromomethyl-1,8-naphthalimide. The cooling bath was removed and the mixture was stirred at room temperature for 18 hours, washed with 10% sulfuric acid and sodium chloride solution, dried over anhydrous magnesium sulfate and evaporated to give 0.6 g of a yellow gum which was purified by flash chromatography on silica gel using ethyl acetate n-hexane (3:1) for the elution. There was obtained 0.15 g of benzyl 2(R or S)-[[(RS)-(ethoxy)[(2,3-dihydro-1,3-dioxo-1H-benz[d,e]isoquinol-2-yl)methyl]phosphinyl]methyl-4-methylvalerate in the form of a white solid; MS: 522 (M+H)+.

(ii) 1 g of benzyl 2(R or S)-[[((RS)-(ethoxy)[(2,3-dihydro-1,3-dioxo-1H-benz[d,e]isoquinol-2-yl)methyl]phosphinyl]methyl-4-methylvalerate was suspended in a mixture of 10 ml of methanol and 10 ml of ethanol containing 60 mg of 10% palladium-on-carbon. The mixture was shaken in a hydrogen atmosphere for 24 hours, the solvent was removed by evaporation and the residue was triturated with diethyl ether. The solid was filtered off and dried to give 0.61 g of 2(R or S)-[[(RS)-(ethoxy)[(2,3-dihydro-1,3-dioxo-1H-benz[d,e]isoquinol-2-yl)methyl]phosphinyl]methyl-4-methylvaleric acid in the form of a white solid; MS: 432 (M+H)+.

(iii) 0.43 g of 2(R or S)-[[(RS)-(ethoxy)[(2,3-dihydro-1,3-dioxo-1H-benz[d,e]isoquinol-2-yl)methyl]phosphinyl]methyl-4-methylvaleric acid was suspended in 10 ml of dichloromethane containing 0.095 g of pyridine. The mixture was cooled to 0° and 0.48 g of di-(1-benzotriazolyl)carbonate was added. After stirring at 0° for 1.75 hours, a solution of 0.15 g of L-2-(tert.butyl)glycine in 10 ml of dichloromethane was added. The mixture was left to come to room temperature and was stirred for a further 24 hours. The solution was washed with saturated sodium hydrogen carbonate solution and 1M hydrochloric acid and then evaporated. The residue was purified by flash chromatography on silica gel using a solution of 3% methanol in dichloromethane for the elution. There was obtained 0.319 g of $N^2$-[2(R or S)-[[(RS)-ethoxy)[(2,3-dihydro-1,3-dioxo-1H-benz[d,e]isoquinol-2-yl)methyl]phosphinyl]methyl]-4-methylvaleryl)-$N^1$,3-dimethyl-L-valinamide in the form of a white foam; MS: 558 (M+H)+.

EXAMPLE 29

In a manner analogous to that described in Example 28, from 0.436 g of 6-[[N-[2(R or S)-[[(RS)-(ethoxy)(2,3-dihydro-1,3-dioxo-1H-benz[d,e]isoquinol-2-yl)methyl]phosphinyl]methyl]-4-methylvaleryl]-3-methyl-L-valyl]aminohexanoic acid there was obtained 0.42 g of 6-[[N-[2(R or S)-[[(2,3-dihydro-1,3-dioxo-1H-benz[d,e]isoquinol-2-yl)methyl](hydroxy)phosphinyl]methyl-4-methylvaleryl]-3-methyl-L-valyl]aminohexanoic acid in the form of a white solid; MS: 630 (M+H)+.

The starting material was prepared as follows:

(i) A solution of 9.04 g of N-tert.butoxycarbonyl-L-2-(tert.butyl)glycine in 200 ml of dichloromethane as cooled to 0° and 4.52 g of N-hydroxysuccinimide were added. After stirring for 10 minutes, 8.07 g of dicyclohexylcarbodiimide were added and the mixture was stirred at room temperature for 20 hours. The solid was filtered off, the filtrate was evaporated and the residue was dissolved in 110 ml of dimethylformamide. The solution was added dropwise while stirring to an ice-cold solution of 5.14 g of 6-aminocaproic acid and 4.52 g of tetramethylguanidine in a mixture of 42 ml of dimethylformamide and 17 ml of water. The resulting mixture was left to come to room temperature and was stirred for a further 20 hours. The solvents were removed by evaporation and the residue was partitioned between 10% hydrochloric acid and ethyl acetate. The aqueous phase was extracted three times with ethyl acetate and the combined organic solutions were dried over anhydrous magnesium sulfate and evaporated to give 6-[[$N^2$-(tert.butyloxycarbonyl)-3-methyl-L-valyl]amino]hexanoic acid in the form of a white solid.

(ii) 2.58 g of the foregoing acid were dissolved in 25 ml of dry tetrahydrofuran containing 0.57 g of benzyl alcohol. 1.08 g of dicyclohexylcarbodiimide and 0.064 g of N,N-dimethylaminopyridine were added and the mixture was stirred at room temperature for 20 hours. The mixture was filtered and the filtrate was evaporated. The residue was dissolved in 100 ml of ethyl acetate and the solution was washed with 10% hydrochloric acid, saturated sodium chloride solution, saturated sodium hydrogen carbonate solution and sodium chloride solution. After drying over anhydrous magnesium sulfate, the solution was evaporated to give a colourless oil which was purified by flash chromatography on silica gel using ethyl acetate/n-hexane (2:3) for the elution. There were obtained 1.73 g of benzyl 6-[[N$^2$-(tert.butyloxycarbonyl)-3-methyl-L-valyl]amino]-hexanoate in the form of a colorless gum.

(iii) 10 ml of dioxan saturated with hydrogen chloride were added to a solution of 1.05 g of benzyl 6-[[N$^2$-(tert.butyloxycarbonyl)-3-methyl-L-valyl]amino]hexanoate in 5 ml of dichloromethane. The solution was stirred for 20 minutes and then evaporated. The residue was dissolved in 25 ml of 1M hydrochloric acid and the solution was washed with diethyl ether. The aqueous phase was then treated with solid sodium hydrogen carbonate until saturated and extracted three times with dichloromethane. The combined extracts were evaporated to give 0.565 g of an oil which was added to a mixture of 0.729 g of 2(R or S)-[[(RS)-(ethoxy)[2,3-dihydro-1,3-dioxo-1H-benz[d,e]iso-quinol-2-yl)methyl]phosphinyl]-methyl]-4-methylvaleric acid [prepared as described in Example 28(ii)], 0.134 g of pyridine and 0.716 g of di(1-benzotriazolyl)-carbonate which has previously been stirred at 0° for 1 hour. The mixture was stirred at room temperature for 24 hours, diluted with dichloromethane and washed with saturated sodium hydrogen carbonate solution, 1M hydrochloric acid and saturated sodium hydrogen carbonate solution. The dichloromethane phase was dried over anhydrous magnesium sulfate and evaporated to give a residue which was purified by flash chromatography on silica gel using ethyl acetate for the elution. There was obtained 0.65 g of benzyl 6-[[N-[2-(R or S)-[[(RS)-(ethoxy)(2,3-dihydro-1,3-dioxo-1H-benz[d,e]isoquinol-2-yl)methyl]phosphinyl]methyl]-4-methylvaleryl]-3-methyl-L-valyl]aminohexanoate which was dissolved in 50 ml of ethanol containing 0.1 g of palladium-on-carbon. After shaking in a hydrogen atmosphere for 7 hours, the catalyst was filtered off and the filtrate was evaporated to give 0.436 g of 6-[[N-[2(R or S)-[[(RS)-(ethoxy)(2,3-dihydro-1,3-dioxo-1H-benz[d,e]isoquinol-2-yl)methyl]phosphinyl]methyl]-4-methyl-valeryl]-3-methyl-L-valyl]aminohexanoic acid in the form of a colourless foam; MS: 658 (M+H)$^+$.

EXAMPLE 30

In a manner analogous to that described in Example 28, from 0.25 g of N-[2-(R or S)-[[(RS)-(ethoxy)(2,3-dihydro-1,3-dioxo-1H-benz[d,e]isoquinol-2-yl)methyl]-phosphinyl]methyl]-4-methyl-valeryl]-3-methyl-N-(5-morpholinopentyl)-L-valinamide hydrochloride there was obtained 0.21 g of N-[2(R or S)-[[(2,3-dihydro-1,3-dioxo-1H-benz[d,e]isoquinol-2-ylmethyl]phosphinyl]-methyl]-4-methylvaleryl]-3-methyl-N-(5-morpholinopentyl)-L-valinamide hydrochloride in the form of a colorless solid; MS: 671 (M+H)$^+$.

The starting material was prepared as follows:

(i) A solution of 5.81 g of 6-[[N$^2$-(tert.butyloxycarbonyl)-3-methyl-L-valyl]amino]hexanoic acid in dry tetrahydrofuran was cooled to −30° and treated with 2.15 g of N-ethylmorpholine and then dropwise with a solution of 2.54 g of isobutyl chloroformate in 5 ml of tetrahydrofuran. The solution was stirred at −25° for 0.25 hour and then 2.12 ml of a 33% aqueous ammonium hydroxide solution were added. The mixture was stirred for 3 hours and then evaporated. The product was extracted with dichloromethane and the extract was dried over anhydrous magnesium sulfate and evaporated to give 5.44 g of 6-[[N$^2$-(tert.butyloxycarbonyl)-3-methyl-L-valyl]amino]hexanamide as a gum. This gum was dissolved in a mixture of acetonitrile and water, the solution was stirred and 10.25 g of bis(trifluoroacetoxy)iodobenzene were added. The mixture was stirred in the dark for 20 hours and then poured into 5% hydrochloric acid. The solution was washed twice with diethyl ether which was back-extracted with 5% hydrochloric acid. The combined acidic fractions were treated with 14.18 g of solid sodium hydrogen carbonate, 2.96 g of benzyl chloroformate were added and the mixture was stirred at room temperature for 4 hours. The solution was extracted three times with dichloromethane and the extracts were washed with 50 ml of 1M hydrochloric acid and water. After drying over anhydrous magnesium sulfate, the solvent was removed and there were obtained 6.07 g of N$^2$-(tert.butoxycarbonyl)-3-methyl-N$^1$-[(5-benzyloxyformamido)-pentyl]-L-valinamide in the form of a gum.

(ii) In a manner analogous to that described in Example 29(iii), from 3.06 g of of N$^2$-(tert.butoxycarbonyl)-3-methyl-N$^1$-[(5-benzyloxyformamido)pentyl]-L-valinamide and 2.198 g of 2(R or S)-[[(RS)-(ethoxy)[(2,3-dihydro-1,3-dioxo-1H-benz[d,e]isoquinol-2-yl)methyl]phosphinyl]methyl]-4-methylvaleric acid [prepared as described in Example 28(ii)] there were obtained 1.68 g of N-[2(R or S)-[[(RS)-(ethoxy)(2,3-dihydro-1,3-dioxo-1H-benz[d,e]isoquinol-2-yl)methyl]phosphinyl]methyl]-4-methylvaleryl]-3-methyl-N-[(5-benzyloxyformamido)-pentyl]-L-valinamide in the form of a colorless foam.

(iii) 0.254 g of foregoing foam was dissolved in 20 ml of ethanol containing 0.35 g of 10% hydrochloric acid and 0.05 g of 10% palladium-on-carbon. The mixture was shaken in a hydrogen atmosphere for 6 hours, the catalyst was filtered off and the filtrate was evaporated to give N-[2-(R or S)-[[(RS)-(ethoxy)(2,3-dihydro-1,3-dioxo-1H-benz[d,e]isoquinol-2-yl)methyl]phosphinyl]-methyl]-4-methylvaleryl]-3-methyl-N-(5-aminopentyl)-L-valinamide. This was dissolved in a mixture of 2 ml of dichloromethane and 1.05 g of bis(2-iodoethyl)ether and 0.247 g of diisopropylethylamine was added. The solution was stirred in the dark for 3 days and then poured into 5% hydrochloric acid. The aqueous solution was washed with diethyl ether and then neutralized by the addition of solid sodium hydrogen carbonate. Sodium chloride was added until the solution was saturated and the mixture was extracted three times with dichloromethane. The extracts were evaporated to give a gum which was purified by flash chromatography on silica gel using 6% methanol in dichloromethane for the elution. After the addition of a few drops of 2M hydrochloric acid and evaporation of the solvent, there was obtained 0.131 g of N-[2-(R or S)-[[(RS)-(ethoxy)(2,3-dihydro-1,3-dioxo-1H-benz[d,e]isoquinol-2-yl)methyl]-phosphinyl]methyl]-4-methylvaleryl]-3-methyl-N-(5-morpholinopentyl)-L-valinamide hydrochloride in the form of a pale yellow foam; MS: 699 (M+H)$^+$.

EXAMPLE 31

In a manner analogous to that described in the first paragraph of Example 28, from 0.317 g of 5-[[N-[2(R or S))-[[((RS)-(ethoxy)(2,3-dihydro-1,3-dioxo-1H-benz[d,e]isoquinol-2-yl)methyl]phosphinyl]methyl]-4- methylvaleryl]-3-methyl-L-valyl]amino]pentylamine hydrochloride there was obtained 0.298 g of 5-[[N-[2(R or S)-[[(2,3-dihydro-1,3-dioxo-1H-benz[d,e]isoquinol-2-yl)methyl]phosphinyl]methyl]-4-methylvaleryl]-3-methyl-L-valyl]amino]pentylamine hydrochloride in the form of a white solid; MS: 601 (M+H)+.

EXAMPLE 32

In a manner analogous to that described in the first paragraph of Example 28, from 0.5 g of diethyl [[N-[2(R or S)-[[(RS)-(ethoxy)(2,3-dihydro-1,3-dioxo-1H-benz[d,e]isoquinol-2-yl)methyl]phosphinyl]methyl]-4-methylvaleryl]-3-methyl-L-valyl]aminomethyl]phosphonate there was obtained 0.318 g of diethyl [[N-[2(R or S)-[[[[(2,3-dihydro-1,3-dioxo-1H-benz[d,e]isoquinol-2-yl)methyl](hydroxy)phosphinyl]methyl]-4-methylvaleryl]-3-methyl-L-valyl]aminomethyl]phosphonate in the form of a white solid melting at above 120° C. (decomposition); MS: 666 (M+H)+.

The starting material was prepared as follows:

(i) In a manner analogous to that described in Example 28(i)–(ii), from diethyl(aminomethyl)phosphonate hydrochloride and N-benzyloxycarbonyl-L-2-(tert.butyl)glycine there was obtained diethyl [N-(3-methyl-L-valyl)aminomethyl]phosphonate in the form of a gum.

(ii) In a manner analogous to that described in Example 29(iii), from 1.1 g of diethyl [N-(3-methyl-L-valyl)aminomethyl]phosphonate and 1.5 g of 2(R or S)-[[(RS)-(ethoxy)(2,3-dihydro-1,3-dioxo-1H-benz[d,e]isoquinol-2-yl)methyl]phosphinyl]methyl]-4-methylvaleric acid there was obtained 1.6 g of diethyl [[N-[2(R or S)-[[(RS)-ethoxy)(2,3-dihydro-1,3-dioxo-1H-benz[d,e]isoquinol-2-yl)methyl]phosphinyl]methyl]-4-methylvaleryl]-3-methyl-L-valyl]aminomethyl]phosphonate in the form of a white solid; MS: 694 (M+H)+.

EXAMPLE 33

0.5 g of diethyl [[N-[2(R or S)-[[(RS)-(ethoxy)(2,3-dihydro-1,3-dioxo-1H-benz[d,e]isoquinol-2-yl)methyl]-phosphinyl]methyl]-4-methylvaleryl]-3-methyl-L-valyl]aminomethyl]phosphonate was dissolved in 15 ml of a 45% solution of hydrogen bromide in acetic acid. After 3 hours the mixture was evaporated and the residue was re-evaporated four times with toluene. The residue obtained was triturated with diethyl ether and the solid was filtered off to give 0.35 g of [[N-[2(R or S))-[[[[(2,3-dihydro-1,3-dioxo-1H-benz[d,e]isoquinol-2-yl)methyl]phosphinyl]methyl]-4-methylvaleryl]-3-methyl-L-valyl]amino methyl]phosphonic acid in the form of a white solid melting at above 150° (decomposition); MS: 610 (M+H)+.

EXAMPLE 34

In a manner analogous to that described in the first paragraph of Example 10, from 0.51 g of 2(R or S)-[(R)-[[(6-benzyloxy-1,3-dihydro-1,3-dioxo-1H-benz[d,e]isoquinol-2-yl)methyl](hydroxy)phosphinyl](benzyloxyformamido)methyl]-4-methylvaleric acid and 0.32 g of 3-methyl-N1-(3-morpholino-propyl)-L-valinamide there was obtained, after the addition of hydrogen chloride, 0.416 g of N2[2(R or S)-[(R)-[[(6-benzyloxy-2,3-dihydro-1,3-dioxo-1H-benz[d,e]isoquinol-2-yl)methyl](hydroxy)phosphinyl](benzyloxyformamido)methyl]-4-methyl-valeryl]-3-methyl-N1-(3-morpholinopropyl)-L-valinamide hydrochloride in the form of a yellow solid; MS: 898 (M+H)+.

The starting material was prepared as follows:

(i) In a manner analogous to that described in Example 23(i)–(ii), from N-benzyloxycarbonyl-L-2-(tert.butyl)glycine and 4-(3-aminopropyl) morpholine there was obtained 3-methyl-N1-(3-morpholinopropyl)-L-valinamide.

(ii) In a manner analogous to that described in Example 14, from 4-benzyloxy-N-bromomethyl-1,8-naphthalimide and 2(R or S)-[(R)-(benzyloxyformamido)(hydroxyphosphinyl)methyl]-4-methylvaleric acid [prepared as described in Example 14(ii)] there was obtained 2(R or S)-[(R)-[[(6-benzyloxy-2,3-dihydro-1,3-dioxo-1H-benz[d,e]isoquinol-2-yl)methyl](hydroxy)phosphinyl]benzyl-oxyformamido)methyl-4-methylvaleric acid in the form of a yellow solid; MS: 659 (M+H)+.

EXAMPLE 35

In a manner analogous to that described in Example 11, from 0.75 g of N2-[2-(R or S)-[(R)-[[(6-benzyloxy-2,3-dihydro-1,3-dioxo-1H-benz[d,e]isoquinol-2-yl)methyl](hydroxy)phosphinyl]-benzyloxyformamido)methyl]-4-methylvaleryl]-3-methyl-N1-(3-morpholinopropyl)-L-valinamide hydrochloride there was obtained 0.596 g of N2-[2(R or S)-[(R)-(amino)[[(2,3-dihydro-6-hydroxy-1,3-dioxo-1H-benz[d,e]isoquinol-2-yl)methyl](hydroxy)phosphinyl]methyl]-4-methylvaleryl]-3-methyl-N1-(3-morpholino-propyl)-L-valinamide hydrochloride in the form of a yellow solid; MS: 674 (M+H)+.

EXAMPLE 36

In a manner analogous to that described in the first paragraph of Example 10, from 0.349 g of 2(R or S)-[[[(5-bromo-2,3-dihydro-6-hydroxy-1,3-1H-benz[d,e]isoquinol-2-yl)methyl](hydroxy)phosphinyl]methyl]-4-methylvaleric acid and 0.18 g of 3-methyl-N1-(3-morpholinopropyl)-L-valinamide there was obtained, after the addition of hydrogen chloride, 0.532 g of N2-[2(R or S)-[[[(5-bromo-2,3-dihydro-6-hydroxy-1,3-1H-benz[d,e]isoquinol-2-yl)methyl](hydroxy) phosphinyl]methyl]-4-methylvaleric]-3-methyl-N1-morpholinopropyl)-L-valinamide hydrochloride in the form of a yellow solid; MS: 737 (M+H)+.

EXAMPLE 37

In a manner analogous to that described in the first paragraph of Example 10, from 0.051 g of 2(R or S)-[[[(6-benzyloxy-2,3-dihydro-1,3-dioxo-1H-benz[d,e]isoquinol-2-yl)methyl](hydroxy)phosphinyl]methyl]-4-methylvaleric acid and 0.055 mg (2 equivalents) of 3-methyl-N1-(3-morpholinopropyl)-L-valinamide there was obtained, after the addition of hydrogen chloride, 0.081 g of N2-[2(R or S)-[[[(6-benzyloxy-2,3-dehydro-1,3-dioxo-1H-benz[de]isoquinol-2-yl)methyl](hydroxy)phosphinyl]methyl]-4-methylvaleryl]-3-methyl-N1-(3-morpholinopropyl)-L-valinamide hydrochloride in the form of a pale yellow solid; MS 749 (M+H)+.

EXAMPLE 38

A suspension of 0.354 g of 2(R or S)-[[[(2,3-dihydro-6-hydroxy-1,3-dioxo-1H-benz[de]isoquinol-2-yl)methyl](hydroxy)-phosphinyl]methyl]-4-methylvaleric acid and 0.217 g of 3-methyl-N1-(3-morpholinopropyl)-L-valinamide in a mixture 25 ml of toluene, 5 ml of 3-methyl-3-pentanol and 0.32 ml of N-ethylmorpholine was heated under reflux for 24 hours. The solution was cooled, the solvent was removed by evaporation and the residue was purified by chromatography on silica gel using chloroform/methanol/acetic acid/water (60:18:2:3) for the elution. There was obtained, after the addition of hydrochloric acid, 0.301 g of N²-2(R or S)-[[[(2,3-dihydro-6-hydroxy-1,3-dioxo-1H-benz[-d,e]isoquinol-2-yl)methyl](hydroxy)phosphinyl]-methyl]-4-methylvaleryl]-3-methyl-N¹-(3-morpholinyl-propyl)-L-valinamide hydrochloride in the form of a yellow solid; MS: 659 (M+H)+.

EXAMPLE 39

In a manner analogous to that described in Example 11, from 0.775 g of N²-2(R or S)-[[[(6-benzyloxy-2,3-dihydro-1,3-dioxo-1H-benz[d,e]isoquinol-2-yl)methyl]-(hydroxy)phosphinyl]methyl]-4-methylvaleryl]-3-methyl-N¹-morpholinopropyl)-L-valinamide hydrochloride there was obtained 0.6 g of N²-2(R or S)-[[[(2,3-dihydro-6-hydroxy-1,3-dioxo-1H-benz[d,e]isoquinol-2-yl)methyl](hydroxy)phosphinyl]-methyl]-4-methyl-valeryl]-3-methyl-N¹-(3-morpholinylpropyl)-L-valinamide hydrochloride in the form of a yellow solid; MS: 659 (M+H)+.

EXAMPLE 40

In a manner analogous to that described in Example 38, from 0.59 g of 2(R or S)-[[[(6-benzyloxy-2,3-dihydro-6-hydroxy-1,3-dioxo-1H-benz[d,e]isoquinol-2-yl)methyl](hydroxy)phosphinyl]-methyl]-4-methylvaleric acid and 0.38 g of 4-[(3-methyl-L-valyl)amino]-butyric acid there was obtained 0.775 g of 4-[[N²-[2(R or S)-[[[(6-benzyloxy-2,3-dihydro-1,3-dioxo-1H-benz[-d,e]isoquinol-2-yl)methyl](hydroxy)phosphinyl]methyl]-4-methylvaleryl]-3-methyl-L-valyl]amino]butyric acid in the form of a pale yellow solid; MS: 708 (M+H)+.

EXAMPLE 41

In a manner analogous to that described in Example 38, from 0.51 g of 2(R or S)-[[[(6-benzyloxy-2,3-dihydro-6-hydroxy-1,3-dioxo-1H-benz[d,e]isoquinol-2-yl)methyl](hydroxy)phosphinyl]-methyl]-4-methylvaleric acid and 0.38 g of benzyl [4-[(3-methyl-L-valyl-)amino]propyl]carbamate there was obtained 0.616 g of benzyl [4-[[N²-[2(R or S)-[[[[(6-benzyloxy-2,3-dihydro-1,3-dioxo-1H-benz[de]isoquinol-2-yl)methyl](hydroxy)-phosphinyl]-methyl]-4-methylvaleryl]-3-methyl-L-valyl]amino]propyl]carbamate in the form of a pale yellow solid; MS: 813 (M+H)+.

EXAMPLE 42

In a manner analogous to that described in Example 11, from 0.8 g of 4-[[N²-[2(R or S)-[[[(6-benzyloxy-2,3-dihydro-1,3-dioxo-1H-benz[d,e]isoquinol-2-yl)methyl]-(hydroxy)phosphinyl]methyl]-4-methylvaleryl]-3-methyl-L-valyl]amino]butyric acid there was obtained 0.57 g of 4-[[N²-[2-(R or S)-[[[(6-hydroxy-2,3-dihydro-1,3-1H-benz[de]isoquinol-2-yl)methyl](hydroxy)phos-phinyl]-methyl]-4-methylvaleryl]-3-methyl-L-valyl]amino]-butyric acid in the form of a yellow solid; MS: 618 (M+H)+.

EXAMPLE 43

In a manner analogous to that described in the first paragraph of Example 1, from 0.223 g of N²-[2(R)-[(benzyloxy-carbamoyl)methyl]-4-methylvaleryl]-3-methyl-N¹-(3-morpholinopropyl)-L-valinamide there was obtained 0.12 g of N²-[2(R)-[(hydroxycarbamoyl)-methyl]-4-methylvaleryl]-3-methyl-N¹-(3-morpholino-propyl)-L-valinamide as a white solid; nmr (MeOD): 4.20 (s,1H); 3.70 (t,4H,J=5.5); 3.23 (t,2H,J=7.5; 2.95 (m,1H); 2.54 (br.s,4H); 2.45 (t,2H,J=9); 2.33 (dd,2H,J=14.9); 2.18 (dd,2H,J=14.7); 1.80–1.66 (m,2H); 1.63–1.42 (m,2H); 1.25–1.13 (m,1H); 0.99 (s,9H); 0.92 (d,3H,J=6); 0.87 (d,3H,J=6) MS; 429 (M+H)+.

The starting material was prepared as follows:

In a manner analogous to that described in Example 1 (i)-(ii), from 1.109 g of 4-tert.butyl 2(R)-isobutyl succinate and 1.264 g of 3-methyl-N¹-(3-morpholinopropyl-L-valinamide there were obtained 1.128 g of N²-[2(R)-[(benzyloxycarbamoyl)-methyl]-4-methylvaleryl]-3-methyl-N¹-(3-morpholinopropyl)-L-valinamide in the form of a white foam; MS: 519 (M+H)+.

EXAMPLE 44

6.3 g of N²-[2(R or S)-(carboxy)-4-phenylbutyl]-4-methylvaleryl]-N¹,3-dimethyl-L-valinamide, isomer 1, prepared as described in Example 45 (i)–(iv), and 4.5 g of o-(tert.butyldi-methylsilyl) hydroxylamine were dissolved in 70 ml of dry dimethylformamide and the solution was cooled to 0° while stirring under a nitrogen atmosphere. 3.75 g of hydroxybenzotriazole, 3.0 ml of N-methylmorpholine and 4.13 g of 1-(3-dimethylamino-propyl)-3-ethylcarbamodiimide hydrochloride were added and the mixture was allowed to warm to room temperature and was stirred overnight. The solvent was removed by evaporation and the residue was treated with 200 ml of 5% aqueous sodium hydrogen carbonate solution. The product was extracted three times with ethyl acetate and the combined extracts were washed with 5% aqueous sodium hydrogen carbonate, 5% aqueous citric acid solution and saturated aqueous sodium chloride solution. After drying over anhydrous magnesium sulfate, the solvent was removed by evaporation and the residue was triturated with a mixture of ethyl acetate and diethyl ether. The solid was filtered off and dried to give a 4.6 g of N²-[2(R)-[1(R or S)-(hydroxycarbamoyl)-4-phenylbutyl]-4-methylvaleryl]-N¹,3-dimethyl-L-valinamide in the form of a white powder; nmr (MeOD): 8.14 (d,exch,1H,J=9); 7.95 (m, exch.1H); 7.18 (m,2H); 7.09 (m,3H); 4.20 (d,1H,J=9); 2.67 (d,3H,J=5); 2.64 (m,1H); 2.58–2.47 (m,2H); 2.21-2.13 (m,1H); 1.65–1.45 (m,4H); 1.41–1.28 (m,2H); 1.08–1.00 (m,1H); 0.94 (s,9H); 0.85 (d,3H,J=6); 0.80 (d,3H,J=6); MS: 434 (M+H)+.

EXAMPLE 45

In a manner analogous to that described in the first paragraph of Example 1, from 0.19 g of N²-[2(R)-[1(R or S)-benzyloxycarbamoyl)-4-phenylbutyl]methyl-valeryl]-N¹,3-methyl-L-valinamide there was obtained 0.115 g of N²-[2(R)-[1-(hydroxycarbamoyl)-4-phenyl-butyl]-4-methylvaleryl]-N¹,3-dimethyl-L-valinamide in the form of a white solid; MS: 434 (M+H)+.

The starting material was prepared as follows:

(i) 0.048 g of 60% sodium hydride was added to a stirred solution of 0.45 g of 1,2-dibenzyl 1-tert-butyl 4-methyl-1,1,2-(R)-pentanetricarboxylate in 10 ml of dry dimethylformamide under a nitrogen atmosphere. The mixture was stirred for 0.75 hour at 0° and for a further 2.5 hours at room temperature. The mixture was again cooled to 0° before the addition of 0.236 g of cinnamyl bromide. After allowing the mixture to return slowly to room temperature, the solution was stirred at room temperature for 2 days. The mixture was poured into 5% aqueous citric acid solution and the product was extracted four times with diethyl ether. The combined ether extracts were washed with water and sodium chloride solution and dried over anhydrous magnesium sulfate. The solvent was removed by evaporation and the residue was purified by flash chromatography on silica gel using hexane/ether (9:1) for the elution. There was obtained 0.542 g of 1,2-dibenzyl 1-tert.butyl 4-methyl-1-(3-phenylprop-2-en-1-yl)-1,1,2-(R)-pentanetricarboxylate in the form of a colorless oil; MS: 571 (M+H)+.

(ii) 2.5 g of 1,2-dibenzyl 1-tert.butyl 4-methyl-1-(3-phenyl-prop-2-en-1-yl)-1,1,2-(R)-pentanetricarboxylate were dissolved in 100 ml of methanol containing 0.55 g of 10% palladium-on-charcoal catalyst. The mixture was shaken in a hydrogen atmosphere until the uptake of hydrogen ceased. The catalyst was filtered off and the solvent was removed by evaporation to give 1.94 g of 1-tert.butyl 4-methyl 1-(3-phenylprop-1-yl)-1,1,2(R)-pentanetricarboxylate in the form of a colorless gum. This was dissolved in 120 ml of toluene containing 0.6 g of N-methylmorpholine. The mixture was heated under reflux for 5.5 hours, cooled, the solution was washed twice with citric acid solution and once with saturated aqueous sodium chloride, dried over anhydrous magnesium sulfate and evaporated. The residue was purified by flash chromatography on silica gel using hexane/diethyl ether (10:1) for the elution. After initially eluting 0.524 g of the anhydride corresponding to the starting diacid there was obtained 0.74 g of 4-tert.butyl 2(R)-isobutyl 3-[(R or S)-(3-phenylprop-1-yl)]-succinate, isomer 1, in the form of a colorless gum and 0.126 g of a mixture of isomers 1 and 2 as a gum.

(iii) In a manner analogous to that described in Example 1(i) from 0.741 g of 4-tert.butyl 2(R)-isobutyl 3-[(R or S)-(3-phenylprop-1-yl)]succinate, isomer 1, and 0.32 g of (S)-tert.butylglycine methylamide there was obtained 0.93 g of $N^2$-[2(R)-[1-tert.butoxycarbonyl)-4-phenylbutyl]-4-methylvaleryl]-$N^1$,3-dimethyl-L-valinamide in the form of a colorless foam.

(iv) 0.93 g of $N^2$-2(R)-[1(R or S)-(tert.butoxycarbonyl)-4-phenylbutyl]-4-methylvaleryl]-$N^1$,3-dimethyl-L-valinamide was dissolved in a mixture of 28 ml of dichloromethane and 4 ml of trifluoroacetic acid and the solution was stirred at room temperature for 6 hours. The solvent was removed by evaporation and the residue was re-evaporated with a mixture of methanol and ethyl acetate. After a further evaporation from ethyl acetate, the residue was triturated with diethyl ether to give 0.7 g of $N^2$-[2-(R)-1(R or S)-(carboxy)-4-phenylbutyl]-4-methylvaleryl]-$N^1$,3-dimethyl-L-valinamide, isomer 1, in the form of a white solid; MS: 419 (M+H)+.

(v) In a manner analogous to that described in Example 1(iii), from 0.228 g of $N^2$-[2(R)-1(R or S)-(carboxy)-4-phenylbutyl]-4-methylvaleryl]-$N^1$,3-dimethyl-L-valinamide and 0.077 g of o-benzylhydroxylamine there was obtained 0.192 g of $N^2$-[2(R)-[1(R or S)-(benzyloxycarbamoyl)-4-phenylbutyl]-4-methylvaleryl]-$N^1$,3-dimethyl-L-valinamide in the form of a white foam; MS: 524 (M+H)+.

EXAMPLE 46

In a manner analogous to that described in the first paragraph of Example 1, from 0.135 g of $N^2$-[2(R)-[(R or S)-(benzyl)benzyloxy carbamoyl)methyl]-4-methylvaleryl]-$N^1$,3-dimethyl-L-valinamide there was obtained 0.097 g of $N^2$-[2(R)-[1(R or S)-benzyl)(hydroxycarbamoyl) methyl]-4-methylvaleryl]-$N^1$,3-dimethyl-L-valinamide in the form of a white solid; nmr (MeOD): 7.28-7.07 (m,5H); 4.34 (s,1H); 2.89-2.63 (m,3H); 2.72 (s,3H); 1.62-1.48 (m,1H); 1.47-1.34 (m,1H); 1.18-1.07 (m,1H); 1.04 (s,9H); 0.91 (d,3H,J=6); 0.84 (d,3H,J=6); MS:406 (M+H)+.

The starting material was prepared as follows:

In a manner analogous to that described in Example 45(i-v), from 2.0 g of 1,2-dibenzyl 1-tert.butyl 4-methyl-1,1,2(R)-pentanetricarboxylate and 0.53 ml of benzyl bromide there was obtained 0.77 g of $N^2$-[2(R)-[(R or S)-(benzyl)(benzyloxycarbamoyl)methyl]-4-methylvaleryl]-$N^1$,3-dimethyl-L-valinamide in the form of a white solid; MS: 496 (M+H)+.

EXAMPLE 47

In a manner analogous to that described in the first paragraph of Example 1, from 0.135 g of $N^2$-[2-(R)-[1(R or S)-(benzyloxycarbamoyl)-4-(methoxycarbonyl)-butyl]-4-methylvaleryl]-$N^1$,3-dimethyl-L-valinamide there was obtained 0.10 g of $N^2$-[2(R)-[1(R or S)-(hydroxycarbamoyl)-4-(methoxycarbonyl)-butyl]-4-methylvaleryl]-$N^1$,3-dimethyl-L-valinamide in the form of a white solid; nmr (MeOD): 4.25 (s,1H); 3.62 (s,3H); 2.74-2.62 (m,4H); 2.28 (2H,t,J=7) 2.21-2.11 (m,1H); 1.70-1.29 (m,6H); 1.12-1.04 (m,1H); 1.02 (s,9H); 0.89 (d,3H,J=6); 0.83 (d,3H,J=6); MS: 416 (M+H)+.

The starting material was prepared as follows:

In a manner analogous to that described in Example 45(i)-(v), from 1.82 g of 1,2-dibenzyl 1-tert.butyl 4-methyl-1,1,2(R)-pentanetricarboxylate and 0.8 g of methyl 4-bromocrotonate there was obtained 0.37 g of $N^2$-[2(R)-[1(R or S)-(benzyloxycarbamoyl)-4-(methoxycarbonyl)butyl]-4-methylvaleryl]-$N^1$,3-dimethyl-L-valinamide in the form of a white solid; MS 506 (M+H)+.

EXAMPLE 48

In a manner analogous to that described in the first paragraph of Example 1, from 0.135 g of $N^2$-[2(R)-[1(R or S)-(benzyloxycarbamoyl)-2-phthalimidoethyl]-4-methylvaleryl]-$N^1$,3-dimethyl-L-valinamide there was obtained 0.07 g of $N^2$-[2(R)-[1(R or S)-(hydroxycarbamoyl)-2-phthalimidoethyl]-4-methylvaleryl]-$N^1$,3-dimethyl-L-valinamide in the form of a white solid; nmr (MeOD); 7.88-7.75 (m,4H); 4.33 (s,1H); 4.08 (dd,1H,J=14,10); 3.57 (dd,1H,J=14,4); 2.93-2.75 (m,2H); 2.74 (s,3H); 1.66-1.55 (m,1H); 1.52-1.37 (m,1H); 1.18-1.09 (m,1H); 1.08 (s,9H); 0.93 (d,3H,J=6); 0.85 (d,3H,J=6); MS: 475 (M+H)+.

The starting material was prepared as follows:

(i) In a manner analogous to that described in Example 45(i)-(iv) from 1.82 g of 1,2-dibenzyl 1-tert.butyl 4-methyl-1,1,2(R)-pentanetricarboxylate and 0.96 g of N-bromomethylphthalamide there were obtained 0.73 g of $N^2$-[2(R)-[1(R or S)-(carboxy)-2-phthalimidoethyl]-4-methylvaleryl]-$N^1$,3-dimethyl-L-valinamide in the form of a white solid: MS: 460 (M+H)+.

(ii) In a manner analogous to that described in Example 1 (iii), from 0.17 g of $N^2$-[2(R)-[1(R or S)-(carboxy)-2-phthalimidoethyl]-4-methylvaleryl]-$N^1$,3-dimethyl-L-valinamide and 0.061 of O-benzylhydroxylamine there was obtained 0.161 g of $N^2$-[2(R)-[1-(R or S)-(benzyloxycarbamoyl)-2-phthalimidoethyl]-4-methylvaleryl]-$N^1$,3-dimethyl-L-valinamide in the form of a white solid; MS 565 (M+H)+.

EXAMPLE 49

In a manner analogous to that described in Example 44, from 6.44 g of $N^2$-[2(R)-[1(R or S)-(carboxy)-2-phthalimidoethyl]-4-methylvaleryl]-$N^1$,3-dimethyl-L- valinamide there were obtained 4.74 g of $N^2$-[2(R)-[1(R or S)-(hydroxycarbamoyl)-2-phthalimidoethyl]-4-methylvaleryl]-$N^1$,3-dimethyl-L-valinamide in the form of a white solid.

EXAMPLE 50

In a manner analogous to that described in the first paragraph of Example 1, from 0.115 g of a mixture of isomers of $N^2$-[2(R)-[1-(benzyloxycarbamoyl)butyl]-4-methylvaleryl]-$N^1$,3-dimethyl-L-valinamide there was obtained 0.06 g of $N^2$-[2(R)-[1-(hydroxycarbamoyl)-butyl]-4-methylvaleryl]-$N^1$,3-dimethyl-L-valinamide in the form of a white solid; MS: 358 (M+H)+.

The starting material was prepared as follows:

In a manner analogous to that described in Example 45(i)–(v), from 1,2-dibenzyl 1-tert.butyl 4-methyl-1,1,2(R)-pentanetricarboxlate and allyl bromide there was obtained $N^2$-[2(R)-[1-(benzyloxycarbonyl)butyl]-4-methylvaleryl]-$N^1$,3-dimethyl-L-valinamide as a mixture of isomers.

EXAMPLE 51

In a manner analogous to that described in the first paragraph of Example 1, from 0.198 g of $N^2$-[2(R)-[1(R or S)-(benzyloxycarbamoyl)-2-(2,6-dimethylphenyl)ethyl]-4-methylvaleryl]-$N^1$,3-dimethyl-L-valinamide there was obtained 0.139 g of $N^2$-[2(R)-1(R or S)-(hydroxycarbamoyl)-2-(2,6-dimethylphenyl)ethyl]-4-methylvaleryl]-$N^1$,3-dimethyl-L-valinamide in the form of a white solid; nmr (MeOD): 6.92 (s,3H); 4.32 (s,1H); 3.11 (dd,1H,J=14,12); 2.92–2.82 (m,1H); 2.72 (s,3H); 2.64 (dd,1H,J=14,3); 2.52–2.43 (m,1H); 2.27 (s,6H); 1.61–1.50 (m,1H); 1.48–1.33 (m,1H); 1.17–1.08 (m,1H); 1.07 (s,9H); 0.93 (d,3H,J=6); 0.83 (d,3H,J=6); MS: 434 (M+H)+.

The starting material was prepared as follows:

In a manner analogous to that described in Example 45(i)–(v), from 1,2-dibenzyl 1-tert.butyl 4-methyl-1,1,2(R)-pentanetricarboxylate and 2,6-dimethylbenzyl bromide there was obtained $N^2$-[2(R)-[1(R or S)-(benzyloxycarbamoyl)-2-(2,6-dimethylphenyl)ethyl]-4-methylvaleryl]-$N^1$,3-dimethyl-L-valinamide as a white solid MS; 524 (M+H)+.

EXAMPLE 52

In a manner analogous to that described in the first paragraph of Example 1, from 0.18 g of $N^2$-[2(R)-[2-(4-ethylphenyl)-1(R or S)-(benzyloxycarbamoyl)ethyl]-4-methylvaleryl]-$N^1$,3-dimethyl-L-valinamide there was obtained 0.132 g of $N^2$-[2(R)-[2-(4-ethylphenyl)-1(R or S)-(hydroxycarbamoyl)-ethyl]-4-methylvaleryl]-$N^1$,3-dimethyl-L-valinamide in the form of a white solid; nmr (MeOD); 7.18–6.96 (m,4H); 4.33 (s,1H); 2.84–2.70 (m,5H); 2.65–2.52 (m,3H); 2.44–2.35 (m,1H); 1.58–1.50 (m,1H); 1.46–1.35 (m,1H); 1.18 (t,3H,J=7); 1.17–1.05 (m,1H); 1.04 (s,9H); 0.90 (d,3H,J=6); 0.84 (d,3H,J=6); MS 434 (M+H)+.

The starting material was prepared as follows:

In a manner analogous to that described in Example 45(i)–(v) from 1,2-dibenzyl 1-tert.butyl 4-methyl-1,1,2(R)-pentanetricarboxylate and 4-ethylbenzyl bromide there was obtained $N^2$-[2(R)-[2-(4-ethylphenyl)-1(R or S)-(benzyloxycarbamoyl)ethyl]-4-methylvaleryl]-$N^1$,3-dimethyl-L-valinamide in the form of a white solid; MS: 524 (M+H)+.

EXAMPLE 53

In a manner analogous to that described in the first paragraph of Example 1, from 0.1 g of $N^2$-[2(R)-1(R or S)-benzyloxycarbamoyl)-3-methylbutyl]-4-methylvaleryl]-$N^1$,3-dimethyl-L-valinamide there was obtained 0.057 g of $N^2$-[2(R)-[1(R or S)-(hydroxycarbamoyl)-3-methylbutyl]-4-methylvaleryl]-$N^1$,3-dimethyl-L-valinamide in the form of a white solid; nmr (MeOD); 4.35 (s,1H); 4.70 (s,3H); 4.68–4.57 (m,1H); 2.31–2.19 (m,1H); 1.75–1.29 (m,4H); 1.14–0.95 (m,11H); 0.91–0.78 (m,12H); MS: 372 (M+H)+.

The starting material was prepared as follows:

In a analogous manner to that described in Example 45(i)–(v) from 1,2-dibenzyl 1-tert.butyl 4-methyl-1,1,2(R)-pentanetricarboxylate and methallyl bromide there was obtained $N^2$-[2(R)-[1(R or S)-(benzyloxycarbamoyl)-3-methylbutyl]-4-methylvaleryl]-$N^1$,3-dimethyl-L-valinamide in the form of a white solid; MS: 462 (M+H)+.

EXAMPLE 54

In a manner analogous to that described in the first paragraph of Example 44 from 0.127 g of $N^2$-[2(R)-[1(R or S)-(carboxy)-2-(1-naphthyl)ethyl]-4-methylvaleryl]-$N^1$,3-dimethyl-L-valinamide there was obtained 0.033 g of $N^2$-[2(R)-[1(R or S)-(hydroxycarbamoyl)-2-(1-naphthyl)ethyl]-4-methylvaleryl]-$N^1$,3-dimethyl-L-valinamide in the form of a white solid; nmr; (MeOD): 7.99 (m,1H); 7.83 (m,1H); 7.71 (d,1H,J=7); 7.52–7.23 (m,4H); 4.46 (s,1H); 3.16 (t,1H,J=12); 3.00–2.88 (m,1H); 2.77 (s,3H); 2.75–2.62 (m,2H); 1.62–1.38 (m,2H); 1.21–1.10 (m,1H); 1.08 (s,9H); 0.95 (d,3H,J=6); 0.85 (d,3H,J=6); MS: 456 (M+H)+.

The starting material was prepared as follows:

In a analogous manner to that described in Example 45(i)–(iv), from 1,2-dibenzyl 1-tert.butyl 4-methyl-1,1,2(R)-pentanetricarboxylate and 1-(bromomethyl)-naphthalene there was obtained $N^2$-[2(R)-1(R or S)-(carboxy)-2-(1-naphthyl)ethyl]-4-methylvaleryl]-$N^1$,3-dimethyl-L-valinamide in the form of a white solid; MS: 441 (M+H)+.

EXAMPLE 55

In a manner analogous to that described in Example 45(i)–(v), from 1,2-dibenzyl 1-tert.butyl 4-methyl-1,1,2(R)-pentanetricarboxylate and 2-(bromomethyl)-naphthalene and using 0-(tert.butyldiphenylsilyl) hydroxylamine in part (v) there was obtained $N^2$-[2(R)-[(R or S)-(tert.butyldiphenylsilyloxycarbamoyl)-2-(2-naphthyl)ethyl]-4-methylvaleryl]-$N^1$,3-dimethyl-L-valinamide as a white solid; MS: 694 (M+H)+.

0.102 g of $N^2$-[2(R)-[2(R or S)-(tert.butyldiphenylsilyloxycarbamoyl)-2-(2-naphthyl)ethyl]-4-methylvaleryl]-$N^1$,3-dimethyl-L-valinamide was dissolved in 3 ml of dry tetrahydrofuran and 0.15 ml of 1M tetrabutylammonium fluoride in tetrahydrofuran was added. After stirring at room temperature for 1 hour, the mixture was poured into 1M hydrochloric acid and the product was extracted several times with ethyl acetate. The extracts were combined and washed with 1M hydrochloric acid and saturated solution chloride solution. After drying over anhydrous magnesium sulfate, the solvent was removed by evaporation and the residue was triturated with diethyl ether. There was obtained 0.049 g of $N^2$-[2(R)-[1(R or S)-(hydroxycarbamoyl)-2-(2-naphthyl)ethyl]-4-methylvaleryl]-$N^1$,3-dimethyl-L-valinamide in the form of a white solid; nmr (MeOD): 7.76 (m,3H); 7.57 (s,1H); 7.42 (m,2H); 7.26 (dd,1H,J=7,2); 4.39 (s,1H); 3.01 (t,1H,J=12); 2.92–2.79 (m,2H); 2.73 (s,3H); 2.61–2.49 (m,1H); 1.65–1.52 (m,1H); 1.50–1.37 (m,1H); 1.19–1.09 (m,1H); 1.07 (s,9H); 0.92 (d,3H,J=6); 0.85 (d,3H,J=6), MS: 456 (M+H)+.

EXAMPLE 56

In a manner analogous to that described in the first paragraph of Example 44, from 0.127 g of $N^2$-[2(R)-[1-(R or S)-(carboxy)-(2,3-dihydro)-1,3-dioxo-1H-benz[d,e]isoquinol-2-yl)ethyl]-4-methylvaleryl]-$N^1$,3-dimethyl-L-valinamide there was obtained 0.055 g of $N^2$-[2(R)-[2-(2,3-dihydro-1,3-dioxo-1H-benzy[d,e]isoquinol-2-yl)-1(R or S)-(hydroxycarbamoyl)ethy]-4-methylvaleryl]-$N^1$,3-dimethyl-L-valinamide in the form of a white solid; nmr (MeOD): 7.99 (d,2H,J=7.5); 8.28 (d,2H,J=7.5); 7.75 (t,2H,J=7.5); 4.72 (dd,1H,J=14,10); 4.42 (s,1H); 4.02 (dd,1H, J=14,4); 3.03–2.93 (m,1H); 2.90–2.80 (m,1H); 2.74 (s,3H); 1.70–1.57 (m,1H); 1.53–1.38 (m,1H); 1.23–1.14 (m,1H); 1.10 (s,9H); 0.94 (d,3H,J=6); 0.85 (d,3H,J=6); MS: 525 (M+H)+.

The starting material was prepared as follows:

In a manner analogous to that described in Example 45(i)–(iv), from 1,2-dibenzyl 1-tert.butyl 4-methyl-1,1,2(R)-(carboxy)-(2,3-dipentaneticarboxylate and N-(bromomethyl)-naphthalimide there was obtained $N^2$-[2(R)-[1(R or S)-(carboxy)-(2,3-dihydro-1,3-dioxo-1H-benz[de]isoquinol-2-yl)ethyl]-4-methylvaleryl]-$N^1$,3-dimethyl-L-valinamide in the form of a white solid; MS: 570 (M+H)+.

EXAMPLE 57

In a manner analogous to that described in the first paragraph of Example 1, from 0.15 g of $N^2$-[2(R)-[2-benzamido-1(R or S)-(benzyloxycarbamoyl)ethyl]-4-methylvaleryl]-$N^1$,3-dimethyl-L-valinamide, there was obtained 0.112 g of $N^2$-[2(R)-[2-benzamido-1(R or S)-(hydroxycarbamoyl)ethyl]-4-methylvaleryl]-$N^1$,3-dimethyl-L-valinamide in the form of a white solid; nmr (MeOD): 7.77 (m,2H); 7.56–7.40 (m,3H); 4.28 (s,1H); 3.60–3.46 (m,2H); 2.86–2.76 (m,1H); 2.72 (s,3H); 2.70–2.58 (m,1H); 1.66–1.55 (m,1H); 1.50–1.36 (m,1H); 1.20–1.08 (m,1H); 1.04 (s,9H); 0.92 (d,3H), J=6.5); 0.85, J=6.5): MS: 449 (M+H)+.

The starting material was prepared as follows:

(i) A solution of 0.226 g of $N^2$-[2(R)-[1(R or S)-(benzyloxycarbamoyl)-2-phthalimidoethyl]-4-methylvaleryl]-$N^1$,3-dimethyl-L-valinamide in 5 ml of methanol was treated with 8 ml of a 0.33M solution of hydrazine hydrate in methanol. The mixture was stirred at room temperature overnight and the solvent was removed by evaporation. The residue was stirred with 4 ml of chloroform/methanol/acetic acid/water (120:15:3:2) and the undissolved solids were filtered off. The filtrate was purified by chromatography on silica gel using chloroform/methanol/acetic acid/water (120:15:3:2) for the elution. The fractions containing the product were evaporated and re-evaporated several times in the presence of toluene in order to remove water and acetic acid. There was obtained 0.203 g of $N^2$-[2-(R)-[2-amino-1(R or S)-(benzyloxycarbamoyl)ethyl]-4methylvaleryl]-$N^1$,3-dimethyl-L-valinamide in the form of a white solid; nmr (MeOD); 7.50–7.33 (m,5H); 4.93 (m,2H); 4.23 (s,1H); 3.03 (dd, 1H, J=14,9); 2.83–2.70 (m,2H); 2.68 (s,3H); 2.44–2.32 (m,1H); 1.58–1.47 (m,1H); 1.45–1.29 (m,1H); 1.10–1.02 (m,1H); 0.99 (s,9H); 0.88 (d,3H,J=7); 0.84 (d,3H,J=6).

(ii) 0.2 g of $N^2$-[2(R)-[2-amino-1(R or S)-(benzyloxycarbamoylethyl]-4-methylvaleryl]-$N^1$,3-dimethyl-L-valinamide was dissolved in 5 ml of dry dimethylformamide containing 0.05 g of N-methylmorpholine. The solution was cooled to 0° and 0.077 g of benzoyl chloride was added. After stirring at room temperature for 20 hours, the mixture was poured into 5% aqueous sodium hydrogen carbonate solution and the product was extracted with ethyl acetate. The extract was washed with 5% aqueous citric acid solution and saturated sodium chloride solution, dried over anhydrous magnesium sulfate and evaporated. The residue was purified by flash chromatography on silica gel using ethyl acetate for the elution. There was obtained 0.145 g of $N^2$-[2(R)-[2-benzamido-1(R or S)-(benzyloxycarbamoyl)ethyl]-4-methylvaleryl]-$N^1$,3-dimethyl-L-valinamide in the form of a white solid; nmr (MeOD): 7.80 (m,2H); 7.59–7.42 (m,3H); 7.33–7.19 (m,5H); 4.86 (d,1H,J=12); 4.70 (d,1H,J=12); 4.28 (s,1H); 3.61–3.46 (m,2H); 2.88–2.77 (m,1H); 2.71 (s,3H); 2.65–2.55 (m,1H); 1.60–1.48 (m,1H); 1.46–1.31 (m,1H); 1.11–0.96 (m,10H); 0.90 (d,3H,J=6); 0.83 (d,3H,J=6).

EXAMPLE 58

In a manner analogous to that described in Example 57(i), after treatment of the product with hydrogen chloride to form the hydrogen, from 0.1 g of $N^2$-[2(R)-[1(R or S)-(hydroxycarbamoyl)-2-phthalimidoethyl]-4-methylvaleryl]-$N^1$,3-dimethyl-L-valinamide there were obtained 0.08 g of $N^2$-[2(R)-(2-amino-1(R or S)-(hydroxycarbamoyl)ethyl]-4-methylvaleryl]-$N^1$,3-dimethyl-L-valinamide hydrochloride in the form of a white solid; nmr (MeOD): 4.24 (s,1H); 3.23 (dd,1H,J=12.5,10); 2.92 (dd, 1H, J=12.5,3); 2.84–2.76 (m,1H); 2.69 (s,3H); 2.61–2.53 (m,1H); 1.66–1.55 (m,1H); 1.20–1.12 (m,1H); 1.01 (s,9H); 0.89 (d,3H,J=6); 0.85 (d,3H,J=6); MS: 345 (M+H)+.

EXAMPLE 59

In a manner analogous to that described in the first paragraph of Example 1, from 0.105 g of $N^2$-[2(R)-[2-acetamido-1(R or S)-(benzyloxycarbamoyl)ethyl]-4-methylvaleryl]-$N^1$,3-dimethyl-L-valinamide there was obtained 0.08 g of $N^2$-[2(R)-[2-acetamido-1(R or S)-(hydroxycarbamoyl)ethyl]-4-methylvaleryl]-$N^1$,3-dimethyl-L-valinamide in the form of a white solid; nmr MeOD); 4.16 (s,1H); 3.29 (dd,1H,J=14,3.5); 3.14 (dd,1H,J=14,9); 2.66–2.57 (m,4H); 2.42–2.33 (m,1H); 1.80 (s,3H); 1.51–1.43 (m,1H); 1.36–1.25 (m,1H); 1.04–0.95 (m,1H); 0.93 (s,9H); 0.80 (d,3H,J=6); 0.74 (d,3H,J=6; MS: 387)M+H)+.

The starting material was prepared as follows:

In a manner analogous to that described in Example 57(ii), from $N^2$-[2(R)-[2-amino-1(R or S)-benzyloxycarbamoyl)ethyl]-4-methylvaleryl]-$N^1$,3-dimethyl-L-valinamide and acetic anhydride there was obtained $N^2$-[2(R)-[2-acetamido-1(R or S)-(benzyloxycarbamoyl)ethyl]-4-methylvaleryl]-$N^1$,3-dimethyl-L-valinamide in the form of a white solid; MS: 477 (M+H)+.

EXAMPLE 60

In a manner analogous to that described in the first paragraph of Example 1, from 0.18 g of $N^2$-[2(R)-[1(R or S)-(benzyloxycarbamoyl)-2-(morpholino)ethyl]-4-methylvaleryl]-$N^1$,3-dimethyl-L-valinamide there was obtained 0.11 g of $N^2$-[2(R)-[1(R or S)-(hydroxycarbamoyl)-2-(morpholino)ethyl]-4-methylvaleryl[-$N^1$,3-dimethyl-L-valinamide in the form of white solid; nmr (MeOD): 4.23 (s,1H); 3.60 (m,4H); 2.74 (t,1H,J=12); 2.68 (s,3H); 2.63 (dt,1H,J=10,4); 2.53–2.42 (m,3H); 2.27–2.20 (m,2H); 2,14 (dd,1H,J=14,3.5); 1.55–1.45 (m,1H); 1.42–1.30 (m,1H); 1.14–1.05 (m,1H); 1.01 (s,9H); 0.86 (d,3H,J=6); 0.82 (d,3H,J=6); MS: 415 (M+H)+.

The starting material was prepared as follows:

A mixture of 0.27 g of $N^2$-[2(R)-[2-amino-1(R or S)-(benzyloxycarbamoyl)ethyl]-4-methylvaleryl]-$N^1$,3-dimethyl-L-valinamide, 0.25 g of N,N-diisopropylethylamine, and 0.5 ml of bis(2-iodoethyl)ether in 4 ml of dimethylformaide was left to stand at room temperature for 3 days in the dark. The mixture was poured into water and was extracted with ethyl acetate. The ethyl acetate extract was washed in succession with water, aqueous sodium thiosulfate solution, water and saturated sodium chloride solution. The solution was dried over anhydrous magnesium sulfate and evaporated, After trituration with diethyl ether there was obtained 0.18 g of $N^2$-[2(R)-[1(R or S)-(benzyloxycarbamoyl)-2-(morpholino)ethyl]-4-methylvaleryl]-$N^1$,3-dimethyl-L-valinamide in the form of a white solid; MS: 505 (M+H)+.

EXAMPLE 61

0.04 g of lithium hydroxide monohydrate was added to a solution of 0.141 g of $N^2$-[2(R)-[1(R or S)-(hydroxycarbamoyl)-2-phthalimidoethyl]-4-methylvaleryl]-$N^1$,3-dimethyl-L-valinamide in a mixture of 4 ml of methanol and 8 ml of water. After 15 minutes, the mixture was poured into 1M hydrochloric acid and the solution was extracted repeatedly with ethyl acetate containing 5% methanol. The combined extracts were washed with water and then evaporated. After trituration of the residue with diethyl ether there was obtained 0.121 g of $N^2$-[2(R)-[2-carboxybenzamido)-1(R or S)-(hydroxycarbamoyl)ethyl]-4-methylvaleryl]-$N^1$,3-dimethyl-L-valinamide in the form of a white solid; nmr (MeOD): 7.98 (dd,1H,J=7.5,2); 7.59 (dt,1H,J=7.5,2); 7.52 (dt,1H,J=7.5,2); 7.44 (dd,1H,J=7.5,2); 4.28 (s,1H); 3.55 (dd,1H,J=14,6.5); 3.45 (dd,1H,J=14,4); 2.95–2.87 (m,1H); 2.71 (s,3H); 2.70–2.62 (m,1H); 1.63–1.54 (m,1H); 1.44–1.34 (m,1H); 1.15–1.06 (m,1H); 1.03 (s,9H); 0.88 (dd,1H,J=6); 0.84 (dd,1H,J=6); MS: 493 (M+H)+.

EXAMPLE 62

In a manner analogous to that described in the first paragraph of Example 1, from 0.11 g of $N^2$-[2(R)-[1(R or S)-(benzyloxycarbamoyl)-2-(3-carboxypropionamido)ethyl]-4-methylvaleryl]-$N^1$,3-dimethyl-L-valinamide there was obtained 0.075 g of $N^2$-[2(R)-[2-(3-carboxypropionamido)-1(R or S)-(hydroxycarbamoyl)ethyl]-4-methylvaleryl]-$N^1$,3-dimethyl-L-valinamide in the form of a white solid; nmr (MeOD): 4.23 (s,1H); 3.39–3.21 (m,2H); 2.77–2.69 (m,1H); 2.68 (s,3H); 2.55 (t,2H,J=7); 2.49–2.37 (m,3H); 1.58–1.49 (m,1H); 1.42–1.321 (m,1H); 1.12–1.03 (m,1H); 0.99 (s,9H); 0.86 (d,3H,J=6); 0.81 (d,3H,J=6); MS 445 (M+H)+.

The starting material was prepared as follows:

In a manner analogous to that described in Example 57(ii), from $N^2$-[2(R)-[2-amino-1(R or S)-(benzyloxycarbonyl)ethyl]-4-methylvaleryl]-$N^1$,3-dimethyl-L-valinamide and succinic anhydride there was obtained $N^2$-[2(R)-[1(R or S)-(benzyloxycarbonyl)-2-(3-carboxypropionamido)ethyl]-4-methylvaleryl]-$N^1$,3-dimethyl-L-valinamide in the form of a white solid; MS: 535 (M+H)+.

EXAMPLE 63

In a manner analogous to that described in the first paragraph of Example 1, from 0.15 g of $N^2$[2(R)-[1(R or S)-(benzyloxycarbamoyl)-2-succinimidoethyl]-4-methylvaleryl]-$N^1$,3-dimethyl-L-valinamide there was obtained 0.11 g of $N^2$-[2(R)-[1-(R or S)-(hydroxycarbamoyl)-2-succinimidoethyl]-4-methylvaleryl]-$N^1$,3-dimethyl-L-valinamide in the form of a white solid: nmr (MeOD): 3.88 (dd,1H,J=14,10); 3.37 (dd,1H,J=14,4); 2.80 (dt,1H,J=14,3.5); 2.72 (s,3H); 2.65 (m,5H); 1.60–1.51 (m,1H); 1.46–1.35 (m,1H); 1.14–1.05 (m,1H); 1.03 (s,9H); 0.88 (d,3H,J=6); 0.82 (d,3H,J=6); MS: 427 (M+H)+.

The starting material was prepared as follows:

A solution of 0.318 g of $N^2$-[2(R)-[1(R or S)-(benzyloxycarbonyl)-2-(3-carboxypropionamido)ethyl]-4-methylvaleryl]-$N^1$,3-dimethyl-L-valinamide in 6 ml of dry dimethylformamide was treated in succession with 0.09 g of hydroxybenzotriazole, 0.09 g of N-methylmorpholine and 0.144 g of 1-(3-dimetylaminopropyl)-3-ethylcarbodiimide. The mixture was stirred at room temperature for 20 hours then poured into 5% aqueous sodium hydrogen carbonate solution. The product was extracted with ethyl acetate and the extract was washed with 5% citric acid solution and with saturated sodium chloride solution. After drying over anhydrous magnesium sulfate, the solvent was removed by evaporation and the residue was purified by flash chromatography on silica gel using 5% methanol in dichloromethane for the elution. There was obtained 0.16 g of $N^2$-[2(R)-[1(R or S)-(benzyloxycarbamoyl)-2-succinimidoethyl]-4-methylvaleryl]-$N^1$,3-dimethyl-L-valinamide in the form of a white solid; MS: 517 (M+H)+.

EXAMPLE 64

In a manner analogous to that described in the first paragraph of Example 1, from 0.12 g of $N^2$-[2(R)-[1(R or S)-(benzyloxycarbamoyl)-4-(carboxy)butyl]-4-methylvaleryl]-$N^1$,3-dimethyl-L-valinamide there was obtained 0.088 g of $N^2$-[2(R)-[4-carboxy-1(R or S)-(hydroxycarbamoyl)butyl]-4-methylvaleryl]-$N^1$,3-dimethyl-L-valinamide in the form of a white solid; nmr (MeOD): 4.14 (s,1H); 2.63–2.54 (m,4H); 2.12 (t,2H, J=7); 2.10–2.02 (m,1H); 1.58–1.22 (m,6H); 1.02–0.93 (m,1H); 0.91 (s,9H); 0.78 (d,3H,J=6); 0.73 (d,3H,J=6H); MS: 402 (M+H)+.

The starting material was prepared as follows:

A mixture of 0.09 g of $N^2$-[2(R)-[1(R or S)-(benzyloxycarbamoyl)-4-(methoxycarbonyl)butyl]-4-methylvaleryl]-$N^1$,3-dimethyl-L-valinamide, 0.012 g of lithium hydroxide monohydrate, 0.55 ml of tetrahydrofuran and 0.36 ml of water was stirred at room temperature for 3 days. The tetrahydrofuran was removed by evaporation and the residue was diluted with ethyl acetate and washed with two portions of 0.5M hdyrochloric acid and then with saturated sodium chloride solution. After drying over anhydrous magnesium sulfate, the solvent was removed by evaporation and there was obtained 0.078 g of $N^2$-[2(R)-[1(R or S)-(benzyloxycarbamoyl)-4-(carboxy)butyl]-4-methylvaleryl]-$N^1$,3-dimethyl-L-valinamide in the form of a white solid; MS 492 (M+H)+.

EXAMPLE 65

In a manner analogous to that described in the first paragraph of Example 1, from 0.094 g of a mixture of isomers of 0.094 g $N^2$-[2(R)-[1-(benzyloxycarbamoyl)-4-

(1-pyrrolidinyl)-butyl]-4-methylvaleryl]-N$^1$,3-dimethyl-L-valinamide there was obtained 0.066 g of N$^2$-[2(R)-[1-(hydroxycarbamoyl)-4-(1-pyrrolidinyl)-butyl]-4-methylvaleryl]-N$^1$,3-dimethyl-L-valinamide as an off-white solid, as a mixture of diastereosiomers; MS 441 (M+H)$^+$.

The starting material was prepared as follows:

(i) In a manner analogous to that described in Example 45(i), from 5.0 g of 1,2-dibenzyl 1-tert.butyl 4-methyl-1,1,2(R)-pentanetricarboxylate and 3.3 g of propargyl bromide there were obtained 5.58 g of 1,2-dibenzyl 1-tert.butyl 4-methyl-1-(prop-2-yn-1-yl)-1,1,2(R)-pentanetricarboxylate in the form of a colorless oil; MS 493 (M+H)$^+$.

(ii) A mixture of 0.501 g of 1,2-dibenzyl 1-tert.butyl 4-methyl-1-(prop-2-yn-1-yl)-1,1,2(R)-pentanetricarboxylate, 0.17 ml of pyrrolidine, 0.083 g of paraformaldehyde, 0.39 ml of glacial acetic acid and 0.004 g of cuprous chloride in 7 ml of dioxan was stirred at room temperature under a nitrogen atmosphere for 15 minutes and then heated to reflux for 2 hours. The mixture was then stirred at room temperature for a further 2 hours and evaporated, and the residue was partitioned between water and dichloromethane. The pH of the aqueous phase was adjusted to 10 by the addition of ammonium hydroxide and the dichloromethane layer was separated. The aqueous phase was extracted with three portions of dichloromethane and the combined extracts were washed with water, dried over anhydrous magnesium sulfate and evaporated to give a brown oil which was purified by flash chromatography on silica gel using ethyl acetate/hexane (4:1) for the elution. There was obtained 0.489 g of 1,2-dibenzyl 1-tert.butyl 4-methyl-1-(4-pyrrolidinylbut-2-yn-1-yl)-1,1,2(R)-pentanetricarboxylate in the form of a colorless oil; MS 576 (M+H)$^+$.

(iii) In a manner analogous to that described in Example 45(ii)–(v), from 1,2-dibenzyl 1-tert.butyl 4-methyl-1-(4-pyrrolidinylbut-2-yn-1-yl)-1,1,2(R)-pentanetricarboxylate there was obtained N$^2$-[2(R)-[1-(benzyloxycarbamoyl)-4-(1-pyrrolidinyl)butyl]-4-methylvaleryl]-N$^1$,3-dimethyl-L-valinamide in the form of a white solid, as a mixture of diastereoisomers; MS: 531 (M+H)$^+$.

EXAMPLE 66

In a manner analogous to that described in the first paragraph of Example 44, from 0.14 g of N$^2$-[2-(R)-[1(R or S)-(carboxy)-6-phenylhexyl]-4-methylvaleryl]-N$^1$,3-dimethyl-L-valinamide there was obtained 0.046 g of N$^2$-[2(R)-[1(R or S)-(hydroxycarbamoyl)-6-phenylhexyl]-4-methylvaleryl]-N$^1$,3-dimethyl-L-valinamide in the form of a white solid; nmr (MeOD): 7.24 (m,2H); 7.13 (m,3H); 4.25 (s,1H); 2.69 (s,3H); 2.3 (m,1H); 2.55 (t,2H,J=7); 2.17–2.09 (m,1H); 1.64–1.45 (m,4H); 1.42–1.13 (m,6H); 1.10–1.02 (m,1H); 0.98 (s,9H); 0.88 (d,3H,J=6); 0.83 (d,J=6); MS 462 (M+H)$^+$.

The starting material was prepared as follows:

(i) In a manner analogous to that described in Example 45(i), from 7.28 g of 1,2-dibenzyl 1-tert.butyl 4-methyl-1,1,2(R)-pentanetricarboxylate and 3.88 g of allyl bromide there were obtained 7.234 g of 1,2-dibenzyl 1-tert.butyl 4-methyl-1-(prop-2-en-1-yl)-1,1,2(R)-pentanetricarboxylate in the form of a colorless oil; MS: 495 (M+H)$^+$.

(ii) A mixture of 1.23 g of 1,2-dibenzyl 1-tert.butyl 4-methyl-1-(prop-2-en-1yl)-1,1,2(R)-pentanetricarboxylate, 3 ml of a 1% aqueous solution of osmium tetroxide, 2.44 g of sodium periodate, 15 ml of diethyl ether and 15 ml of water was stirred at room temperature for 1 hour. A further 3.25 g of sodium periodate were added and the mixture was stirred at room temperature for 24 hours. The ether layer was separated and the aqueous layer was extracted with diethyl ether. The combined ether layers were washed repeatedly with 5% aqueous ascorbic acid solution and saturated sodium chloride solution. After drying over magnesium sulfate, the solution was evaporated and the residue was purified by flash chromatography on silica gel using hexane/diethyl ether (8:1) for the elution. There was obtained 0.955 g of 1,2-dibenzyl 1-tert.butyl 1-(formylmethyl)-4-methyl-1,1,2(R)-pentanetricarboxylate in the form of a colorless oil; MS: 497 (M+H)$^+$.

(iii) A mixture of 0.496 g of 1,2-dibenzyl 1-tert.butyl 1-(formylmethyl)-4-methyl-1,1,2(R)-pentane tricarboxylate, 0.176 g of potassium carbonate and 0.576 g of 3-phenylpropyltriphenylphosphonium bromide in 8 ml of dry tetrahydrofuran was heated at reflux under a nitrogen atmosphere for 3 days. The solvent was removed by evaporation and stirred with diethyl acetate. The solids which separated were filtered off and the filtrate was evaporated. The residue was purified by flash chromatography on silica gel using hexane/ethyl acetate (6:1) for the elution. There was obtained 0.397 g of 1,2-dibenzyl 1-tert.butyl 4-methyl-1-(5-phenyl-pent-2-en-1-yl)-1,1,2(R)-pentanetricarboxylate in the form of a colorless oil.

(iv) In a manner analogous to that described in Example 45(ii)–(iv), from 1,2-dibenzyl 1-tert.butyl 4-methyl-1-(5-phenylpent-2-en-1-yl)-1,1,2(R)-pentanetricarboxylate there was obtained N$^2$-[2(R)-[1(R or S)-(carboxy)-6-phenylhexyl]-4-methylvaleryl]-N$^1$,3-dimethyl-L-valinamide in the form of a white solid; MS: 447 (M+H)$^+$.

EXAMPLE 67

In a manner analogous to that described in the first paragraph of Example 44, from 0.15 g of N$^2$-[2(R)-[4-acetoxy-1(R or S)-(carboxy)butyl]-4-methylvaleryl]-N$^1$,3-dimethyl-L-valinamide there was obtained 0.043 g of N$^2$-[2(R)-[4-acetoxy-1(R or S) (hydroxycarbamoyl)butyl]-4-methylvaleryl]-N$^1$,3-dimethyl-L-valinamide in the form of a white solid; nmr (MeOD): 4.22 (s,1H); 4.02–3.68 (m,2H); 2.68–2.60 (m,4H); 2.2 (dt,1H, J=11,3.5); 1.93 (s,3H); 1.65–1.37 (m,5H), 1.36–1.26 (m,1H); 1.06–0.98 (m,1H); 0.96 (s,9H); 0.84 (d,3H,J=7); 0.77 (d,3H,J=7); MS: 416 (M+H)$^+$.

The starting material was prepared as follows:

(i) A solution of 2.47 g of 1,2-dibenzyl 1-tert.butyl 4-methyl-1-(prop-2-en-1-yl)-1,1,2(R)-pentanetricarboxylate in 5 ml of dry diethyl ether was cooled to 0° and 0.325 ml of monochloroborane-methyl sulphide complex was added. The mixture was stirred at room temperature for 2 hours, then cooled to 0° and 0.5 ml of water, 2.3 ml of 1.5M aqueous sodium hydroxide solution and 2.3 ml of 30% aqueous hydrogen peroxide were added. The mixture was stirred at room temperature for 3 hours and then acidified with 5% aqueous citric acid solution. The product was extracted with diethyl ether and the extract was washed with saturated sodium chloride solution, dried over anhydrous magnesium sulfate and evaporated. The residue was purified by flash chromatography on silica gel using hexane/ethyl acetate (5:1) for the elution. There were obtained 1.098 g of 1,2-dibenzyl 1-tert.butyl 1-(3-hydroxypropyl)-4-methyl-1,1,2(R)-pentanetricarboxylate in the form of a colorless oil; MS: 513 (M+H)+.

(iii) A solution of 1.069 g of 1,2-dibenzyl 1-tert.butyl 1-(3-hydroxypropyl)-4-methyl-1,1,2(R)-pentanetricarboxylate in 10 ml of pyridine at 0° was treated with 0.643 g of acetic anhydride. The mixture was stirred at room temperature for 20 hours and evaporated. The residue was dissolved in ethyl acetate and the solution was washed with 1M hydrochloric acid and with saturated aqueous sodium hydroxide and dried over anhydrous magnesium sulfate. The solvent was removed by evaporation and there were obtained 1.155 g of 1,2-dibenzyl 1-tert.butyl 1-(3-acetoxypropyl)-4-methyl-1,1,2(R)-pentanetricarboxylate in the form of an oil.

(iv) In a manner analogous to that described in Example 45 (ii)–(iv), from 1,2-dibutyl 1-tert.butyl 1-(acetoxypropyl)-4-methyl-1,1,2(R)-pentanetricarboxylate there was obtained $N^2$-[2(R)-[4-acetoxy-1(R or S)-(carboxy)-butyl]-4-methylvaleryl]-$N^1$,3-dimethyl-L-valinamide in the form of a white solid; MS: 401 (M+H)+.

EXAMPLE 68

In a manner analogous to that described in the first paragraph of Example 1, from 0.058 g of $N^2$-[2(R)-[1-(R or S)-(benzyloxy carbamoyl)-4-hydroxybutyl]-4-methylvaleryl]-$N^1$,3-dimethyl-L-valinamide there was obtained 0.027 g $N^2$-[2-(R)-[4-hydroxy-1(R or S)-(hydroxycarbamoyl)butyl]-4-methylvaleryl]-$N^1$,3-dimethyl-L-valinamide in the form of a white solid; nmr (MeOD): 4.25 (s,1H); 3.46 (t,2H,J=6); 2.70 (s,3H); 2.67 (dt,1H, J=11,4); 2.16 (dt,1H,J=11,3.5); 1.67–1.31 (m,6H); 1.12–1.04 (m,1H); 1.01 (s,9H); 0.88 (d,3H,J=6); 0.83 (d,3H,J=6); MS: 374 (M+H)+.

The starting material was prepared as follows:

(i) In a manner analogous to that described in Example 1(iii), from $N^2$-[2(R)-[4-acetoxy-[1(R or S)-(carboxy)butyl]-4-methylvaleryl]-$N^1$,3-dimethyl-L-valinamide there was obtained $N^2$-[2(R)-4-acetoxy-1(R or S)-benzyloxycarbamoyl)butyl]-4-methylvaleryl]-$N^1$,3-dimethyl-L-valinamide in the form of a white solid.

(ii) In a manner analogous to that described in the last paragraph of Example 64, from 0.1 g of $N^2$-[2(R)-[4-acetoxy-1(R or S)-(benzyloxycarbamoyl)butyl]-4-methylvaleryl]-$N^1$,3-dimethyl-L-valinamide, there were obtained 0.058 g of $N^2$-[2(R)-[(R or S)-(benzyloxycarbamoyl)-4-hydroxybutyl]-4-methylvaleryl]-$N^1$,3-dimethyl-L-valinamide in the form of a white solid; nmr (MeOD): 7.46 (m,2H); 7.37 (m,3H); 4.88 (m,2H); 4.23 (s,1H); 3.44 (t,2H,J=7); 2.74–2.65 (m,4H); 2.14–2.06 (m,1H); 1.63–1.55 (m,1H); 1.50–1.29 (m,6H); 1.04–0.95 (m,10H); 0.87 (d,3H,J=7); 0.82 (d,3H,J=7).

EXAMPLE 69

In a manner analogous to that described in the first paragraph of Example 44, from 0.1 g of $N^2$-[2(R)-[1(R or S)-(carboxy)-3-phthalimidopropyl]-4-methylvaleryl]-$N^1$,3-dimethyl-L-valinamide there was obtained 0.060 g of $N^2$-[2(R)-[1(R or S)-(hydroxycarbamoyl)-3-phthalimidopropyl]-4-methylvaleryl]-$N^1$,3-dimethyl-L-valinamide in the form of a white solid; nmr (MeOD): 7.87–7.76 (m,4H); 4.20 (s,1H); 3.68–3.51 (m,2H); 2.74–2.65 (m,4H); 2.22 (dt,1H,J=10,3.5); 2.05–1.93 (m,1H); 1.85–1.75 (m,1H); 1.54–1.45 (m,1H); 1.41–1.29 (m,1H); 1.13–1.04 (m,1H); 1.06 (s,9H); 0.86 (d,3H,J=6); 0.81 (d,3H,J=6); MS: 489 (M+H)+.

The starting material was prepared as follows:

(i) 8.2 ml of a 1M solution of borane in tetrahydrofuran was added to a solution of 4.055 g of 1,2-dibenzyl 1-tert.butyl 1-(formylmethyl)-4-methyl-1,1,2(R)-pentanetricarboxylate in 40 ml of dry tetrahydrofuran. After stirring for 5 minutes, the mixture was acidified with 5% aqueous citric acid solution and was extracted twice with ethyl acetate. The combined extracts were washed with saturated sodium chloride solution, dried over anhydrous magnesium sulfate and evaporate. The residue was purified by flash chromatography on silica gel using hexane/ethyl acetate for the elution. There was obtained 2.518 g of 1,2-dibenzyl 1-tert.butyl 1-(hydroxymethyl)-4-methyl-1,1,2(R)-pentanetricarboxylate in the form of a colorless oil.

(ii) A mixture of 2.911 g of 1,2-dibenzyl 1-tert.butyl 1-(hydroxymethyl)-4-methyl-1,2,2(R)-pentanetricarboxylate, 3.04 g of triphenylphosphine and 1.755 g of phthalimide in 50 ml of dry tetrahydrofuran was cooled to 0° and 2.047 g of diethyl azodicarboxylate were added. The mixture was stirred at room temperature under a nitrogen atmosphere for 20 hours. The solvent was removed by evaporation and the residue was purified by flash chromatography on silica gel using hexane/ethyl acetate (5:1) for the elution. There were obtained 3.001 g of 1,2-dibenzyl 1-tert.butyl 4-methyl-1-(2-phthalimidoethyl)-1,1,2(R)-pentanetricarboxylate in the form of a colorless gum.

(iii) In a manner analogous to that described in Example 45(ii)–(iv), from 1,2-dibenzyl 1-tert.butyl 4-methyl-1-(2-phthalimidoethyl)-1,1,2(R)-pentanetriocarboxylate there was obtained $N^2$-[2(R)-[1(R or S)-(carboxy)-3-phthalimidopropyl]-4-methyl]-$N^1$,3-dimethyl-L-valinamide in the form of a white solid, MS: 474 (M+H)+.

EXAMPLE 70

In a manner analogous to that disclosed in the first paragraph of Example 1, from 0.075 g of a 1:1 mixture of isomers of $N^2$-[2(R)-1-(benzyloxycarbamoyl)-2-methylpropyl]-4-methylvaleryl]-$N^1$,3-dimethyl-L-valinamide there was obtained 0.041 g of $N^2$-[2(R)-1-(hydroxycarbamoyl)-2-methylpropyl]-4-methylvaleryl]-$N^1$,3-dimethyl-L-valinamide in the form of a white solid; MS: 358 (M+H)+.

The starting material was obtained as follows:

(i) In a manner analogous to that described in Example 45(i), from 1-benzyl 4-tert.butyl 3-tert.butoxycarbonyl-2(R) isobutylsuccinate and isopropyl iodide there was obtained 1-benzyl 4-tert.butyl 3-tert.butoxycarbonyl-2(R)-isobutyl-3-isopropylsuccinate in the form of an oil; MS 463 (M+H)+.

(ii) In a manner analogous to that described in Example 2(iii) from 1-benzyl-4-tert.butyl 3-tert.butoxycarbonyl-2(R)-isobutyl succinate there was obtained 1-benzyl 2(R)-isobutyl 3(RS)-isopropylsuccinate in the form of a colorless oil; MS: 306 (M+H)+.

(iii) 0.19 g of 1-benzyl 2(R)-isobutyl 3-(RS)-isopropylsuccinate was dissolved in 5 ml of dichloromethane and the solution was cooled to 70°. 5 ml of isobutene were added followed by two drops of concentrated sulphuric acid. The flask was tightly stoppered and the mixture was stirred for 3 days at room temperature. The mixture was poured into 5% aqueous sodium hydrogen carbonate solution and the product was extracted four times with diethyl ether. The combined extracts were washed with 5% aqueous sodium hydrogen carbonate and then saturated aqueous sodium chloride solution. The solution was dried over anhydrous magnesium sulfate and evaporated, and the residue was purified by flash chromatography on silica gel using hexane/diethyl ether (8:1) for the elution. There was obtained 0.134 g of 1-benzyl 4-tert.butyl 2(R)-isobutyl-3-(RS)-isopropylsuccinate in the form of a colorless oil; MS: 363 (M+H)+.

(iv) 0.134 g of 1-benzyl 4-tert.butyl 2(R)-isobutyl-3-(RS)-isopropylsuccinate was dissolved in 10 ml of methanol containing 0.08 g of 10% palladium-on-carbon. After shaking in a hydrogen atmosphere for 8 hours, the catalyst was filtered off and the solvent was removed by evaporation to give 4-tert.butyl 2(R)-isobutyl 3-(RS)-isopropylsuccinate in the form of a colorless gum; MS: 273 (M+H)+.

(v) In a manner analogous to that described in Example 1(i)–(iii) from 4-tert.butyl 2(R)-isobutyl 3-(RS)-isopropylsuccinate there was obtained a 1:1 mixture of isomers of $N^2$-[2(R)-1-(benzyloxycarbamoyl)-2-methylpropyl]-4-methylvaleryl]-$N^1$,3-dimethyl-L-valinamide in the form of a white solid; MS: 399 (M+H)+.

EXAMPLE 71

In a manner analogous to that described in the first paragraph of Example 1, from 0.115 g of $N^2$-[2(R)-[2-(4-biphenyl)-1(R or S)-(benzyloxycarbamoyl)ethyl]-4-methylvaleryl]-$N^1$,3-dimethyl-L-valinamide there was obtained 0.065 g of $N^2$-[2(R)-[2-(4-biphenylyl)-1(R or S)-(hydroxycarbamoyl)-ethyl]-4-methylvaleryl]-$N^1$,3-dimethyl-L-valinamide in the form of a white solid; nmr (MeOD): 7.60≧7.17 (m,9H); 4.36 (s,3H); 2.94–2.68 (m,6H); 2.53–2.42 (m,1H); 1.63–1.52 (m,1H); 1.50–1.33 (m,1H); 1.19–1.08 (m,1H); 1.07 (s,9H); 0.94 (d,3H,J=6); 0.85 (d,3H,J=6); MS: 482 (M+H)+.

The starting material was prepared as follows:

In a manner analogous to that described in Example 45(i)–(v), from 1,2-dibenzyl 1-tert.butyl 4-methyl-1,1,2(R)-pentanetricarboxylate and 4-phenylbenzyl bromide there was obtained $N^2$-[2(R)-[2-(4-biphenylyl)-1(R or S)-(benzyloxycarbamoyl)ethyl]-4-methylvaleryl]-$N^1$,3-dimethyl-L-valinamide in the form of a white solid; MS: 572 (M+H)+.

EXAMPLE 72

In a manner analogous to that described in the first paragraph of Example 1, from 0.155 g of $N^2$-[2(R)-[2-(3-biphenylyl)-1(R or S)-(benzyloxycarbamoyl)ethyl]-4-methylvaleryl]-$N^1$,3-dimethyl-L-valinamide there was obtained 0.105 g of $N^2$-[2(R)-[2-(3-biphenylyl)-1(R or S)-(hydroxycarbamoyl)ethyl]-4-methylvaleryl]-$N^1$,3-dimethyl-L-valinamide in the form of a white solid; nmr (MeOD); 7.58 (m,2H); 7.46–7.28 (m,6H); 7.05 (m,1H); 4.34 (s,1H); 2.98–2.68 (m,6H); 2.54–2.43 (m,1H); 1.62–1.52 (m,1H); 1.49–1.37 (m,1H); 1.23–1.10 (m,1H); 1.07 (s,9H); 0.93 (d,3H,J=6H); 0.85 (d,3H,J=6H); MS: 482 (M+H)+.

The starting material was prepared as follows:

In a manner analogous to that described in Example 45(i)–(v) from 1,2-dibenzyl 1-tert.butyl 4-methyl-1,1,2(R)-pentanetricarboxylate and 3-phenylbenzyl bromide there was obtained $N^2$-[2(R)-[2-(3-biphenylyl)-1(R or S)-(benzyloxycarbamoyl)ethyl]-4-methylvaleryl]-$N^1$,3-dimethyl-L-valinamide in the form of a white solid; MS: 572 (M+H)+.

EXAMPLE 73

In a manner analogous to that described in the first paragraph of Example 1, from 5.52 g of $N^2$-[2(R)-[1(S)-(benzyloxycarbamoyl)ethyl]-4-methylvaleryl]-$N^1$,3-dimethyl-L-valinamide there were obtained 3.92 g of $N^2$-[2(R)-[1-(S)-hydroxycarbamoyl)ethyl]-4-methylvaleryl]-$N^1$,3-dimethyl-L-valinamide as an off-white solid; nmr (CD₃OD): 427 (s,1H); 2.72–2.62 (m,4H); 2.32–2.2(m,1H); 1.58–1.45 (m,1H); 1.43–1.28 (m,1H); 1.13–1.05 (m,4H); 1.02 (s,9H); 0.89 (d,3H,J=5); 0.83 (d,3H,J=5): MS 330 (M+H)+.

The starting material was prepared as follows:

(i) 400 g of D-leucine was dissolved in 5 l of water containing 296 ml of concentrated sulfuric acid and cooled to −2°. A solution of 421 g of sodium nitrite in 1.25 l of water was added slowly while holding the temperature at −2°. The mixture was stirred at 0° for 1.5 hours and then allowed to warm to room temperature overnight. The mixture was extracted three times with ethyl acetate. The combined organic extracts were washed with sodium chloride solution, dried over anhydrous magnesium sulfate and evaporated to give 168 g of D-leucic acid as a pale yellow oil.

The aqueous phase obtained according to the foregoing paragraph was cooled to −2° and treated with sodium nitrite in the same manner as described in that paragraph to give a further 222 g of D-leucic acid as a yellow oil (total yield 390 g).

(ii) 278 g of benzyl bromide were added to a stirred solution of 215 g of D-leucic acid and 246 g of triethylamine in 2.5 l of ethy acetate. The mixture was then heated under reflux for 5 hours, cooled and filtered to remove triethylamine hydrobromide. The filtrate was washed twice with 2M hydrochloric acid, water, saturated sodium bicarbonate solution and then saturated sodium chloride solution. The organic extract was dried over magnesium sulfate and evaporated to give 225 g of D-leucic acid benzyl ester as a yellow liquid.

(iii) A solution of 177 g of D-leucic acid benzyl ester and 69.5 g of pyridine in 500 ml of dichloromethane was added to a stirred solution of 248 g of trifluoromethanesulphonic anhydride in 1 l of dichloromethane over a period of 1.5 hours at 0°. The mixture was stirred at 0° overnight and then washed twice with water, saturated sodium bicarbonate solution and saturated brine. The organic extract was dried over anhydrous magnesium sulfate and evaporated to give 258 g of a brown oil. Flash chromatography on silica gel using 2% ethyl acetate in hexane for elution gave 223 g of benzyl 2(R)-trifluoromethanesulphonyl-4-methylvalerate as a yellow oil; Rf=0.52 (10% ethyl acetate/hexane).

(iv) A solution of 147 g of benzyl t-butylmalonate in 150 ml of dry N,N-dimethylformamide was added dropwise to a stirred suspension of 14.9 g of sodium hydride in 800 ml of N,N-dimethylformamide over a period of 30 minutes. The solution was stirred at room temperature for 1 hour until effervescence had ceased. The solution was cooled to 0° and treated with a solution of benzyl 2-(R)-trifluoromethanesulphonyl-4-methylvalerate in 750 ml of dry dichloromethane. The solution was stirred at 0° for 1 hour and then at room temperature overnight. The solvent was removed by evaporation and the residue was dissolved in 2 l of dichloromethane. The solution was washed with water, saturated sodium bicarbonate solution and sodium chloride solution. The organic extract was dried over anhydrous magnesium sulfate and evaporated to give 276 g of a yellow oil. Flash chromatography on silica gel using 5% ethyl acetate in hexane for the elution gave 230.5 g of 1,2-dibenzyl 1-tert.butyl 4-methyl-1,1,2-(R)-pentanetricarboxylate as a colorless oil.

(v) A solution of 17.05 g of 1,2-dibenzyl 1-tert.butyl 4-methyl-1,1,2-(R)-pentanetricarboxylate in 212 ml of isopropanol was hydrogenated in the presence of 5.2 g of 10% palladium on charcoal. The catalyst was removed by filtration and the filtrate was treated with 10.36 ml of piperidine and 43.7 ml of 40% aqueous formaldehyde. The mixture was stirred at room temperature for 4 days, evaporated to dryness and the residue was dissolved in ethyl acetate. The solution was washed with 5% citric acid solution and saturated sodium chloride solution and then dried over anhydrous magnesium sulfate. The solvent was removed by evaporation and the oil obtained was purified by flash chromatography on silica gel using 1.5% methanol/dichloromethane for the elution to give 7.98 g of 4-tert.butyl-2(R)-isobutyl-3-methylenesuccinate as an oil; MS: 243 (M+H)+.

(vi) A solution of 7.92 g of 4-tert.butyl-2(R)-isobutyl-3-methylenesuccinatein 400 ml of ethyl acetate was hydrogenated in the presence of 790 mg of 10% palladium on charcoal. The catalyst was removed by filtration and the volume of the filtrate was reduced to 70 ml. The solution was heated to 70° and then treated with 6 ml of dicyclohexylamine. The solid was dissolved in 150 ml of ethyl acetate and the solution was allowed to cool overnight. The solid was filtered off, washed with a small amount of dry diethyl ether and recrystallized once from ethyl acetate. The solution was washed twice with 0.5M sulfuric acid, water and saturated sodium chloride solution. The organic layer was dried over anhydrous magnesium sulfate and evaporated to give 3.32 g of 4-tert.butyl-(2(R)-isobutyl-3(S)-methylsuccinate; MS: 245 (M+H)+.

(vii) In a manner analogous to that described in Example 1(i)–(iii), from 3.32 g of 4-tert.butyl-2(R)-isobutyl-3(S)-methylsuccinate there were obtained 5.52 g of $N^2$-[2(R)-[1(S)-(benzyloxycarbamoyl)ethyl]-4-methylvaleryl -$N^1$,3-dimethyl-L-valinamide as a white solid;. MS: 420 (M+H)+.

EXAMPLE 74

In a manner analogous to that described in the first paragraph of Example 44, from 1.34 g $N^2$-[2(R)-[1(RS)-(carboxy)-5-phthalimidopentyl]-4-methylvaleryl]-$N^1$,3-dimethyl-L-valinamide, prepared in a manner analogous to Example 45(i)–(iv), there was obtained 0.42 g of $N^2$-[2(R)-]1-(R or S)-(hydroxycarbamoyl)-5-phthalimidopentyl]-4-methylvaleryl]-$N^1$,3-dimethyl-L-valinamide as a white solid; MS: 517 (M+H)+; nmr: (CD$_3$OD): 8.07 (d,1H,J=10); 7.95 (m,1H); 7.84–7.75 (m,4H); 4.24 (m,1H); 3.59 (t,2H,J=7); 2.7–2.63 (m,4H); 2.13 (m,1H); 1.68–1.54 (m,3H); 1.52–1.46 (m,1H); 1.4–1.28 (m,3H); 1.24–1.13 (m,1H); 1.09–1.02 (m,1H); 1.00 (s,9H); 0.85 (d,3H,J=6); 0.80 (d,3H,J=6).

EXAMPLE 75

In a manner analogous to that described in the first paragraph of Example 1, from 125 mg of $N^2$-[2(R)-[R or S)(benzyloxycarbamoyl)methyl]-4-methylvaleryl]-$N^1$,3-dimethyl-L-valinamide hydrochloride, prepared in a manner analogous to that described in Example 45(i)–(v), there were obtained 62 mg of $N^2$-[2(R)-[(R or S)(amino)(hydroxycarbamoyl)methyl]-4-methylvaleryl]-$N^1$,3-dimethyl-L-valinamide hydrochloride as a buff solid; MS: 331.2345.

EXAMPLE 76

In a manner analogous to that described in the first paragraph of Example 1, from 60 mg of $N^2$-[2(R)-[(R or S)-(benzyloxycarbamoyl)(2-phenacetylamido)methyl]-4-methylvaleryl]-$N^1$,3-dimethyl-L-valinamide, prepared in manner analogous to that described in Example 45(i)–(v), there were obtained 46 mg of $N^2$-[2(R)-[(R or S)-(hydroxycarbamoyl)(2-phenacetylamido)methyl]-4-methylvalenyl]-$N^1$,3-dimethyl-L-valinamide as a buff colored solid; MS: 449 (M+H)+; nmr (CD$_3$OD) 7.32–7.20 (m,5H); 4.45 (d,1H,J=8); 4.23 (s,1H); 3.58–3.46 (m,2H); 3.07–2.90 (m,1H); 2.72 (S,3H); 1.52–1.26 (m,3H); 1.21–1.02 (m,1H); 0.98 (s,9H); 0.86–0.78 (m,6H).

EXAMPLE 77

In a manner analogous to that described in the first paragraph of Example 1, from 200 mg of 4-[[N-2(R)-(benzyloxycarbamoylmethyl)-4-methylvaleryl]-3-methyl-L-valyl]amino]-butyric acid, prepared in a manner analogous to that described in Example 1(i)–(iii), there were obtained 162 mg of 4-[[N-2(R)-(hydroxycarbamoylmethyl)-4-methylvaleryl]-3-methyl-L-valyl]amino]butyric acid as a white powder; MS: 388. (M+H)+; nmr (CD$_3$OD): 7.83 (d,1H,J=9); 4.22 (m,1H); 3.26–3.15 (m,2H); 2.98–2.90 (m,1H); 2.35–2.26 (m,3H); 2.20–2.13 (m,1H); 1.83–1.74 (m,2H); 1.62–1.42 (m,2H); 1.24–1.14 (m, 1H); 1.0 (s,9H); 0.92 (d,3H,J=7); 0.86 (d,3H,J=7).

EXAMPLE 78

In a manner analogous to that described in the first paragraph of Example 1, from 200 mg of methyl-4-[[N-2(R)-[(benzyloxycarbamoyl)methyl]-4-methylvaleryl]-3-methyl-L-valyl]amino]butyrate, prepared in a manner analogous to that described in Example 1(i)–(iii), there were obtained 156 mg of methyl-4-[[N-[2(R)-[(hydroxycarbamoyl)methyl]-4-methylvaleryl]-3-methyl-L-valyl]amino]butyrate as an off white powder: nmr CD$_3$OD): 4.22 (s,1H); 3.66 (s,3H); 3.26–3.13 (m,2H); 2.98–2.89 (m,1H); 2.38–2.26 (m,3H); 2.20–2.13 (m,1H); 1.85–1.71 (m,2H); 1.62–1.42 (m,2H); 1.22–1.13 (m,1H); 1.0 (s,9H); 0.91 (d,3H, J=8); 0.86 (d,3H,J=8).

EXAMPLE 79

In a manner analogous to that described in the first paragraph of Example 1, from 200 mg of 4-[[N-[2(R)-[(benzyloxycarbamoyl)methyl]-4-methylvaleryl]-3-methyl-L-valyl]amino]-N-methyl butyramide, prepared in a manner analogous to that described in Example 1(i)–(iii), there were obtained 139 mg of 4-[[N-[2(R)-[(hydroxycarbamoyl)methyl]-4-methylvaleryl]-3-methyl-L-valyl]amino-N-methyl butyramide as an off white solid; nmr (CD$_3$OD): 4.19 (s,1H); 3.25–3.10 (m,2H); 3.0–2.89 (m,1H); 2.62 (s,3H); 2.35–2.27 (m,1H); 2.22–2.15 (n,2H); 1.82–1.72 (m,2H); 1.62–1.41 (m,2H); 1.23–1.14 1.0 (s,9H); 0.91(d,3H,J=8); 0.86 (d,3H,J=8).

EXAMPLE 80

In a manner analogous to that described in the first paragraph of Example 1, from 0.165 g of $N^2$-[2(R)-[1(R or S)-(benzyloxycarbamoyl)-4-(carbamoyl)butyl]-4-methylvaleryl]$N^1$,3-dimethyl-L-valinamide there were obtained 0.11 g of $N^2$-[2(R)-4-carbamoyl-1(R or S)-(hydroxycarbamoyl)butyl-4-methylvaleryl]-$N^1$,3-dimethyl-L-valinamide in the form of a white solid; nmr (MeOD): 4.15 (s,1H); 2.61 (s,3H); 2.58 (dt,1H,J=11,3); 2.12–2.02 (m,3H); 1.58–1.45 (m,4H) 1.33–1.18 (m,2H); 1.02–0.93 (m,1H); 0.92 (s,9H); 0.78 (d,3H, J=6); 0.73 (d,3H,J=6); MS: 401 (M+H)+.

The starting material was prepared as follows:

A mixture of 0.177 g of $N^2$-[2(R)-[1(R or S)-(benzyloxycarbamoyl)-4-(carboxy)butyl]-4-methylvaleryl]-$N^1$,3-dimethyl-L-valinamide, 0.062 g of 1-hydroxybenzotriazole ammonium salt, 0.05 ml of N-methylmorpholine and 0.078 g of 1-(3-dimethylaminopropyl)-3-ethylcarbodiimide hydrochloride in 5 ml of dry dimethylformamide was stirred for 1 hour at 0° and then for a further 2 days at room temperature. The solution was poured into aqueous sodium hydrogen carbonate solution and the product was extracted with four portions of ethyl acetate. The combined ethyl acetate extracts were washed in succession with aqueous sodium hydrogen carbonate, 1M hydrochloric acid, saturated sodium chloride solution, dried over anhydrous sodium sulfate and evaporated to give 0.166 g of N²-[2(R)-[(R or S)-(benzyloxycarbamoyl)-4-(carboxy)butyl]-4-methylvaleryl]-N¹,3-dimethyl-L-valinamide in the form of a colourless gum; MS: 491 1 (M+N)+.

The following Examples illustrate pharmaceutical preparations containing the amino acid derivatives provided by the present invention:

EXAMPLE A

Tablets containing the following ingredients may be produced in a conventional manner:

| Ingredient | Per Tablet |
| --- | --- |
| Amino acid derivative | 10.0 mg |
| Lactose | 125.0 mg |
| Maize starch | 75.0 mg |
| Talc | 4.0 mg |
| Magnesium stearate | 1.0 mg |
| Total weight | 215.0 mg |

EXAMPLE B

Capsules containing the following ingredients maybe produced in a conventional manner:

| Ingredient | Per Tablet |
| --- | --- |
| Amino acid derivative | 10.0 mg |
| Lactose | 165.0 mg |
| Maize starch | 20.0 mg |
| Talc | 5.0 mg |
| Capsule fill weight | 200.0 mg |

We claim:

1. A compound of the formula

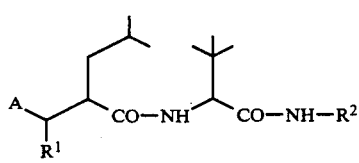

(I)

wherein
A is the group

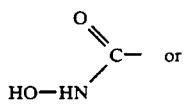

(a)

or

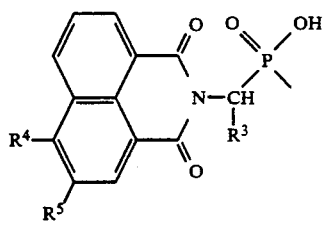

(b)

R¹ is hydrogen, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl or from an aryl-substituted alkanoic acid which contains a maximum of six carbon atoms, lower alkyl or lower alkyl substituted by aryl, hydroxy, protected hydroxy, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl of from an aryl-substituted alkanoic acid which contains a maximum of six carbon atoms, maleimido, succinimido, naphthalimido, 2,3-dihydro-1,3-dioxo-1H-benz[d,e]-isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino;

R² is hydrogen, lower alkyl or lower alkyl substituted by aryl, amino, protected amino, di(lower alkyl)amino, guanidino, carboxyl, protected carboxyl, carbamoyl, mono(lower alkyl)carbamoyl, di(lower alkyl)carbamoyl, di(lower alkoxy)phosphinyl, dihydroxyphosphinyl, pyrrolidino, piperidino or morpholino;

R³ is hydrogen, lower alkyl or lower alkyl substituted by hydroxy, protected hydroxy, amino or protected amino;

R⁴ is hydrogen, hydroxy, lower alkoxy or benzyloxy; and

R⁵ is hydrogen or halogen;

or a pharmaceutically acceptable salt thereof.

2. A compound according to claim 1, wherein R¹ is hydrogen, amino, acetylamino, lower alkyl or lower alkyl substituted by hydroxy, protected hydroxy, amino or protected amino; and R² is hydrogen, lower alkyl or lower alkyl substituted by aryl, amino, protected amino, acetylamino, di(lower alkyl)amino, guanidino, carboxyl, protected carboxyl, di(lower alkoxy)phosphinyl, dihydroxyphosphinyl, pyrrolidino, piperidino or morpholino.

3. A compound according to claim 2, wherein R¹ is hydrogen, amino, acetylamino, benzyloxycarbonylamino, lower alkyl or lower alkyl substituted by amino, phenyl, phthalimido, succinimido, carboxy, alkoxycarbonyl, morpholino, hydroxy or acetoxy.

4. A compound according to claim 3, wherein R¹ is hydrogen, amino, acetylamino, benzyloxycarbonylamino, methyl, 5-aminopentyl, 4-phthalimidobutyl, 5-phthalimidopentyl, 5-hydroxypentyl, 5-acetoxypentyl, aminomethyl, phthalimidomethyl, succinimidomethyl, benzyl, 3-phenylpropyl, 3-carboxypropyl, 3-methoxycarbonylpropyl, benzoylaminomethyl, morpholinomethyl, acetylaminomethyl, 2-phthalimidoethyl, 3-hydroxypropyl or 3-acetoxypropyl.

5. A compound according to claim 4, wherein $R^2$ is lower alkyl or lower alkyl substituted by amino, aryl guanidino, carboxy, di(lower alkoxy)phosphinyl, dihydroxyphosphinyl or morpholino.

6. A compound according to claim 5, wherein $R^2$ is methyl, 4-aminobutyl, 1-phenylethyl, 5-carboxypentyl, diethoxyphosphinylmethyl, dihydroxyphosphinylmethyl or 5-morpholino- pentyl.

7. A compound according to claim 1, wherein $R^3$ is hydrogen, hydroxymethyl, 2-aminoethyl or 4-aminobutyl.

8. A compound according to claim 7, wherein $R^3$ is hydrogen.

9. A compound according to claim 1, wherein $R^4$ is hydrogen, hydroxy or benzyloxy.

10. A compound according to claim 9, wherein $R^4$ is hydrogen or hydroxy.

11. A compound according to claim 1, wherein $R^5$ is hydrogen or bromine.

12. $N^2$-[2(R)-[Hydroxycarbamoylmethyl]-4-methylvaleryl]-$N^1$,3-dimethyl-L-valinamide.

13. $N^2$-[2(R or S)-[1(S)-(Hydroxycarbamoyl)ethyl]-4-methylvaleryl]-$N^1$,3-dimethyl-L-valinamide (isomer 2).

14. $N^2$-[[2-(R or S)-[[[(5-Bromo-2,3-dihydro-6-hydroxy-1,3-dioxo-1H-benz[d,e]isoquinol-2-yl)methyl]-(hydroxy)phosphinyl]-methyl]-4-methylvaleryl]-$N^1$,3-dimethyl-L-valinamide.

15. $N^2$-[2(R or S)-[[(R)-(Amino)[5-bromo-2,3-dihydro-6-hydroxy-1,3-dioxo-1H-benz[d,e]isoquinol-2-yl]methyl](hydroxy)phosphinyl]-methyl]-4-methylvaleryl]-$N^1$,3-dimethyl-L-valinamide.

16. $N^2$-[2(R or S)-[[(R)-(Amino)[(2,3-dihydro-6-hydroxy-1,3-dioxo-1H-benz[d,e]isoquinol-2-yl)methyl]-(hydroxy)phosphinyl]-methyl]-4-methylvaleryl]-$N^1$,3-dimethyl-L-valinamide.

17. $N^2$-[2(R)-[1(R or S)-(Hydroxycarbamoyl)-2-phthalimidoethyl]-4-methylvaleryl]-$N^1$,3-dimethyl-L-valinamide.

18. $N^2$-[2(R)-[1(R or S)-(Hydroxycarbamoyl)-4-(methoxycarbonyl)butyl]-4-methylvaleryl]-$N^1$,3-dimethyl-L-valinamide.

19. $N^2$-[2(R)-[1(R or S)-(Hydroxycarbamoyl)-4-phenylbutyl]-4-methylvaleryl]-$N^1$3-dimethyl-L-valinamide.

20. $N^2$-[2(R)-[1(R or S)-(Hydroxycarbamoyl)-2-succinimidoethyl]-4-methylvaleryl]-$N^1$,3-dimethyl-L-valinamide.

21. A compound of the formula

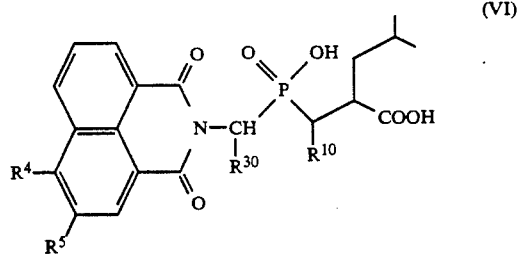

wherein $R^4$ is hydrogen, hydroxy, lower alkoxy or benzyloxy; $R^5$ is hydrogen or halogen; $R^{10}$ is hydrogen, protected amino, acylamino in which acyl is derived from an alkanoic acid which contains a maximum of six carbon atoms, or from a benzoic or naphthoic acid which is optionally substituted with at halogen, lower alkyl, halogenated lower alkyl, lower alkoxy or phenyl or from an aryl-substituted alkanoic acid which contains a maximum of six carbon atoms, lower alkyl or lower alkyl substituted by aryl, protected hydroxy, protected amino, acylamino in which acyl is derived from an alkanoic acid which contains a maximum of six carbon atoms, or from a benzoic or naphthoic acid which is optionally substituted with at halogen, lower alkyl, halogenated lower alkyl, lower alkoxy or phenyl or from an aryl-substituted alkanoic acid which contains a maximum of six carbon atoms, maleimido, succinimodo, naphthalimido, 2,3-dihydro-1,3-dioxo-1H-benz[d,e]isoquinol-2-yl, protected carboxy, carbamoyl, mono(lower alkyl)carbamoyl, di(lower alkyl)carbamoyl, di(lower alkyl)amino, carboxyl-lower alkanoylamino, pyrrolidine or morpholino and $R^{30}$ is hydrogen, lower alkyl or lower alkyl substituted by protected hydroxy or protected amino.

22. A compound of the formula

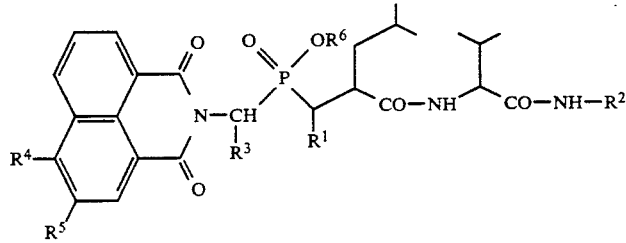

wherein $R^1$ is hydrogen, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl or from an aryl-substituted alkanoic acid which contains a maximum of six carbon atoms, lower alkyl or lower alkyl substituted by aryl, hydroxy, protected hydroxy, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl or from an aryl-substituted alkanoic acid which contains a maximum of six carbon atoms, maleimido, succinimido, naphthalimido, 2,3-dihydro-1,3-dioxo- 1H-benz[d,e]isoquinol-2-yl, carboxy, protected carboxy, carbomoyl, mono(lower alkyl)carbamoyl, di(lower alkyl)carbamoyl, di(lower alkyl)amino, carboxy-lower alkanoylamino, pyrrolidino or morpholino;

$R^2$ is hydrogen, lower alkyl or lower alkyl substituted by aryl, amino, protected amino, di(lower alkyl)amino, guanidino, carboxyl, protected carboxyl, carbamoyl, mono(lower alkyl)carbamoyl, (lower alkyl)carbamoyl, di(lower alkoxy)phosphinyl, dihydroxyphosphinyl, pyrrolidino, piperidino or morpholino;

$R^3$ is hydrogen, lower alkyl or lower alkyl substituted by hydroxy, protected hydroxy, amino or protected amino;

$R^4$ is hydrogen, hydroxy, lower alkoxy or benzyloxy; and $R^5$ is hydrogen or halogen; and $R^6$ is lower alkyl.

23. A pharmaceutical composition comprising an effective amount of a compound of the formula

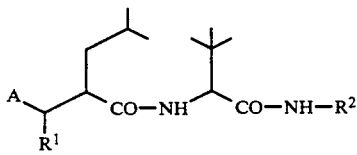

(I)

wherein
A is the group

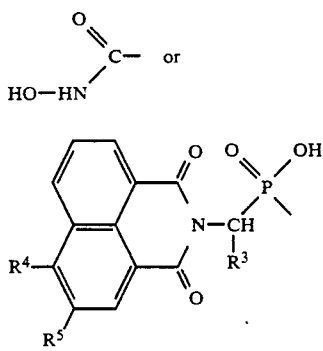

(a)

(b)

$R^1$ is hydrogen, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl or from an aryl-substituted alkanoic acid which contains a maximum of six carbon atoms, lower alkyl or lower alkyl substituted by aryl, hydroxy, protected hydroxy, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl or from an aryl-substituted alkanoic acid which contains a maximum of six carbon atoms, maleimido, succinimido, naphthalimido, 2,3-dihydro-1,3-dioxo-1H-benz[d,e]isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino;

$R^2$ is hydrogen, lower alkyl or lower alkyl substituted by aryl, amino, protected amino, di(lower alkyl)amino, guanidino, carboxyl, protected carboxyl, carbamoyl, mono(lower alkyl)carbamoyl, di(lower alkyl)carbamoyl, di(lower alkoxy)phosphinyl, dihydroxyphosphinyl, pyrrolidino, piperidino or morpholino;

$R^3$ is hydrogen, lower alkyl or lower alkyl substituted by hydroxy, protected hydroxy, amino or protected amino;

$R^4$ is hydrogen, hydroxy, lower alkoxy or benzyloxy; and $R^5$ is hydrogen or halogen or a pharmaceutically acceptable salt thereof.

24. A pharmaceutical composition according to claim 23, wherein $R^1$ is hydrogen, amino, acetylamino, lower alkyl or lower alkyl substituted by hydroxy, protected hydroxy, amino or protected amino; and $R^2$ is hydrogen, lower alkyl or lower alkyl substituted by aryl, amino, protected amino, acetylamino, di(lower alkyl)amino, guanidino, carboxyl, protected carboxyl, di(lower alkoxy)phosphinyl, dihydroxyphosphinyl, pyrrolidino, piperidino or morpholino.

25. A pharmaceutical composition according to claim 24, wherein $R^1$ is hydrogen, amino, acetylamino, benzyloxycarbonylamino, lower alkyl or lower alkyl substituted by amino, phenyl, phthalimido, succinimido, carboxy, alkoxycarbonyl, morpholino, hydroxy or acetoxy.

26. A pharmaceutical composition according to claim 25, wherein $R^1$ is hydrogen, amino, acetylamino, benzyloxycarbonylamino, methyl, 5-aminopentyl, 4-phthalimidobutyl, 5-phthalimidopentyl, 5-hydroxypentyl, 5-acetoxypentyl, aminomethyl, phthalimidomethyl, succinimidomethyl, benzyl, 3-phenylpropyl, 3-carboxypropyl, 3-methoxycarbonylpropyl, benzoylaminomethyl, morpholinomethyl, acetylaminomethyl, 2-phthalimidoethyl, 3-hydroxypropyl or 3-acetoxypyropyl.

27. A pharmaceutical composition according to claim 26, wherein $R^2$ is lower alkyl or lower alkyl substituted by amino, aryl, guanidino, carboxy, di(lower alkoxy)phosphinyl, dihydroxyphosphinyl or morpholino.

28. A pharmaceutical composition according to claim 27, wherein $R^2$ is methyl, 4-aminobutyl, 1-phenylethyl, 5-carboxypentyl, diethoxyphosphinylmethyl, dihydroxyphosphinylmethyl or 5-morpholinopentyl.

29. A pharmaceutical composition according to claim 23, wherein $R^3$ is hydrogen, hydroxymethyl, 2-aminoethyl or 4-amino-butyl.

30. A pharmaceutical composition according to claim 29, wherein $R^3$ is hydrogen.

31. A pharmaceutical composition according to claim 23, wherein $R^4$ is hydrogen, hydroxy or benzyloxy.

32. A pharmaceutical composition according to claim 31, wherein $R^4$ is hydrogen or hydroxy.

33. A pharmaceutical composition according to claim 23, wherein $R^5$ is hydrogen or bromine.

34. A pharmaceutical composition according to claim 23, wherein the compound of formula I is selected from the group consisting of $N^2$-[2(R)-Hydroxycarbamoylmethyl]-4-methylvaleryl]-$N^{13}$-dimethyl-L-valinamide;

$N^2$-[2(R or S)-[1(S)-Hydroxycarbamoyl)ethyl]-4-methylvaleryl]-$N^1$,3-dimethyl-L-valinamide (isomer 2);

N²-[[2(R or S)-[[[(5-Bromo-2,3-dihydro-6-hydroxy-1,3-dioxo-1H-benz[d,e]isoquinol-2-yl)methyl](hydroxy)-phosphinyl]-methyl]-4-methylvaleryl]-N¹,3-dimethyl-L-valinamide;

N²-[2(R or S)-[[(R)-(Amino)-[(5-bromo-2,3-dihydro-6-hydroxy-1,3-dioxo-1H-benz[d,e]isoquinol-2-yl)methyl](hydroxy)phosphinyl]-methyl]-4-methylvaleryl]-N¹,3-dimethyl-L-valinamide;

N²-[2(R or S)-[[(R)-(Amino)[(2,3-dihydro-6-hydroxy-1,3-dioxo-1H-benz[d,e]isoquinol-2-yl)methyl](hydroxy)phosphinyl]-methyl]-4-methylvaleryl]-N¹,3-dimethyl-L-valinamide;

N²-[2(R)-[1(R or S)-Hydroxycarbamoyl)-2-phthalimidoethyl -4-methylvaleryl]-N¹,3-dimethyl-L-dimethyl-L-valinamide;

N²-[2(R)-[1(R or S)-(hydroxycarbamoyl)-4-(methoxycarbonyl)butyl]-4-methylvaleryl]-N¹,3-dimethyll-valinamide;

N²-[2(R)-[1(R or S)-(Hydroxycarbamoyl)-4-phenylbutyl]-4-methylvaleryl]-N¹,3-dimethyl-L-valinamide; and N²-[2-(R)-[1(R or S)-(hydroxycarbamoyl)-2-succinimidoethyl]-4-methylvaleryl]-N¹,3-dimethyl-L-valinamide.

35. A method of controlling or preventing degenerative joint diseases comprising administering to a host in need of such control or prevention an effective amount of a compound of the formula

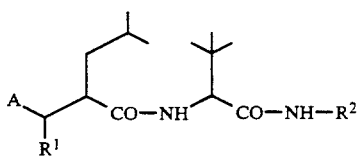

(I)

wherein

A is the group

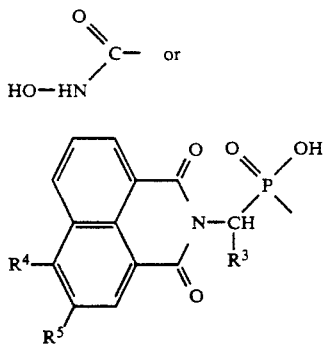

(a)

or (b)

$R^1$ is hydrogen, amino, protected amino, acylamino in which acyl is derived from an alkanoic acid which contains a maximum of six carbon atoms, or from a benzoic or naphthoic acid which is optionally substituted with halogen, lower alkyl, halogenated lower alkyl, lower alkoxy or phenyl or from an aryl-substituted alkanoic acid which contains a maximum of six carbon atoms, lower alkyl or lower alkyl substituted by aryl, hydroxy, protected hydroxy, amino, protected amino, acylamino in which acyl is derived from an alkanoic acid which contains a maximum of six carbon atoms, of from a benzoic or naphthoic acid which is optionally substituted with halogen, lower alkyl, halogenated lower alkyl, lower alkoxy or phenyl of from an aryl-substituted alkanoic acid which contains a maximum of six carbon atoms, maleimido, succinimido, naphthalimido, 2,3-dihydro-1,3-dioxo-1H-benz[d,e]isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino;

$R^2$ is hydrogen, lower alkyl or lower alkyl substituted by aryl, amino, protected amino, di(lower alkyl)amino, guanidino, carboxyl, protected carboxyl, carbamoyl, mono(lower alkyl)carbamoyl, di(lower alkyl)carbamoyl, di(lower alkoxy)phosphinyl, dihydroxyphosphinyl, pyrrolidino, piperidino or morpholino;

$R^3$ is hydrogen, lower alkyl or lower alkyl substituted by hydroxy, protected hydroxy, amino or protected amino;

$R^4$ is hydrogen, hydroxy, lower alkoxy or benzyloxy; and $R^5$ is hydrogen or halogen or a pharmaceutically acceptable salt thereof.

36. A method according to claim 35, wherein $R^1$ is hydrogen, amino, acetylamino, lower alkyl or lower alkyl substituted by hydroxy, protected hydroxy, amino or protected amino; and $R^2$ is hydrogen, lower alkyl or lower alkyl substituted by aryl, amino, protected amino, acetylamino, di(lower alkyl)amino, guanidino, carboxyl, protected carboxyl, di(lower alkoxy)phosphinyl, dihydroxyphosphinyl, pyrrolidino, piperidino or morpholino.

37. A method according to claim 36, wherein $R^1$ is hydrogen, amino, acetylamino, benzyloxycarbonylamino, lower alkyl or lower alkyl substituted by amino, phenyl, phthalimido, succinimido, carboxy, alkoxycarbonyl, morpholino, hydroxy or acetoxy.

38. A method according to claim 37, wherein $R^1$ is hydrogen, amino, acetylamino, benzyloxycarbonylamino, methyl, 5-aminophenyl, 4-phthalimidobutyl, 5-phthalimidopentyl, 5-hydroxypentyl, 5-acetoxypentyl, aminomethyl, phthalimidomethyl, succinimidomethyl, benzyl, 3-phenylpropyl, 3-carboxypropyl, 3-methoxycarbonylpropyl, benzoylaminomethyl, morpholinomethyl, acetylaminomethyl, 2-phthalimidoethyl, 3-hydroxypropyl or 3-acetoxypropyl.

39. A method according to claim 35, wherein $R^2$ is lower alkyl or lower alkyl substituted by amino, aryl, guanidino, carboxy, di(lower alkoxy)phosphinyl, dihydroxy-phosphinyl or morpholino.

40. A method according to claim 39, wherein $R^2$ is methyl, 4-aminobutyl, 1-phenylethyl, 5-carboxypentyl, diethoxyphosphinylmethyl, dihydroxyphosphinylmethyl or 5-morpholino- pentyl.

41. A method according to claim 40 wherein $R^3$ is hydrogen, hydroxymethyl, 2-aminoethyl or 4-aminobutyl.

42. A method according to claim 41, wherein $R^3$ is hydrogen.

43. A method according to claim 35, wherein $R^4$ is hydrogen, hydroxy or benzyloxy.

44. A method according to claim 43, wherein $R^4$ is hydrogen or hydroxy.

45. A method according to claim 35, wherein $R^5$ is hydrogen or bromine.

* * * * *